(12) United States Patent
Jackson et al.

(10) Patent No.: US 12,076,084 B2
(45) Date of Patent: *Sep. 3, 2024

(54) METHODS, APPARATUS, AND SYSTEMS FOR OPHTHALMIC TESTING AND MEASUREMENT

(71) Applicant: LUMITHERA DIAGNOSTICS, INC., Poulsbo, WA (US)

(72) Inventors: Gregory R. Jackson, Hershey, PA (US); David E. Beecher, Shippensburg, PA (US); David E. Orr, Piedmont, SC (US); Frank Jones, Carp, CA (US); Nathan Smith, Lewistown, PA (US)

(73) Assignee: LumiThera Diagnostics, Inc., Poulsbo, WA (US)

( * ) Notice: Subject to any disclaimer, the term of this patent is extended or adjusted under 35 U.S.C. 154(b) by 427 days.

This patent is subject to a terminal disclaimer.

(21) Appl. No.: 16/890,811

(22) Filed: Jun. 2, 2020

(65) Prior Publication Data
US 2020/0288968 A1 Sep. 17, 2020

Related U.S. Application Data

(63) Continuation of application No. 16/578,286, filed on Sep. 21, 2019, now Pat. No. 10,667,683.
(Continued)

(51) Int. Cl.
*A61B 3/00* (2006.01)
*A61B 3/02* (2006.01)
(Continued)

(52) U.S. Cl.
CPC ............ *A61B 3/063* (2013.01); *A61B 3/0008* (2013.01); *A61B 3/005* (2013.01); *A61B 3/0075* (2013.01);
(Continued)

(58) Field of Classification Search
CPC ....... A61B 3/063; A61B 3/005; A61B 3/0075; A61B 3/0008; A61B 3/0033; A61B 3/0041; A61B 3/0091
See application file for complete search history.

(56) References Cited

U.S. PATENT DOCUMENTS 2,234,240 A 3/1941 Frohring
2,239,164 A 4/1941 Wigelsworth
(Continued)

FOREIGN PATENT DOCUMENTS

EP 1274339 A1 1/2003
EP 1911393 A2 4/2008
(Continued)

OTHER PUBLICATIONS

Chang, L., "For Just $25, You Can Use Your Smartphone to Give Yourself a Glaucoma Test." Digital Trends, Sep. 11, 2016, www.digitaltrends.com/health-fitness/viewi-glaucoma-test/. https://www.digitaltrends.com/health-fitness/viewi-glaucoma-test, retrieved on Jun. 6, 2018, 8 pages.

(Continued)

*Primary Examiner* — Dawayne Pinkney
(74) *Attorney, Agent, or Firm* — Seed IP Law Group LLP

(57) ABSTRACT

Methods, apparatus, and systems for performing an ophthalmic diagnostic test are disclosed. In one aspect, a head-wearable device for administering an ophthalmic test to a subject can comprise a head-wearable frame for mounting the device onto the subject's head, and a light seal configured for coupling to the frame so as to isolate at least one eye of the subject from ambient light when the device is worn by the subject.

16 Claims, 41 Drawing Sheets

Related U.S. Application Data

(60) Provisional application No. 62/853,713, filed on May 28, 2019, provisional application No. 62/734,274, filed on Sep. 21, 2018, provisional application No. 62/734,280, filed on Sep. 21, 2018.

(51) Int. Cl.
*A61B 3/024* (2006.01)
*A61B 3/028* (2006.01)
*A61B 3/06* (2006.01)
*G02B 27/01* (2006.01)
*G08B 21/18* (2006.01)
*A61B 3/10* (2006.01)
*A61B 5/00* (2006.01)

(52) U.S. Cl.
CPC .............. *A61B 3/022* (2013.01); *A61B 3/024* (2013.01); *A61B 3/028* (2013.01); *G02B 27/0172* (2013.01); *G02B 27/0176* (2013.01); *G08B 21/182* (2013.01); *A61B 3/0025* (2013.01); *A61B 3/0033* (2013.01); *A61B 3/0041* (2013.01); *A61B 3/0091* (2013.01); *A61B 3/102* (2013.01); *A61B 5/6803* (2013.01)

(56) References Cited

U.S. PATENT DOCUMENTS

| | | | |
|---|---|---|---|
| 2,247,653 A | 7/1941 | Feldman | |
| 2,283,769 A | 5/1942 | Schwanzel | |
| 4,545,658 A | 10/1985 | Weiss | |
| 4,971,434 A | 11/1990 | Ball | |
| 5,381,195 A | 1/1995 | Rootzen et al. | |
| 5,550,602 A | 8/1996 | Braeuning | |
| 5,655,228 A | 8/1997 | Chiang | |
| 5,671,039 A | 9/1997 | Grolman | |
| 5,715,334 A | 2/1998 | Peters | |
| 5,822,037 A | 10/1998 | Barad | |
| 5,920,374 A | 7/1999 | Vaphiades et al. | |
| 5,946,075 A | 8/1999 | Horn | |
| 6,027,217 A | 2/2000 | McClure et al. | |
| 6,176,581 B1 | 1/2001 | Newsome | |
| 6,313,169 B1 | 11/2001 | Bowen et al. | |
| 6,315,412 B1 | 11/2001 | Snodderly et al. | |
| 6,325,513 B1 | 12/2001 | Bergner et al. | |
| 6,386,706 B1 | 5/2002 | McClure et al. | |
| 6,443,977 B1 | 9/2002 | Jaillet | |
| 6,478,424 B1 | 11/2002 | Grinvald et al. | |
| 6,533,419 B1 | 3/2003 | Newsome | |
| 6,579,235 B1 | 6/2003 | Abita et al. | |
| 6,592,222 B2 | 7/2003 | Massengill et al. | |
| 6,715,878 B1 | 4/2004 | Gobbi et al. | |
| 6,863,399 B1 | 3/2005 | Newsome | |
| 6,895,264 B2 | 5/2005 | Rice et al. | |
| 6,912,301 B1 | 6/2005 | Lin et al. | |
| 7,166,079 B2 | 1/2007 | Febbroriello et al. | |
| 7,448,751 B2 | 11/2008 | Kiderman et al. | |
| 7,494,222 B2 | 2/2009 | Jackson et al. | |
| 7,520,614 B2 | 4/2009 | Joos et al. | |
| 7,665,845 B2 | 2/2010 | Kiderman et al. | |
| 7,731,360 B2 | 6/2010 | MacDougall et al. | |
| 7,740,592 B2 | 6/2010 | Graham et al. | |
| 7,753,523 B2 | 7/2010 | Kiderman et al. | |
| 7,783,332 B2 | 8/2010 | Aufer et al. | |
| 7,798,646 B2 | 9/2010 | Jackson et al. | |
| 7,866,818 B2 | 1/2011 | Schroeder et al. | |
| 7,931,370 B2 | 4/2011 | Prat Bartomeu | |
| 7,972,278 B2 | 7/2011 | Graham et al. | |
| 8,434,868 B2 | 5/2013 | Sato et al. | |
| 8,550,627 B2 | 10/2013 | Wang et al. | |
| 8,795,191 B2 | 8/2014 | Edwards et al. | |
| 9,050,021 B2 | 6/2015 | Jackson et al. | |
| 9,066,667 B1 | 6/2015 | Berme et al. | |
| 9,101,296 B2 | 8/2015 | Schroeder et al. | |
| 9,198,571 B2 | 12/2015 | Kiderman et al. | |
| 9,213,163 B2 * | 12/2015 | Lewis | A61B 3/113 |
| 9,226,856 B2 | 1/2016 | Walsh et al. | |
| 9,237,847 B2 | 1/2016 | Wang et al. | |
| 9,247,870 B2 | 2/2016 | Kiderman et al. | |
| 9,289,123 B2 | 3/2016 | Weibel et al. | |
| 9,301,675 B2 | 4/2016 | Kiderman et al. | |
| 9,492,083 B2 | 11/2016 | Rege et al. | |
| 9,504,379 B2 | 11/2016 | Jackson et al. | |
| 9,572,485 B2 | 2/2017 | Jackson et al. | |
| 9,730,579 B2 | 8/2017 | Jackson et al. | |
| 9,757,031 B2 | 9/2017 | Wang et al. | |
| 9,848,773 B2 | 12/2017 | Su | |
| 9,888,841 B2 | 2/2018 | Hogan | |
| 9,888,842 B2 | 2/2018 | White et al. | |
| 9,949,637 B1 | 4/2018 | Wong et al. | |
| 10,667,683 B2 * | 6/2020 | Jackson | G08B 21/182 |
| 10,849,547 B2 | 12/2020 | Scott | |
| 11,344,194 B2 | 5/2022 | Jackson et al. | |
| 2003/0004418 A1 | 1/2003 | Marmorstein | |
| 2003/0212310 A1 | 11/2003 | Febbroriello et al. | |
| 2004/0087843 A1 | 5/2004 | Rice et al. | |
| 2005/0010091 A1 | 1/2005 | Woods et al. | |
| 2006/0062557 A1 | 3/2006 | Imada | |
| 2006/0200013 A1 * | 9/2006 | Smith | A61B 5/6821 |
| | | | 600/319 |
| 2006/0227290 A1 | 10/2006 | Murray et al. | |
| 2007/0038142 A1 | 2/2007 | Todd et al. | |
| 2007/0121071 A1 | 5/2007 | Jackson et al. | |
| 2008/0013047 A1 | 1/2008 | Todd et al. | |
| 2008/0192202 A1 | 8/2008 | Lewkowski | |
| 2009/0076367 A1 | 3/2009 | Sit et al. | |
| 2009/0231545 A1 | 9/2009 | Peyman | |
| 2010/0149073 A1 * | 6/2010 | Chaum | G02B 27/017 |
| | | | 345/8 |
| 2010/0152565 A1 | 6/2010 | Thomas et al. | |
| 2010/0168606 A1 | 7/2010 | Edwards et al. | |
| 2010/0292999 A1 | 11/2010 | Verma | |
| 2011/0082704 A1 | 4/2011 | Blum | |
| 2011/0176106 A1 | 7/2011 | Lewkowski | |
| 2011/0218456 A1 | 9/2011 | Graham et al. | |
| 2011/0234977 A1 | 9/2011 | Verdooner | |
| 2011/0267577 A1 | 11/2011 | Verma | |
| 2011/0299034 A1 | 12/2011 | Walsh et al. | |
| 2012/0257163 A1 | 10/2012 | Dyer et al. | |
| 2013/0033677 A1 | 2/2013 | MacDougall et al. | |
| 2013/0066213 A1 | 3/2013 | Wellington | |
| 2014/0340641 A1 | 11/2014 | Edwards et al. | |
| 2014/0354949 A1 | 12/2014 | Bakar et al. | |
| 2015/0009313 A1 * | 1/2015 | Noda | G06V 40/40 |
| | | | 348/78 |
| 2015/0062530 A1 | 3/2015 | Henry | |
| 2015/0238166 A1 | 8/2015 | Heath et al. | |
| 2016/0015289 A1 | 1/2016 | Simon et al. | |
| 2016/0051145 A1 | 2/2016 | Rickard et al. | |
| 2016/0070105 A1 | 3/2016 | Tannoudiji | |
| 2016/0278630 A1 | 9/2016 | Walsh et al. | |
| 2017/0000324 A1 | 1/2017 | Samec et al. | |
| 2017/0000325 A1 | 1/2017 | Samec et al. | |
| 2017/0000326 A1 | 1/2017 | Samec et al. | |
| 2017/0000329 A1 | 1/2017 | Samec et al. | |
| 2017/0000330 A1 | 1/2017 | Samec et al. | |
| 2017/0000331 A1 | 1/2017 | Samec et al. | |
| 2017/0000332 A1 | 1/2017 | Samec et al. | |
| 2017/0000333 A1 | 1/2017 | Samec et al. | |
| 2017/0000334 A1 | 1/2017 | Samec et al. | |
| 2017/0000335 A1 | 1/2017 | Samec et al. | |
| 2017/0000337 A1 | 1/2017 | Samec et al. | |
| 2017/0000340 A1 | 1/2017 | Samec et al. | |
| 2017/0000341 A1 | 1/2017 | Samec et al. | |
| 2017/0000342 A1 | 1/2017 | Samec et al. | |
| 2017/0000343 A1 | 1/2017 | Samec et al. | |
| 2017/0000345 A1 | 1/2017 | Samec et al. | |
| 2017/0000454 A1 | 1/2017 | Samec et al. | |
| 2017/0000683 A1 | 1/2017 | Samec et al. | |
| 2017/0007111 A1 | 1/2017 | Samec et al. | |
| 2017/0007115 A1 | 1/2017 | Samec et al. | |
| 2017/0007116 A1 | 1/2017 | Samec et al. | |
| 2017/0027444 A1 | 2/2017 | Rege et al. | |
| 2017/0065166 A1 | 3/2017 | Sudou et al. | |

(56) References Cited

U.S. PATENT DOCUMENTS

| | | |
|---|---|---|
| 2017/0150925 A1 | 6/2017 | Jung |
| 2017/0311794 A1 | 11/2017 | Inoue et al. |
| 2017/0325675 A1 | 11/2017 | Liu et al. |
| 2017/0325676 A1 | 11/2017 | Lichtenauer |
| 2017/0332896 A1 | 11/2017 | Inoue et al. |
| 2017/0332903 A1 | 11/2017 | Wang et al. |
| 2017/0337737 A1* | 11/2017 | Edwards ............... F16M 13/04 |
| 2017/0354324 A1 | 12/2017 | Bennett |
| 2017/0354327 A1 | 12/2017 | Kiderman et al. |
| 2018/0008141 A1 | 1/2018 | Krueger |
| 2018/0008142 A1 | 1/2018 | Garoon et al. |
| 2018/0103917 A1 | 4/2018 | Kim et al. |
| 2018/0110409 A1 | 4/2018 | Tsapakis |
| 2018/0263488 A1* | 9/2018 | Pamplona ............ A61B 3/0041 |
| 2019/0021588 A1 | 1/2019 | Maier et al. |
| 2019/0133441 A1 | 5/2019 | Verdooner et al. |
| 2019/0142270 A1 | 5/2019 | Monhart et al. |
| 2019/0307350 A1 | 10/2019 | Sridhar |
| 2020/0008666 A1* | 1/2020 | Anton Garcia ...... A61B 3/0091 |
| 2020/0301150 A1 | 9/2020 | Breed et al. |
| 2020/0397281 A1 | 12/2020 | Pundlik |
| 2021/0315453 A1 | 10/2021 | Jeon |

FOREIGN PATENT DOCUMENTS

| | | |
|---|---|---|
| EP | 2416696 A1 | 2/2012 |
| JP | H04191137 | 7/1992 |
| RU | 2190343 | 10/2002 |
| WO | WO2004112601 | 6/2004 |
| WO | 2005023094 A2 | 3/2005 |
| WO | 2008100613 A2 | 8/2008 |
| WO | 2010115870 A1 | 10/2010 |
| WO | 2011042722 A1 | 4/2011 |
| WO | 2014015378 A1 | 1/2014 |
| WO | 2014182769 A1 | 11/2014 |
| WO | 2015145111 A2 | 10/2015 |
| WO | 2016022215 A1 | 2/2016 |
| WO | 2016070188 A1 | 5/2016 |
| WO | 2016182974 A1 | 11/2016 |
| WO | 2017035406 A2 | 3/2017 |
| WO | 2017182596 A1 | 10/2017 |
| WO | WO2017194898 | 11/2017 |
| WO | 2017208227 A1 | 12/2017 |
| WO | 2018085598 A1 | 5/2018 |

OTHER PUBLICATIONS

Curcio, C. et al., "Human Photoreceptor Topography," Journal of Comparative Neurology, vol. 292 (4): 497-523 (1990).

Estanol, I. "Patenting Pharmaceutical Inventors at the EPO—Latest Developments," European Patent Office, Pharmacy, EPO, 20 pages (Jun. 2006).

Gisler, C. et al., "Towards Glaucoma Detection Using Intraocular Pressure Monitoring, International Conference of Soft Computing and Pattern Recognition," IEEE: 255-260 (2014).

Giuliano, A., "Wearable Dark-adaptometer in Normal Adult Healthy Volunteers," ClinicalTrials.gov, 6 pages (2016).

Goh, R. et al., "Objective Assessment of Activity Limitation in Glaucoma with Smartphone Virtual Reality Goggles, A Pilot Study," Trans Vis Sci Tech., vol. 7(1), Article 10: 14 pages (2018).

Goldstein, E. B. et al., Sensation and Perception, Eighth Edition, 490 pages (2010).

Goseki, T. et al., "Bilateral concurrent eye examination with a head-mounted perimeter for diagnosing functional visual loss," Neuro-Ophthalmology, vol. 40 (6):281-285 (2016).

Hirschberg, D., et al., "Assessment of Wearable Sensor Technologies for Biosurveillance," Organization Report No. ECBC-TR-1275, Army Edgewood Chemical Biological Center APG MD Research and Technology DIR, 52 pages (2014).

Hollander, D. A., et al., "Use of a portable head mounted perimetry system to assess bedside visual fields," British Journal of Ophthalmology, vol. 84:1185-1190 (2000).

Hou, F., et al., "Evaluating the performance of the quick CSF method in detecting contrast sensitivity function changes," Journal of Vision, vol. 16(6):1-19 (2016).

International Invitation to Pay Additional fees, PCT/US2019/052303, dated Jan. 14, 2020, 19 pages.

Jackson, G. et al., "Inner retinal visual dysfunction is a sensitive marker of non-proliferative diabetic retinopathy," Br J Ophthalmol .; vol. 96:699-703 (2012).

Jackson, G., et al. "Aging and dark Adaptation," Vision Research, vol. 39 (Issue 23): 3975-3982 (1999).

Jones, P. et al., "Visual Field of Endeavor," The Ophthalmologist, June Issue: 14-24 (2019).

Kim, J., et al., "Wearable smart sensor systems integrated on soft contact lenses for wireless ocular diagnostics," Nature Communications, vol. 8(14997):8 pages (2017).

Krader, C., "Identifying Glaucoma-Related Visual Function Loss" Ophthalmology Times, vol. 6(4):2 pages (2018).

Labrique, A. et al., "A novel device for assessing dark adaptation in field settings," BMC Ophthalmology, vol. 15:74 (2015).

Mang, O-Y, et al., "A wearable infrared video pupillography with multi-stimulation of consistent illumination for binocular pupil response," International Society for Optics and Photonics, Design and Quality for Biomedical Technologies IX, Proc. of SPIE, vol. 9700: 7 pages (2016).

Matsumoto, C., et al., "Visual field testing with head-mounted perimeter 'imo'," PloS One, vol. 11(8):e0161974, 12 pages (2016).

Mohaghegh, N. et al., "Wearable Diagnostic System for Age-Related Macular Degeneration," 38th Annual International Conference of the Engineering in Medicine and Biology Society (EMBC): 6006- 6009 (2016).

Nakanishi, M., et al., "Detecting Glaucoma With a Portable Brain-Computer Interface for Objective Assessment of Visual Function Loss," JAMA Ophthalmology, vol. 135(6): 550-557 (2017).

Owsley, C., et al., "Delayed rod-mediated dark adaptation is a functional biomarker for incident early age-related macular degeneration," Ophthalmology, vol. 123(2):344-351 (2016).

Pugh, E.N., Jr., "Rushton's Paradox:Rod Dark Adaptation After Flash Photolysis," J. Physiol., vol. 248: 413-431 (1975).

Salvatore, G. A., et al., "Wafer-scale design of lightweight and transparent electronics that wraps around hairs," Nature Communications, vol. 5 (2982): 8 pages (2014).

Wolf, G. "The Discovery of the Visual Function of Vitamin A," The Journal of Nutr., vol. 131:1647-1650 (2001).

Wroblewski, D., et al., "Testing of visual field with virtual reality goggles in manual and visual grasp modes," BioMed Research International, vol. 2014 (Article ID 206082) 10 pages (2014).

Yamao, S., et al., "Effects of head tilt on visual field testing with a head-mounted perimeter imo," PloS One, vol. 12 (9): e0185240, 11 pages, (2017).

Yang Lab, "Bidirectional Neural Communication & Closed-Loop Neuromodulation," UMN, yanglabumn.com/research. html retrieved on Jun. 6, 2018 16 pages.

Yang Lab, "Wearable Electronics and System in Healthcare and Lifestyle Applications," UMN, yanglabumn.com/research.html retrieved on Jun. 6, 2018, 4 pages.

de Azevedo, Dario Francisco Guimaraes, "Automated Imaging Dark Adaptometry in Human Retina," A Dissertation, University of Miami (206 pages) (Aug. 1996).

Kolb, Fernandez, Nelson, "Webvision, The Organization of the Retina and Visual System," Creel Clinical Electrophysiology (1849 pages—2 parts) (2020).

International Search Report and Written Opinion for PCT/US2019/052303, dated Mar. 9, 2020, 19 pages.

* cited by examiner

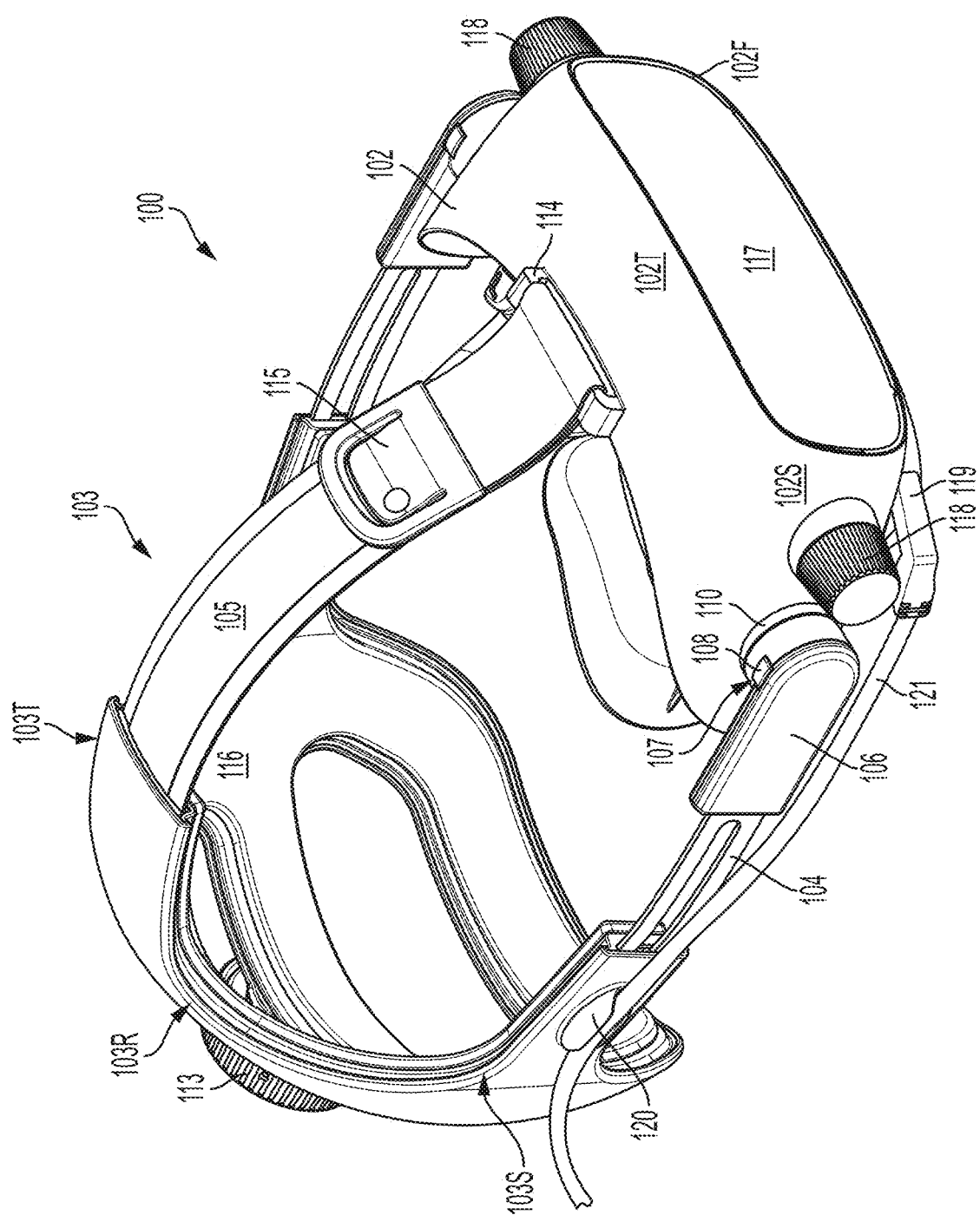

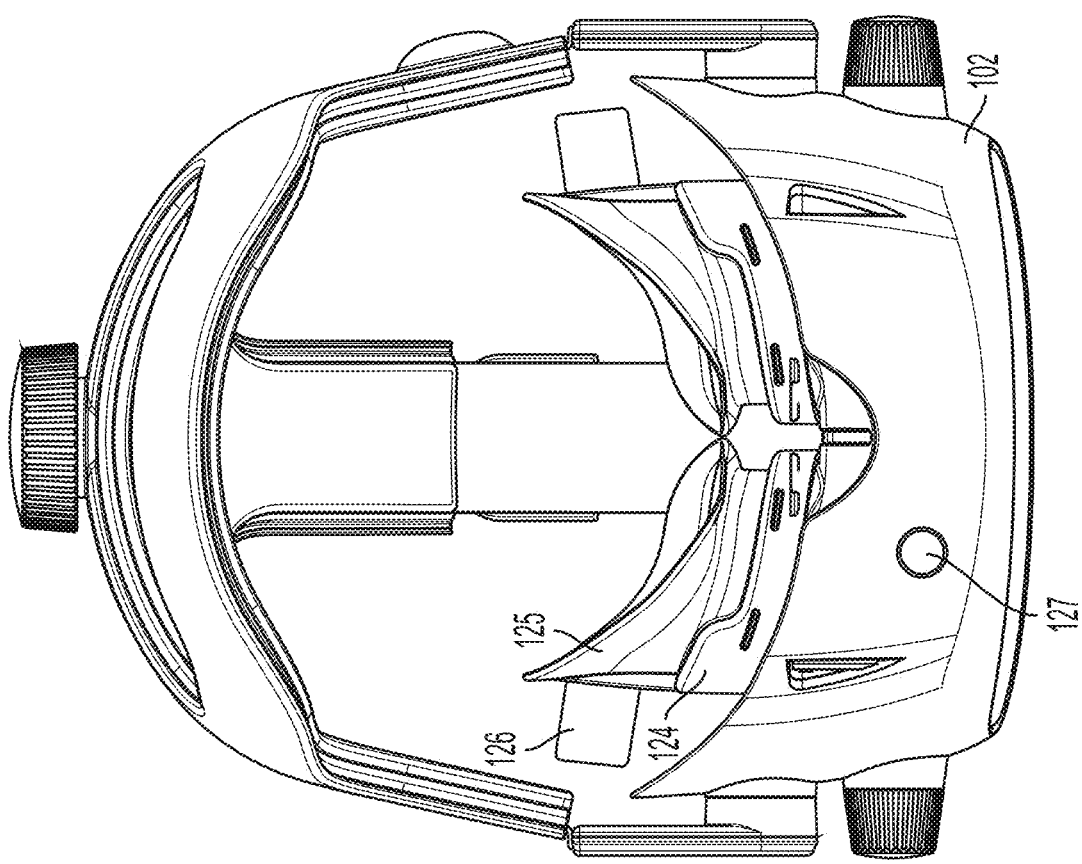

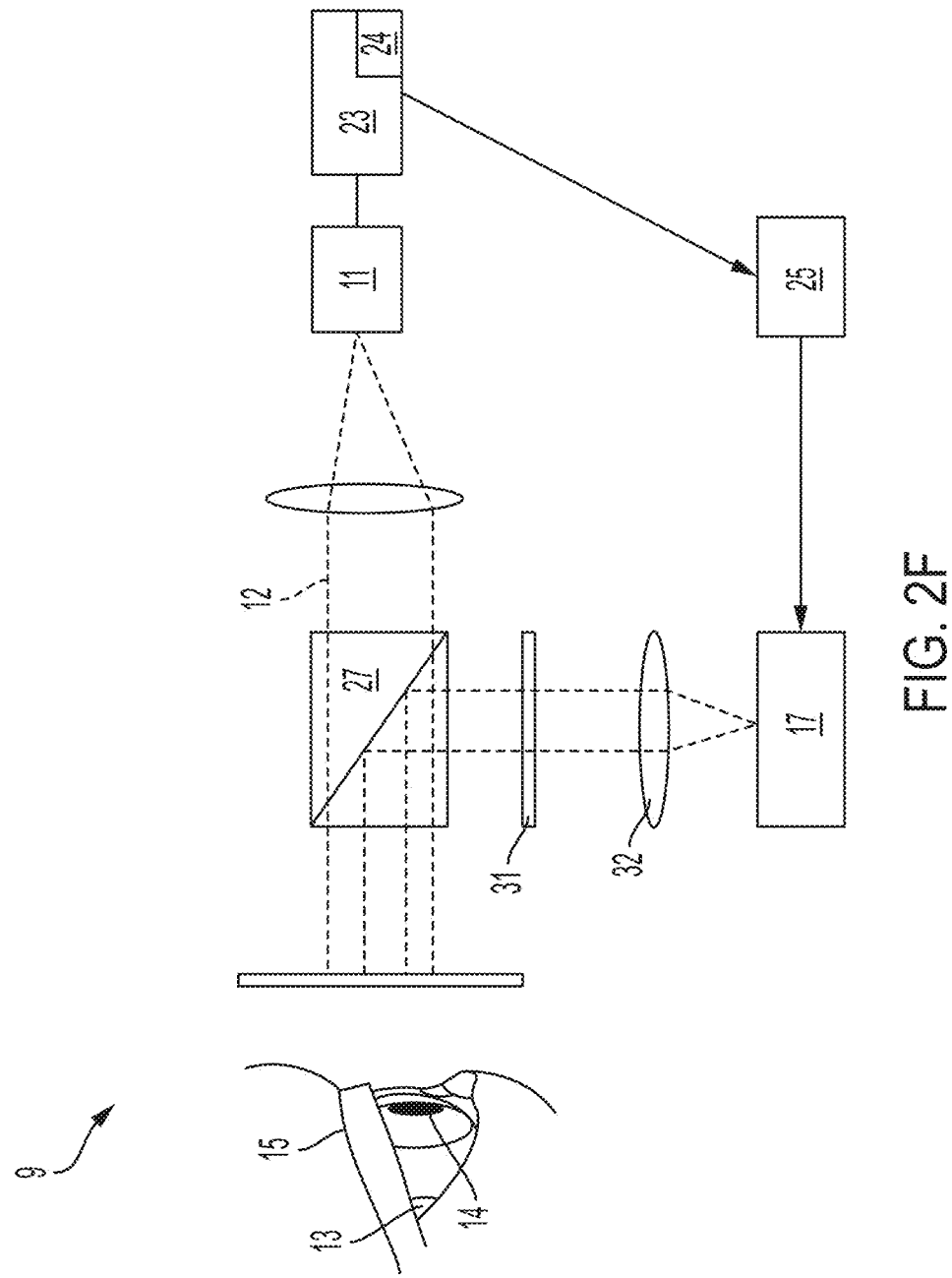

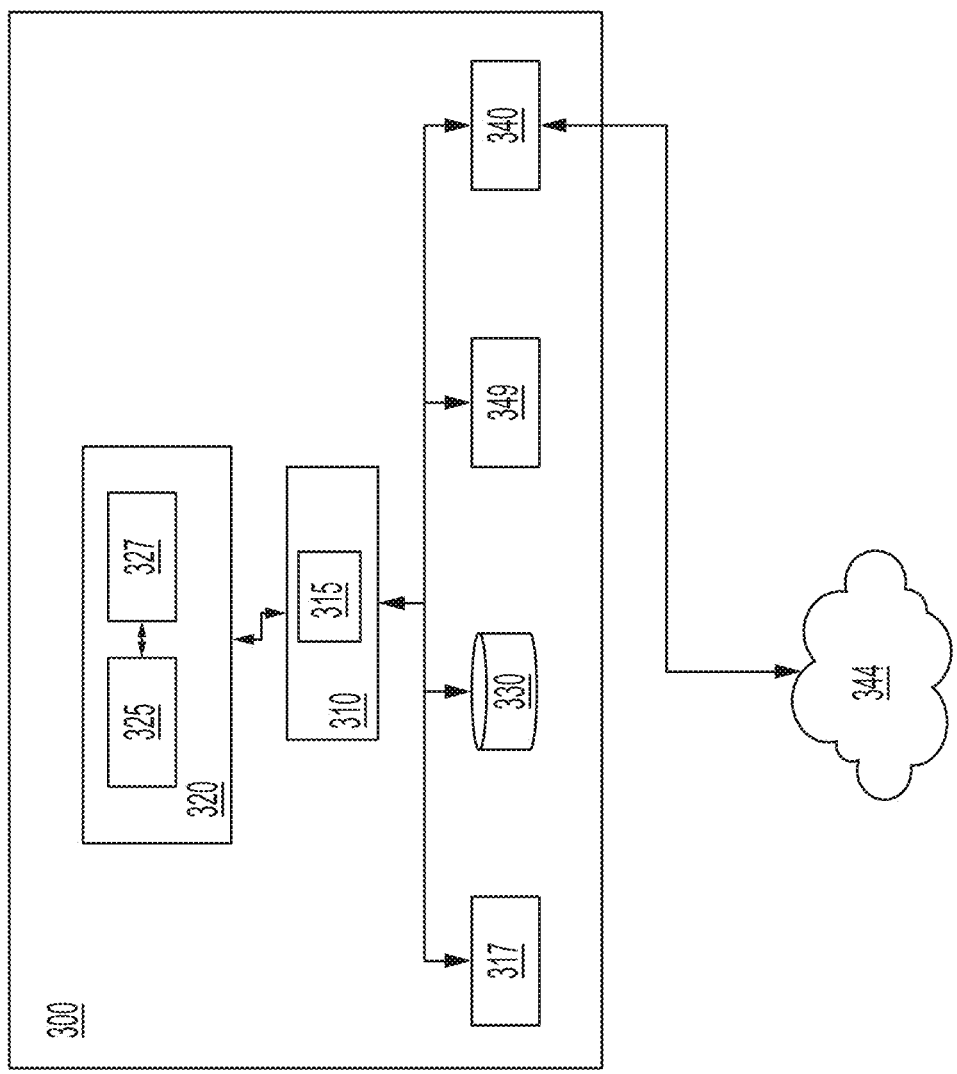

METHODS, APPARATUS, AND SYSTEMS FOR OPHTHALMIC TESTING AND MEASUREMENT

RELATED APPLICATIONS

The Application is a continuation of U.S. patent application Ser. No. 16/578,286, filed on Sep. 21, 2019 (U.S. Pat. No. 10,667,683), which claims the benefit of and priority to U.S. Provisional Application No. 62/734,274, filed on Sep. 21, 2018, U.S. Provisional Application No. 62/734,280, filed on Sep. 21, 2018, and U.S. Provisional Application No. 62/853,713, filed on May 28, 2019. The entire teachings of these earlier applications are incorporated herein by reference.

FIELD

The present disclosure generally relates to ophthalmic diagnostic methods and systems, and more particularly to methods, apparatus, and systems for performing ophthalmic diagnostic testing and measurements.

BACKGROUND

The macula of the human eye is generally understood as having been designed for providing detailed vision. The macula can have a relatively large area, measuring often about six millimeters in diameter and covering about 21.5 degrees of visual angle centered on the fovea. The macula is understood as being responsible for producing central, high resolution, color vision, and, as such, any damage to the macula (e.g., damage caused by macular degeneration) can result in impairment or loss of such vision.

The human macula can be divided into a number of sub-regions, namely the umbo, foveola, foveal avascular zone, fovea, parafovea, and perifovea areas. The fovea comprises a small area dominated by cone-shaped cells, and is surrounded by parafovea, which is sub-region of the macula, generally dominated by rod-shaped cells. As detailed in U.S. Pat. No. 9,504,379, the entire teachings of which is incorporated by reference herein, the rod-shaped cells appear to be responsible for vision in dim light, while the cone-shaped cells are understood to be responsive to bright light and colors. In young adults, the number of rod-shaped cells outnumbers the cone-shaped cells by approximately 9:1. This proportion of the rod-shaped cells to cone-shaped cells changes as a person ages.

The health and function of the rod-shaped and the cone-shaped photoreceptors are maintained by the pigmented layer of retina or retinal pigment epithelium (RPE), the Bruch's membrane (BM), which is located between the retinal pigment epithelium and the fenestrated choroidal capillaries of the eye, and the capillary lamina of choroid or choriocapillaris, which is located adjacent to Bruch's membrane in the choroid (collectively referred to as the RPE/Bruch's membrane complex).

The RPE is a dedicated layer of nurse cells behind the neural retina, which is understood to be responsible for sustaining photoreceptor health in a number of ways, including, but not limited to, maintaining proper ionic balance, transporting and filtering nutrients, providing retinoid intermediates to replenish photopigment bleached by light exposure and absorbing stray photons. Bruch's membrane, which comprises a vessel wall of about 2-6 µm, further separates the RPE and the choriocapillaris. The choriocapillaris provides blood flow to the outer retina, particularly the rods.

An impairment of the RPE/Bruch's membrane complex can result in reduced transportation of nutrient and oxygen to the photoreceptors and reduced clearance of by-products of bleaching, such as opsin, thereby impairing the health and function of the photoreceptors. This can be especially true with the rod-shaped cell photoreceptors, which are responsible for scotopic, or dark-adapted vision.

SUMMARY

In one aspect, a head-wearable device for measurement of dark adaptation in at least one eye of a subject is disclosed. The head-wearable system can comprise a head-wearable frame, at least one test light source mounted in the frame, and an optical system mounted in the frame for directing the light from the at least one test light source onto at least one eye of the subject (e.g., onto the retina of the at least one eye). The at least one test light source can be configured to generate a bleaching light and a stimulus light.

In another aspect, a device for administering an ophthalmic diagnostic test to a subject is disclosed. The device can comprise an ophthalmic diagnostic system for administering an ophthalmic diagnostic test to at least one eye of the subject and an automatic subject-instruction system for communicating with the subject so as to guide the subject through the diagnostic test.

In yet another aspect, an ophthalmic testing system is disclosed. The ophthalmic testing system can comprise an optical system configured to direct at least one ray of light onto an eye of a test subject, a processor coupled to the optical system, a memory coupled to the processor, and one or more programs stored in the memory and configured to be executed by the one or more processors. The one or more programs can include instructions for configuring the ophthalmic testing system for use in conducting an ophthalmic test on the test subject.

In another aspect, an electronic device for ophthalmic testing is disclosed. The electronic device can comprise one or more processors, a memory connected to the one or more processors, and one or more programs stored in the memory and configured to be executed by the one or more processors. The one or more programs can include instructions for: providing, using the processor, a test subject with one or more commands for guiding the test subject through an ophthalmic test administered using an ophthalmic measurement and testing device, the one or more commands being provided to the test subject in natural language, receiving, at the processor, one or more requests for assistance, the one or more requests being issued by the test subject in natural language, extracting one or more active elements of an active ontology associated with the one or more requests, determining at least one task for which to provide the test subject with assistance based on the active ontology, and providing the test subject with assistance by performing the at least one task.

In yet another aspect, an ophthalmic testing system is disclosed. The ophthalmic testing system can comprise an optical system configured to direct at least one ray of light onto an eye of a test subject; at least one motion sensor coupled to the optical system; one or more processors coupled to the motion sensor; a memory coupled to the processor; and one or more programs stored in the memory and configured to be executed by the one or more processors; the one or more programs including instructions for receiving information regarding movements of the ophthalmic testing system from the motion sensor indicating sudden acceleration or deceleration of the ophthalmic testing system.

In another aspect, a system comprising a status monitor and a processor is disclosed. The status monitor can comprise one or more sensors, each configured to monitor status of at least one feature of a medical testing system, where the at least one feature can be a feature indicative of an operational aspect of the medical testing system. The processor can be coupled to the status monitor and configured to receive information regarding the at least one feature of the medical testing system from the one or more sensors and in an event the information indicates a change in an expected value of the feature, generate a notification to an entity interested in monitoring the operation of the medical testing system.

In yet another aspect, a system for measuring dark adaptation is disclosed. The system can comprise a plurality of head-wearable devices, each configured for measuring dark adaptation of at least one eye of a subject and a command center configured to communicate with the plurality of head-wearable devices.

In another aspect, a light seal for use in a head-wearable device configured for measuring dark adaptation of a subject is disclosed. The light seal can comprise a conformable body having at least one opening adapted to be substantially aligned with at least one eye of the subject when the light seal is worn by the subject and an attachment element coupled to the conformable body for mounting the light seal to a subject's head. The body can be configured for coupling to a frame of the head-wearable device such that a combination of the head-wearable device and the light seal isolate the at least one eye of the subject from ambient light when worn.

In yet another aspect, a head-wearable device for administering an ophthalmic test to a subject is disclosed. The a head-wearable device can comprise a head-wearable frame for mounting the device onto the subject's head, and a light seal configured for coupling to the frame so as to isolate at least one eye of the subject from ambient light when the device is worn by the subject.

In another aspect, a head-wearable device for administering an ophthalmic diagnostic test to a subject is disclosed. The head-wearable device can comprise a head-wearable frame, a diagnostic system coupled to the frame for performing an ophthalmic diagnostic test, the diagnostic system comprising at least one test light source generating test light for illuminating at least one eye of the subject, and an automatic alignment mechanism coupled to the frame for automatically aligning the at least one light source relative to the pupil of the subject's eye.

In other examples, the aspects above, or any system, method, apparatus described herein can include one or more of the following features.

The one or more programs can comprise instructions for establishing, using the processor, verbal communication with the test subject for guiding the test subject through the ophthalmic test. The verbal communication with the subject can be conducted using natural language. Further, the verbal communication with the test subject can be performed by using one or more pre-recorded messages configured for delivery to the test subject before, during, and after the ophthalmic test.

The ophthalmic testing system can comprise at least one audio speaker for conducting the verbal communication with the test subject. The verbal communication can comprise one or more commands conveyed to the test subject. The one or more commands can comprise commands provided for guiding the test subject through the ophthalmic test. Further, the verbal communication can comprise at least one of 1) greeting the test subject, 2) commands providing address or location of an exam room in which the ophthalmic test is administered, 3) information regarding the ophthalmic test, and 4) expected wait time until the ophthalmic test is administered.

The ophthalmic testing system can further comprise an interface configured to receive a response from the test subject. The response can be provided by the test subject in connection with one or more stimuli provided by the ophthalmic testing system to the test subject. Further, the processor can be configured to monitor the response received from the test subject via the interface. The processor can further be configured to at least one of 1) store the response received from the test subject for future analysis and 2) compare the response received from the test subject to a baseline response stored in the memory. Moreover, the processor can be configured to adjust at least one function of the ophthalmic testing system based on the response received from the test subject. The at least one function can include at least one of: 1) position of a component of the optical system, 2) orientation of a component of the optical system, and 3) length of the ophthalmic test.

Further, the interface can be configured for use by the test subject to provide the response. The response received from the test subject can include at least one of a verbal response or a response provided via interaction with the interface. The processor can also be configured to provide the test subject with additional commands based on the response received from the test subject. The additional commands can comprise at least one of 1) natural language commands, 2) pre-recorded audio commands, 3) computer-generated audio commands, and 4) visual commands.

The ophthalmic testing system can further comprise a user interface configured for use by the test subject to provide the response. The response received from the test subject can be a verbal response.

The ophthalmic testing system can further comprise a biometric scanner configured to obtain at least one biometric feature of the test subject. The at least one biometric feature can comprise at least one of a facial feature of the test subject, information obtained from an iris of the eye of the test subject, information obtained from a retina of the eye of the test subject, and a fingerprint obtained from the test subject.

In some embodiments, the processor can be configured to store a profile for the test subject, the profile including identifying information including at least one of: name of the test subject, address of the test subject, any identifiers associated with the test subject, and health insurance information for the test subject. The profile can be obtained from an electronic health record system. Further, the electronic health record system is maintained on a cloud-based server.

The ophthalmic testing system can further comprise a biometric sensor that measures at least one biometric feature of the test subject. The processor can also be configured to identify the test subject using the at least one biometric feature. Further, the processor can be configured to receive and store, in the memory of the ophthalmic testing system, at least one medical history of the test subject, medical insurance information associated with the test subject, available pretesting diagnostics information associated with the test subject.

In some embodiments, one or more commands for guiding the test subject can include at least one of 1) address or location of an exam room in which the ophthalmic test is administered, 2) information regarding the ophthalmic test, and 3) expected wait time until the ophthalmic test is administered. The one or more commands can comprise pre-recorded messages configured for delivery to the test subject before, during, and after the ophthalmic test.

Additionally or alternatively, the processor can be configured to communicate with a location-determining device associated with the test subject to monitor a location of the test subject for guiding the test subject to the exam room. Further, the processor can configured to communicate with a plurality of speakers for guiding the test subject to the exam room, wherein the processor can be configured to activate each of the speakers based on proximity of the location of the test subject to that speaker. In some embodiments, the processor can be configured to communicate with a program executing on a mobile device associated with the test subject for presenting a map to the test subject for visually guiding the test subject to the exam room. The location-determining device can comprise an RFID tag. Further, the location-determining device can comprise a smartphone.

Further, the at least one or more requests for assistance can include at least one of 1) questions regarding the test and 2) complaints regarding the test. The instructions can be configured to provide the test subject with assistance by performing at least one of: 1) guiding the test subject in conducting the ophthalmic testing, 2) notifying a practitioner monitoring the ophthalmic testing, 3) adjusting at least one function of the ophthalmic measurement and testing device, and 4) configuring at least one element of the ophthalmic measurement and testing device.

Furthermore, the processor can be configured to store a profile for the test subject, the profile including identifying information including at least one of: name of the test subject, address of the test subject, any identifiers associated with the test subject, and health insurance information for the test subject.

The electronic can further comprise a biometric scanner configured to obtain at least one biometric feature of the test subject. The at least one biometric feature can comprise at least one of a facial feature of the test subject, information obtained from an iris of the eye of the test subject, information obtained from a retina of the eye of the test subject, and a fingerprint obtained from the test subject. Further, the processor can be configured to store the at least one biometric feature of the test subject in a biometric database in the memory of the electronic device.

Further, the one or more programs further can include instructions for receiving the at least one biometric feature from the biometric scanner, determining whether the biometric database includes a matching biometric feature to the at least one biometric feature, and in an event the matching biometric feature exists, identify the test subject using the matching biometrics information. The one or more programs can further include instructions for monitoring performance of the test subject during the ophthalmic test in response to the stimuli. Alternatively or additionally, the one or more program can include instructions for providing the test subject with verbal commands in response to the performance of the test subject during the ophthalmic test in response to the stimuli. Further, the one or more program can include instructions for adjusting at least one function of ophthalmic measurement and testing device the in response to the performance of the test subject during the ophthalmic test in response to the stimuli. Moreover, the one or more programs can include instructions for recording results of the ophthalmic test in response to the stimuli as performed by the test subject. In certain embodiments, the one or more programs can further include instructions for recording results of the ophthalmic test in a cloud-based or clinic-based electronic health record or subject folder for the test subject.

In some embodiments, the electronic device can comprise at least one of a audio speaker for providing the one or more commands for guiding the test subject in natural language and an audio microphone for receiving the one or more requests for assistance in natural language from the test subject. The electronic device can further comprise an interface configured to a receive, from the test subject, a response to one or more stimuli provided by the ophthalmic measurement and testing device.

In some embodiments, the programs comprise instructions to be executed by the one or more processors for generating a notification in response to receiving information regarding sudden acceleration or deceleration of the ophthalmic testing system. The programs can further comprise instructions to be executed by the one or more processors for transmitting the notification to a designated device. The designated device can comprises any of a mobile device, a desktop computer, earbud, smart glasses with pop-up message window. Furthermore, the programs can comprise instructions configured to be executed by the one or more processors for generating an alarm signal in response to the sudden acceleration or deceleration of the ophthalmic testing system. Additionally or alternatively, the one or more programs can comprise instructions for storing number of detected sudden acceleration or deceleration events in the database. Further, the one or more programs can comprise instructions for quantifying severity of the sudden acceleration or deceleration events detected by the motion sensor. Furthermore, the one or more programs can comprise instructions for quantifying the sudden acceleration or deceleration events as mild, medium, and severe.

The ophthalmic testing system can also comprise a communication module for communicating with the designated device. The designed device can be configured to send one or more instructions to the ophthalmic testing system in response to the notification. Further, the processor of the ophthalmic testing device can be configured to execute the instructions received by the designated device. Moreover, the one or more instructions sent by the designated device can comprise instructions for disabling the ophthalmic testing device, providing a visual warning signal to the test subject, and/or providing an audible warning signal to the test subject.

Further, the ophthalmic testing system can comprise one or more speakers for generating the alarm signal. The alarm signal can comprise a message in natural language.

In some embodiments, the sensor comprise an inertial measurement sensor (IMS). The ophthalmic testing system can also comprise a database in communication with the processor.

The at least one feature can comprise at least one of temperature, acceleration, deceleration and orientation of the medical testing system.

Further, the one or more sensors can comprise at least one of a motion sensor, a temperature sensor, a humidity sensor, microphone, global positioning system (GPS), gyroscope, light sensor, proximity sensor, system clock, and an accelerometer. Further, the one or more sensors can comprise at least one sensor configured to detect whether a cover of the medical testing system is opened. In some embodiments, the at least one sensor can comprises an infrared sensor. The one or more sensors can also comprise an accelerometer. The processor can be configured to analyze the information received from the accelerometer to determine a sudden acceleration or deceleration of the medical testing system. Additionally or alternatively, the sensors can be configured to be integrated into a single printed circuit board or dispersed throughout the medical testing system on multiple printed circuit boards.

Moreover, the entity can be at least one of a remote entity responsible for maintenance of the medical testing system and an insurance provider providing insurance on the medical testing system. The processor can also be configured to send an alarm signal to the entity. The processor can further be configured to receive a message from the entity in response to the notification. Moreover, the processor can be configured to convey the message to the user of the system. The processor can also be configured with pre-established rules corresponding to different magnitudes of sensor readings. The rules can also govern the nature of a notification to the user or entity.

The system can further comprise a communications network coupled to the processor. The processor can be configured to transmit the notification to the remote entity via the communications network.

The processor can further be configured to issue the alarm signal to a user of the medical testing system. The system can also be integrally included onboard of the medical testing device. Further, the system can be implemented on a chip included in the medical testing device and comprise a database configured to store a log of the notifications generated by the processor. The database can be stored either in a cloud-based server or onboard the device.

In some embodiments, the system can automate responses to insurance and warranty damage claims made by a user. The system can also system monitor real-time operating conditions such as current to ensure the testing protocol.

In some embodiments, the system can maintain its own battery backup to ensure monitoring of the medical testing system even when the medical testing system is turned off.

The head-wearable device can further comprise a movable platform on which the at least one test light source and the optical system are mounted. The movable platform can be movable along at least two orthogonal directions for aligning the at least one test light source relative to the pupil of the subject's eye. Alternatively or additionally, the platform can be fixedly positioned relative to the frame.

The head-wearable device can further comprise at least one fixation light source associated with the at least one test light source for directing the subject's attention to the at least one test light source.

Further, the at least one fixation light source and the at least one test light source can be positioned relative to one another such that a light beam emitted by the at least one test light source and a light beam emitted by the fixation light source form an angle in a range of about 1 to about 18 degrees at the subject's pupil. Moreover, the at least one fixation light source can be movable so as to allow bringing the fixation light into focus when viewed by the subject. The at least one fixation light source can also be movable along a direction substantially along a propagation direction of light emitted by the fixation light source.

The head-wearable device can further comprise a mechanism mounted onto the frame and coupled to the at least one fixation light source for moving the fixation light source relative to the subject's eye. The mechanism can be configured to move the fixation light source along a direction substantially along a propagation direction of light emitted by the fixation light source. Further, the mechanism for moving the at least one fixation light source can comprise a knob adapted to be rotated by a user, and a cam system mechanically coupled to the knob for transforming rotational motion of the knob to linear translation of the fixation light source.

Moreover, the optical system can comprise one or more lenses configured to collimate light emitted by the at least one test light source. Also, the optical system can comprise at least one aspheric lens adapted to correct for spherical aberration.

In some embodiments, the test light source and the optical system can be housed in a sealed package. The head-wearable device can also comprise an automatic alignment mechanism coupled to the frame for automatically aligning the at least one test light source with the pupil of the subject's eye. The automatic alignment mechanism can comprise an infrared light source mounted onto the frame for illuminating the at least one eye and an infrared detector mounted in the frame for detecting at least a portion of the infrared light returning from the at least one eye in response to the infrared illumination. Further, the infrared detector can comprise an infrared camera. Further, in some embodiments, the infrared camera can be configured to generate an image of the subject's pupil based on the infrared light returning from the at least one eye of the subject.

The head-wearable device can further comprise a feedback system mounted onto the frame and in communication with the infrared detector and the movable platform. The feedback system can detect the pupil of the at least one eye based on one or more signals generated by the infrared detector and cause movement of the platform to align the light emitted by the at least one test light source with the subject's pupil. Further, the feedback system can align the light emitted by the at least one test light source based on a shape of the subject's pupil in the image generated by the infrared camera.

The optical system can also comprise a dichroic mirror adapted to reflect the light from the at least one test light source onto the subject's pupil and further to allow passage of the infrared light returning from the subject's eye onto the infrared detector.

Further, the head-wearable device can comprise a light seal configured for coupling to the frame to isolate the at least one eye from ambient light when the device is worn by the subject. The light seal can be configured to isolate both eyes of the subject from ambient light. Additionally or alternatively, the light seal can be configured to isolate the eyes of the subject from ambient light independent of one another. Further, the light seal can be substantially conformable to at least a portion of the subject's head.

The light seal can comprise a polymeric material. The polymeric material can comprise any of silicone, polyurethane, neoprene, polyolefin, nitrile rubber, ethylene vinyl acetate (EVA), polyvinyl alcohol (PVA), polylactic acid (PLA). Additionally or alternatively, the light seal can comprise a plurality of fibers. For example, the fibers can comprise cellulose fibers. Additionally or alternatively, the light seal can comprise a foamed material. The foamed material can comprise any of alginate foam and starch-based foam. In some embodiments, an RFID tag can be coupled to the light seal.

The light seal comprises a conformable body having at least one opening adapted to be substantially aligned with the at least one eye of the subject when the light seal is worn by the subject, the body being configured for coupling to a frame of the head-wearable device such that the combination of the head-wearable device and the light seal isolate the at least one eye of the subject from ambient light when worn. In some embodiments, an attachment element can be coupled to the conformable body for removably and replaceably attaching the light seal to at least a portion of the subject's head. For example, the attachment element can comprise a strap. Further, the attachment element can comprise at least one arm coupled to the conformable body. Additionally or alternatively, a hygienic liner can be configured for coupling with a surface of the conformable body of the light seal so as to be in contact with the subject's skin. In some embodiments, the hygienic liner can be a single-use, disposable item. In some embodiments, the hygienic liner can comprise a double-sided tape.

In some embodiments, the head-wearable device can further comprise one or more light sensors coupled to the frame for detecting light leakage through the light seal. The one or more light sensors can be positioned so as to detect light leakage in vicinity of at least one eye of the subject. Further, the one or more light sensors can comprise at least two light sensors each of which is positioned to detect light leakage in vicinity of one eye of the subject.

The head-wearable device can further comprise an alert module mounted onto the frame and in communication with the one or more light sensors for generating an alert when the detected light leakage is greater than a threshold. The alert module can be configured to identify the eye in vicinity of which the light leakage is detected. Further, the alert module is configured to generate an audio alert in response to the detection of the light leakage.

In some embodiments, the alert module can be configured to inform an individual administering the dark adaptation test of completion of the test. Further, the alert module can be configured to generate an alarm signal in response to malfunction of the at least one test light source. Additionally or alternatively, alert module can be configured to generate an alarm signal in response to performance of the subject during the dark adaptation measurement.

The head-wearable device can further comprise at least one sensor coupled to the frame for generating a signal in response to detection of an undesired motion of the subject. The sensor can be in communication with the alert module to send the signal thereto and configured to generate an alarm in response to the sensor signal.

The head-wearable device can further comprise a ratchet mounted on the frame and coupled to the light seal for adjusting the light seal around the at least one eye of the subject. The head-wearable device can also comprise a first strap for mechanically coupling the ratchet to the light seal. The ratchet can be used to adjust any of a length and tension in the strap for adjusting the light seal around the at least one eye of the subject. The head-wearable device can further comprise a second strap coupled to the frame for adjusting attachment of the frame to the subject's head. The head-wearable device can also comprise a quick release button coupled to any of the first and the second strap to allow facile release thereof.

The stimulus light can have a spectrum effective in stimulating the rod photoreceptors of the at least one eye. For example, the stimulus light can have one or more wavelengths in a range of about 400 nm to about 570 nm. Further, the light source that generates the stimulus light can be configured to generate light stimuli having a duration in a range of about 100 milliseconds to about 400 milliseconds. In some embodiments, the stimulus light can have an intensity in a range of about $4 \times 10^{-5}$ cd/m2 to about 5 cd/m2.

Further, the bleaching light can have one or more wavelengths in a range of about 490 nm to about 510 nm or a range of about 600 nm to about 700 nm. Additionally or alternatively, the bleaching light can have a wavelength spectrum consisting essentially of wavelengths in a range of about 490 nm to about 510 nm. In some embodiments, the bleaching light can have a wavelength spectrum consisting essentially of wavelengths in a range of about 600 nm to about 700 nm.

In some embodiments, the test light source can be configured to generate bleaching light pulses having a duration in a range of about 0.5 milliseconds to about 400 milliseconds. Additionally or alternatively, the bleaching light can have an intensity in a range of about 1.5 log Scotopic Trolands/sec to about 8 log Scotopic Trolands/sec and/or an intensity in a range of about 3 log Scotopic Trolands/sec to about 7 log Scotopic Trolands/sec.

Further, the at least one test light source can comprise two light sources, one of which can be configured to generate the bleaching light and the other is configured to generate the stimulus light.

In some embodiments, the frame can comprise a body having a chamber for housing the at least one light source and the optical system. The chamber can comprise a first compartment for housing the at least one test light source and the optical system. The first compartment can be sealed against external environment. Further, the frame body can be configured such that at least a portion thereof is positioned in front of the at least one eye when the head-wearable device is worn by a subject. The portion of the frame body can be opaque so as to obstruct passage of ambient light to the at least one eye. Further, the opaque portion can be hingedly coupled to another portion of the frame such that the opaque portion can be lifted so as to allow passage of ambient light to the at least one eye of the subject. In some embodiments, the at least a portion of the frame body that is configured for positioning substantially in front of the at least one eye of the subject when the device is worn by a subject can be formed of a material having an adjustable opacity in response to a signal. Further, at least a portion of the frame body can comprise a liquid crystal and a light polarizer for providing a transition from translucent to opaque upon application of a voltage thereto.

The frame can also comprise an opening configured to be substantially in front of the at least one eye of the subject when the device is worn by the subject. In some embodiments, the frame can comprise a flip seal coupled to the opening to obstruct or to allow passage of ambient light to the at least one eye. A first strap can be coupled to the frame for securing the frame to the subject's head. The strap can comprise at least one of an elastic material or a non-elastic material.

The head-wearable device can further comprise a slidable screen coupled to the frame, wherein the screen can be slidably positioned substantially in front of the at least one eye of the subject so as to obstruct passage of light thereto.

The head-wearable device can also comprise a controller that is mounted on the frame. The controller can be configured to control operation of the at least one test light source.

In some embodiments, the head-wearable can comprise a subject-response interface configured to allow the subject to provide feedback in response to exposure to light emitted by the at least one test light. An analyzer can also be mounted on the frame and be in communication with the subject-response interface and configured to analyze the feedback. The analyzer can be configured to analyze the feedback of the subject for assessing dark adaptation of the at least one eye of the subject. The analyzer can comprise a processor and at least one memory module in communication with the processor. the least one memory module stores instructions for analyzing the response of the subject to the stimulus light.

The head-wearable device can further comprise an adaptive automated subject-instruction system mounted onto the frame for instructing a subject during performance of the dark adaptation measurement. The head-wearable device can further comprise a system for monitoring at least one attribute of the at least one eye.

Further, the monitoring system can be in communication with the automated subject-instruction system to cause the subject-instruction system to provide one or more instructions to the subject in response to monitoring of the attribute.

The head-wearable can also comprise an audio module mounted to the frame for providing audio communication with the subject. The audio module can be in communication with the subject-instruction system for receiving subject instruction signals from the system and converting the signals to audible signals for the subject. The audio module can convert the subject instruction signals to one or more verbal commands for delivery to the subject. The verbal commands can be generated based on performance of the subject during the dark adaptation measurement. The audio module can also convert one or more alarm signals generated by the alarm module into audible signals for the subject.

The head-wearable device can also comprise a controller coupled to the frame for controlling the at least one test light source. Further, the head-wearable device can comprise a display coupled to the frame, the display being controlled by the controller. The controller can effect presentation of any of information, selection options and/or command options on the display. The information can comprise status of the dark adaption test and/or subject data. The selection options can allow a user to select right eye, left eye, or both eyes of the subject for administration of the dark adaptation test thereto. Further, the selection options can allow selecting a protocol for performing the dark adaptation measurement. The selection options can allow selecting a communication protocol for establishing communication between the head wearable device and another device. The display can also present software-controlled buttons for allowing a user to input data into the head-wearable device.

The head-wearable device can further comprise a communication module coupled to the frame. The communication module can be configured to communicate with a command center. For example, the communication module can communicate with the command center via a wireless protocol. The communication module can also be configured to communicate with a headset. Specifically, the communication module can communicate with the headset via a wired connection. Additionally or alternatively, the communication module can communicate with the headset via a wireless protocol. The communication module can also be configured to communicate with an electronic health record (EHR) system. Further, the communication module is configured to communicate with a database providing shared access to the head-wearable device and the EHR system. In some embodiments, the communication module can employ encryption for communication. Also, the communication module can be configured to transmit a notice signal to the command center indicative of performance of the dark adaptation measurement. The communication module can further transmit the notice signal to a mobile device of a medical professional.

In some embodiments, the command center can be configured to communicate concurrently with the plurality of head-wearable devices. Further, at least one of the head-wearable devices can comprise a subject-instruction system in communication with the command center. The command center can be configured to allow a user to provide instructions to a subject using the at least one head-wearable device via the subject-instruction system.

The light seal attachment element can comprise a strap coupled to the conformable body and/or at least one arm coupled to the conformable body. The light seal can also comprise a hygienic liner configured for coupling with a surface of the conformable body of the light seal so as to be in contact with the subject's skin. The hygienic liner can be a single-use, disposable item and/or comprise a double-sided tape. In some embodiments, the light seal can comprise a polymeric material. The polymeric material can comprise any of silicone, polyurethane, neoprene, polyolefin, nitrile rubber, ethylene vinyl acetate (EVA), polyvinyl alcohol (PAV), and polylactic acid (PLA). In some embodiments, the light seal can comprise a plurality of fibers. The plurality of fibers can comprise cellulose fibers. Further, the light seal can comprise a foamed material. The foamed material can comprise any of close-cell or open-cell polymeric foam, alginate foam, and starch-based foam.

In some embodiments, the light seal can comprise an RFID tag coupled to the light seal. The RFID tag can be used to authenticate the light seal and single use thereof.

Further, a testing device according to examples disclosed herein can comprise a measurement system for monitoring performance of the subject during the ophthalmic diagnostic test. The measurement system can comprise a subject-response device configured for use by the subject to respond to one or more stimuli provided by the ophthalmic diagnostic system.

The subject-instruction system can comprise pre-recorded messages for delivery to the subject before, during and/or subsequent to administration of the ophthalmic diagnostic test. Further, the subject-instruction system can be configured to allow communication between the subject and a medical professional.

Further, the subject-instruction system can be in communication with the subject-response device so as to receive data regarding the subject's response to the stimuli. The subject-instruction system can be configured to provide verbal commands to the subject in response to the data regarding the subject's response to the stimuli.

A testing device according to embodiments disclosed herein can provide an ophthalmic test including at least one of: Visual field for glaucoma, Frequency Doubling Technology Perimetry (FDT) for glaucoma and diabetic retinopathy, Electroretinogram (ERG), Visual Evoked Potential (VEP), contrast Sensitivity, Color Vision, Visual Acuity, High luminance/High contrast Visual Acuity, Low luminance/High contrast Visual Acuity, Low luminance/Low contrast Visual Acuity, High luminance/Low contrast Visual Acuity, Opotype, vernier acuity, Reading Speed (high & low luminance), Glare Testing (cataract), Motion Perception, Metamorphopsia (late AMD), Shape and Texture discrimination for late-stage AMD, Mesopic and Scotopic Visual Fields, Photostress, Microperimetry (Fundus-guided Microperimetry) Tonometer, Stereopsis, Corneal Hysteresis, Fundus Retinal Imaging, Retinal Densitometry, Optical Coherence Tomography (OCT), Fluorescein Angiography, OCT Angiography (OCTA), Multi-spectral Imaging, Scanning Laser Ophthalmoscope, Anterior Segment OCT, Deep-field OCT, Retinal Metabolic Imaging, Ocular Blood Flow Imaging, Adaptive Optics, Autofluorescence, Non-mydriatic Fundus Camera, Optic Nerve Imaging, Ultrasound, Anterior Segment Photography, Slit Lamp, Pachymeter, and Interior Segment.

Further, the testing can comprise an audio module mounted to the frame for providing audio communication with the subject. The audio module can be in communication with the subject-instruction system for receiving subject instruction signals therefrom and converting the signals to audible signals for delivery to the subject. Further, the audio module can convert the subject instruction signals to one or more verbal commands for delivery to the subject. The verbal commands can be generated based on performance of the subject during the ophthalmic test.

In some embodiments, the testing device can be a head-wearable device. The head-wearable device can comprise a frame for mounting the device onto the subject's head. The automatic subject-instruction system is at least partially incorporated in the frame. Further, the automatic subject-instruction system can comprise: a processor, at least one random memory module (RAM), a permanent memory module, and a communication bus for providing communication between the processor, the RAM and the permanent memory module. The automatic subject-instruction system can further comprise a plurality of pre-recorded audio files containing subject instructions stored in the permanent memory module.

The device can further comprise a controller coupled to the frame for controlling one of more components of the ophthalmic diagnostic system. A display can be coupled to the frame and configured to be controlled by the controller. The controller can effect presentation of any of information, selection options and/or command options on the display. The information can comprise subject data and the selection options can allow a user to select right eye, left eye, or both eyes for administration of the ophthalmic diagnostic test. Further, the selection options can allow selecting a protocol for administering the ophthalmic diagnostic test. The selection options can also allow selecting a communication protocol for establishing communication between the device and another device. The display can also present software-controlled buttons for allowing a user to input data into the device.

Further, the device can comprise a communication module. The communication module can be configured to communicate with a command center. Specifically, the communication module is configured to communicate with the command center via a wireless protocol.

As noted, the light seal can comprise a conformable body having at least one opening adapted to be substantially aligned with the at least one eye of the subject when the light seal is worn by the subject. The conformable body can be configured for coupling to the frame of the head-wearable device such that a combination of the frame and the light seal isolates the at least one eye of the subject from ambient light. The device can further comprise an attachment element coupled to the conformable body for removably and replaceably coupling the light seal to a least a portion of the subject's head. The attachment element can comprise a strap and/or at least one arm coupled to the conformable body.

The light seal can comprise a hygienic liner configured for coupling with a surface of the conformable body so as to be in at least partial contact with the subject's skin. The hygienic liner is a single-use, disposable item and/or comprise a double-sided tape or an elastic material.

The head-wearable device can further comprise one or more light sensors coupled to the frame for detecting light leakage through the light seal. The one or more light sensors can be positioned so as to detect light leakage in vicinity of at least one eye of the subject. Further, the one or more light sensors comprise at least two light sensors each of which is positioned so as to detect light leakage in vicinity of one eye of the subject.

The head-wearable device can further comprise a mechanism for adjusting the light seal around the subject's head. The mechanism can comprises a ratchet mechanism coupled to the attachment element. The attachment element comprises a strap and the ratchet mechanism allows adjusting any of length of the strap and tension therein. A second strap can also be coupled to the frame for mounting the frame onto the subject's head. The head-wearable device can also comprise a quick release button coupled to any of the straps to allow facile release thereof.

The head-wearable device can further comprise an alert module in communication with the one or more light sensors for generating an alert signal in response to detection of light leakage above a predefined threshold by the one or more light sensors. The alert signal can comprise an audio signal.

The head-wearable frame can also comprises a frame body having a chamber for housing one or more components for performing the ophthalmic diagnostic test. The frame body is configured such that at least a portion thereof is positioned in front of the at least one eye when the head-wearable device is worn by the subject. Further, at least a portion of the frame body can be opaque so as to obstruct passage of ambient light to the at least one eye. The opaque portion can be hingedly coupled to another portion of the frame such that the opaque portion can be lifted so as to allow passage of ambient light to the at least one eye of the subject. Further, the at least a portion of the frame body can be formed of a material having an adjustable opacity in response to a stimulus. Additionally or alternatively, the at least a portion of the frame body can comprise a liquid crystal and a light polarizer for providing a transition from translucent to opaque upon application of a voltage thereto.

The head-wearable device can further comprise a slidable screen coupled to the frame, wherein the screen can be slidably positioned substantially in front of the at least one eye of the subject so as to obstruct passage of light thereto. The frame can comprise an opening configured to be substantially in front of the at least one eye of the subject when the device is worn by the subject, and further comprising a flip seal coupled to the opening to obstruct or to allow passage of ambient light to the at least one eye.

In some embodiments, the head-wearable device can comprise an optical system coupled to the frame for directing the test light into the at least one eye of the subject. The optical system can comprises a mirror for reflecting the test light emitted by the test light source into the subject's eye. The optical system can further comprise a lens for collimating and diffusing the light emitted by the light source. The head-wearable device can also comprise a movable platform on which the test light source is mounted. The movable platform can be movable along at least two orthogonal dimensions and/or along three orthogonal dimensions.

In some embodiments, the alignment mechanism can comprise an infrared light source mounted onto the frame for illuminating the at least one eye and an infrared detector mounted onto the frame for detecting at least a portion of the infrared light returning from the at least one eye in response to the infrared illumination. The head-wearable device can further comprise a feedback system mounted onto the frame and in communication with the infrared detector and the movable platform. The feedback system can be configured to detect the pupil of the at least one eye based on one or more signals generated by the infrared detector and cause movement of the platform to align the test light emitted by the at least one test light source with the subject's pupil. The infrared detector can comprise an infrared camera that is configured to generate an image of the subject's pupil based on the infrared light returning from the at least one eye of the subject. Further, the feedback system can be configured to align the test light emitted by the at least one test light source based on a shape of the subject's pupil in the image generated by the infrared camera. Moreover, the optical system can comprise a dichroic mirror adapted to reflect the test light from the at least one test light source onto the subject's pupil and further to allow passage of the infrared light returning from the subject's eye onto the infrared detector.

Other aspects and advantages of the invention can become apparent from the following drawings and description, all of which illustrate the various aspects of the invention, by way of example only.

BRIEF DESCRIPTION OF THE DRAWINGS

A detailed description of various embodiments is provided herein below with reference, by way of example, to the following drawings. It will be understood that the drawings are exemplary only and that all reference to the drawings is made for the purpose of illustration only, and is not intended to limit the scope of the embodiments described herein below in any way. For convenience, reference numerals may also be repeated (with or without an offset) throughout the figures to indicate analogous components or features.

FIG. 1A schematically illustrates an example of a head-wearable implementation of an ophthalmic testing, measurement, detection, and/or diagnosis system according to some embodiments disclosed herein.

FIG. 1FA schematically illustrates another light seal according to some embodiments disclosed herein.

FIG. 1FB schematically illustrates examples of light seals according to some embodiments disclosed herein.

FIG. 1G is a schematic illustration of a bottom view of a head-wearable implementation of an ophthalmic testing, measurement, detection, and/or diagnosis system according to some embodiments disclosed herein.

FIG. 2F schematically illustrates an example of an eye tracking mechanism according to some embodiments disclosed herein.

FIG. 3 is a high-level block diagram of digital electronic circuitry and hardware that can be used with, incorporated in, or fully or partially included in an ophthalmic testing and measurement system according to some embodiments disclosed herein.

FIG. 4A-1 is another high-level block diagram of an ophthalmic testing system according to some embodiments disclosed herein.

DETAILED DESCRIPTION

Figure 1C:
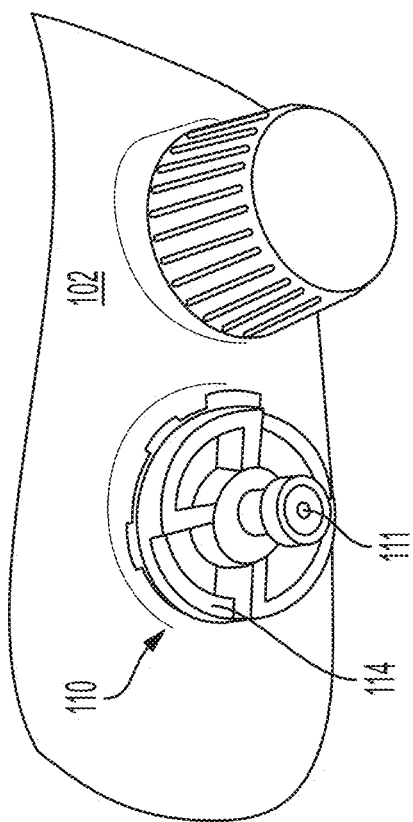
FIG. 1C schematically illustrates a portion of a head-wearable implementation of an ophthalmic testing, measurement, detection, and/or diagnosis system according to some embodiments disclosed herein.

The present disclosure relates to methods, systems, and corresponding apparatus for performing ophthalmic testing, measurement, detection, and/or diagnostic. The methods, systems, and apparatus disclosed herein can be used to perform various ophthalmic testing, measurement, detection, and/or diagnosis. For example, methods, systems, and apparatus disclosed herein can be used in performing testing and measurement directed at the detection and diagnosis of various ophthalmic conditions and diseases, such as age-related macular degeneration ("AMD," which is also known as age-related maculopathy "ARM"), vitamin A deficiency, Sorsby's Fundus Dystrophy, late autosomal dominant retinal degeneration, retinal impairment related to diabetes, diabetic retinopathy, retinitis pigmentosa.

FIG. 1A schematically illustrates an example of a head-wearable implementation 100 of an ophthalmic testing, measurement, detection, and/or diagnosis system (hereinafter "ophthalmic testing system") according to some embodiments disclosed herein. Although shown and described in the context of a head-wearable device, the ophthalmic testing systems described herein can be generally implemented in any suitable form or configuration. For example, at least a portion of the ophthalmic testing system described herein can be implemented in a head-wearable configuration 100 (hereinafter "head-wearable device") and/or in a tabletop implementation.

As noted, the head-wearable device 100 can be used to perform various ophthalmic tests and measurements on at least one eye of a test subject. For example, in some embodiments, the head-wearable device 100 can be used to perform ophthalmic tests directed to measuring the test subject's dark adaptation, in at least one eye of the test subject. Additionally or alternatively, the head-wearable device 100 can be used for concurrent or serial measurement and testing of both the subject's visual field and the subject's dark adaptation.

The term "dark adaptation," as used herein, refers to the adjustment of the eye to low light intensities or the recovery of light sensitivity by the retina in the dark after exposure to a bright light. Since the impairment of the rod photoreceptors can lead to impairment in dark adaptation, dark adaptation can be viewed as a bioassay of the health of the RPE, the Bruch's membrane, and the choriocapillaris. Therefore, an impaired dark adaptation can be used as a clinical marker of disease states that impair one or more of the rods, RPE, the Bruch's membrane, and the choriocapillaris. Such disease states include, but are not limited to age-related macular degeneration (AMD, which is also known as age-related maculopathy ARM), vitamin A deficiency, Sorsby's Fundus Dystrophy, late autosomal dominant retinal degeneration, retinal impairment related to diabetes, diabetic retinopathy, retinitis pigmentosa. Individuals with AMD can often have impaired dark adaptation as a result of the pathophysiology associated with AMD. In fact, deficits in dark adaptation appear to generally occur before clinical or structural manifestations of the disease state become evident. Therefore, measurements of dark adaptation can be useful in determining presence or an onset of this disease.

The term "visual field test" as used herein, refer to tests and eye examinations directed to detecting dysfunctions in the central and peripheral vision, which may be caused by medical conditions such as glaucoma, pituitary diseases, strokes, brain tumors, or other neurological issues.

Referring back to FIG. 1A, the head-wearable device 100 can comprise a headset 102 configured for placement adjacent to at least one eye of a test subject and a head-mount 103 configured to secure the headset 102 against at least a portion of a test subject's head. As detailed below, the headset 102 can be configured to host various components of one or more ophthalmic testing systems that can be used to perform at least one optical and/or ophthalmic test and/or measurement described herein.

The headset 102 can be configured such that it can be removably and replaceably coupled to the head-mount 103. The head-mount 103 can be configured for placement over the subject's head 102 such that, once coupled with the headset 102 and placed over the subject's head, at least one portion of the headset 102 is securely positioned in proximity of (e.g., in front of) of the subject's face and/or eyes.

Generally, the head-mount 103 can be implemented in any suitable manner. For example, as shown in FIG. 1A, in some embodiments, the head-mount 103 can comprise a rear portion 103R, a top portion 103T, and one or more side portions 103S, one or more side attachment mechanisms (e.g., straps) 104, a top extension 105, and one or more side connectors 106.

Figure 1B:
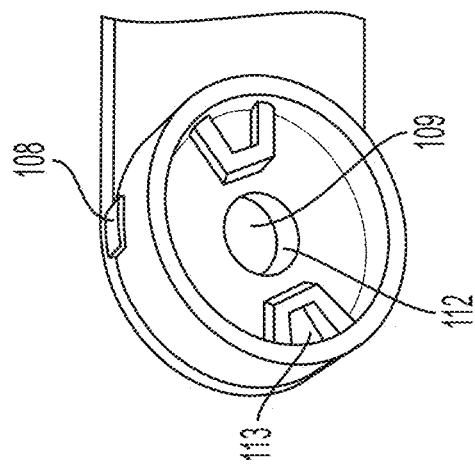
FIG. 1B schematically illustrates a portion of a head-wearable implementation of an ophthalmic testing, measurement, detection, and/or diagnosis system according to some embodiments disclosed herein.

The one or more side connectors 106 can be configured such that they couple the head-mount 103 to the headset 102. For example, as shown in FIGS. 1B-1C, the side connector 106 can comprise a head 108 having an internal receptacle 109 that is configured to mate with a mating feature 111 on the headset 102. The mating feature 111 can be disposed at any suitable position on the headset 102. For example, as illustrated in FIG. 1A, the mating feature 111 can be configured such that it extends out of a mating base 110 disposed on a side 102S of the headset 102.

The head 108 of the side connector 106 can comprise a spring loaded mechanism 112 that surrounds the receptacle 109. The spring loaded mechanism 112 can be coupled to a push button 107 (FIG. 1A), which can be used to engage and/or release the spring loaded mechanism 112. In operation, the head mount 103 can be coupled with the headset 102 via engagement of the mating feature 111 of the headset 102 with the spring loaded mechanism 112 in the receptacle 109 of the connector 106. The head mount 103 can be uncoupled from the headset 102 by activating the push button 107, thereby releasing the spring loaded mechanism 112 and disengaging the receptacle 109 from the mating feature 111.

The head-mount 103 can be adjustable to accommodate various subject head sizes/hair styles. For example, as shown in FIG. 1A, the head-mount 103 can comprise a ratchet 113 that connects to the one or more side straps 104 and is configured to adjust the length of the one or more straps 104. In some embodiments, the ratchet 113 can be configured as a dial that can be used to extend and/or reduce the length of the strap (e.g., extend the strap 104 by rotating the ratchet 113 in a counter clock-wise direction and reduce the length of the strap by rotating the ratchet in a clock-wise direction). This configuration allows the head-mount to be adjusted to the subject's head to ensure that at least a portion of the headset 102 is securely positioned against at least a portion of the subject's face and/or eye.

Additionally or alternatively, the head-mount 103 can be adjusted against a subject's head using an adjustable connector 105 that is configured to further ensure secure placement of the headset 102 against at least a portion of the subject's face and/or eye. As shown in FIG. 1A, the adjustable connector 105 can be configured such that it extends out of the top portion 103T of the head-mount 103 and is coupled to a bracket 114 on the headset 102. In some embodiments, the adjustable connector 105 connector can be configured to thread through and loop around the bracket 114 disposed on the top surface 102T of the headset 102. Generally, any suitable mechanism available in the art can be used to thread and secure the adjustable connector 105. For example, as shown in FIG. 1A, the adjustable connector 105 can comprise a tab 115 that can be used to facilitate threading the adjustable connector 105 through the bracket 114. Once threaded through the bracket 114, the length of the adjustable connector 105 can be adjusted to secure the headset 102 and the head-mount 103 against the subject's head (e.g., by pulling and/or releasing of the connector 105). Further, once looped over the bracket 114, the adjustable connector 105 can be secured using any suitable technique known in the art. For example, in one embodiment, the adjustable connector 105 can be secured against itself using means such as a hock-and-loop connector or Velcro®.

Further, as shown in FIGS. 1B-1C, the head-mount 103 can be rotatably coupled to the headset 102. Specifically, the one or more side connectors 106 that couple the head-mount 103 to the headset 102 can be configured such that they rotatably connect to the mating base 110 of the headset 102. For example, in some embodiments, the mating feature 111 can be coupled with the receptacle 109 such that once coupled with the receptacle 109, the head-mount 103 is rotatably connected to the headset and can rotate about the mating feature 111. The head-mount 103 can be configured to rotate about the headset 102 at any suitable angle. For example, the head-mount 103 can be configured to rotate about the headset 102 at approximately about 5°, 10°, 15°, 20°, 25°, 30°, 35°, 40°, 45°, 50°, 55°, 60°, 65°, 70°, 75°, 80°, 85°, and/or 90°.

Moreover, to accommodate hygienic use with multiple test subjects, the head-mount 103 can include a hygienic layer 116. The hygienic layer 116 can be configured such that it covers at least a portion of an interior surface of the head-mount 103, where the head-mount 103 is expected to come in contact with the subject's head and/or skin. The hygienic layer 116 can be removably and/or replaceably coupled to the at least one portion of the interior surface of the head-mount. For example, the hygienic layer 116 can be configured such that it can be removably and replaceably coupled to the interior surface using a Velcro® connector. The hygienic layer 116 can comprise any suitable material available in the art. For example, in some embodiments, the hygienic layer 116 can comprise a medical-grade silicone that can be cleaned (e.g., using a medical grade cleaner) before/after use.

Referring back to FIG. 1A, the headset 102 can comprise a front face 117. The front face 117 can comprise a display 117 (e.g., an interactive display). The headset 102 can further comprise one or more dials 118 intended for use in adjusting a viewing distance of an image plane provided by the headset, as well as an input/output port 119. Additional details regarding the components of the headset 102, the display 117, and the one or more dials 118 are provided below.

The input/output port 119, as detailed below, can couple the headset 102 to one or more external tools (not shown) via a wired connection. As shown in FIG. 1A, the head-mount 103 can further comprise a holder 120 that is configured to receive at least a portion of the wire 121 connected to the input/output port 119. By receiving the at least one portion of the wire 121, the holder 120 can function to secure the wire away from the subject's body during an ophthalmic test/screening.

Figure 1D:
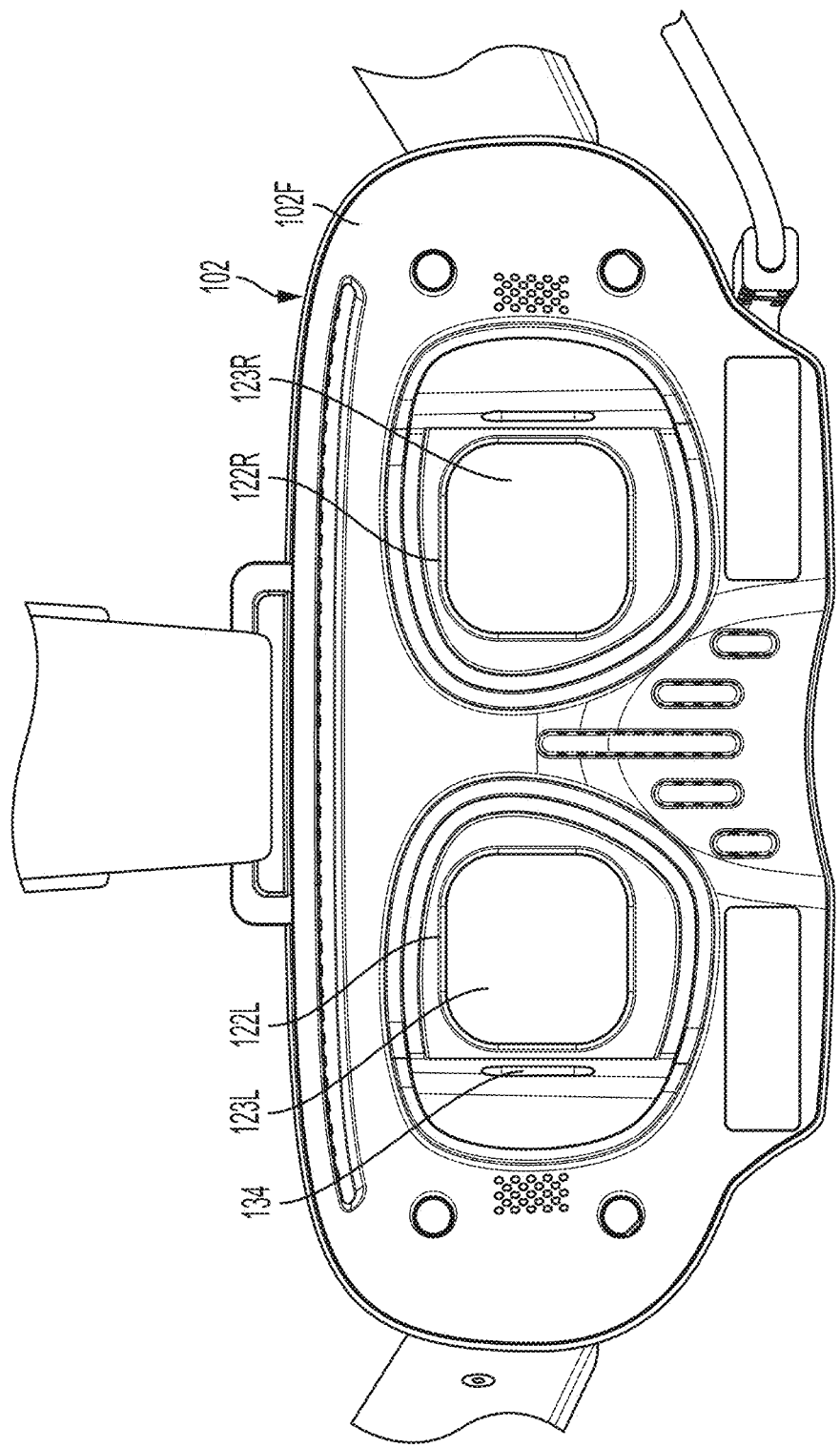
FIG. 1D depicts an illustration of a portion of a head-wearable device according to some embodiments disclosed herein.

FIG. 1D depicts an illustration of a portion of a head-wearable device according to embodiments disclosed herein. As shown in FIG. 1D, the headset 102 can comprise an internal surface 102f that is configured to be at least partially positioned against the face and/or head of the test subject. The internal surface 102f can comprise one or more optical interfaces 122R, 122L, each configured to optically couple at least one eye of a test subject with the head-wearable device 100 (e.g., each configured to receive at least one eye of the test subject). Each optical interface 122R, 122L can be configured such that it can substantially align with at least one eye of the test subject. Although shown as having two optical interfaces 122R, 122L, each configured to couple/interact with one eye of the test subject, the headset 102 can include any suitable number of optical interfaces. Further, each optical interface 122R, 122L can be configured to receive one eye and/or both eyes of the test subject.

The optical interfaces 122R, 122L can comprise any suitable material. For example, the interfaces 122R, 122L can each comprise an optically transparent window 123R, 123L through which the subject's eye(s) can interact with the optical components included in the headset 102.

Figure 1E:
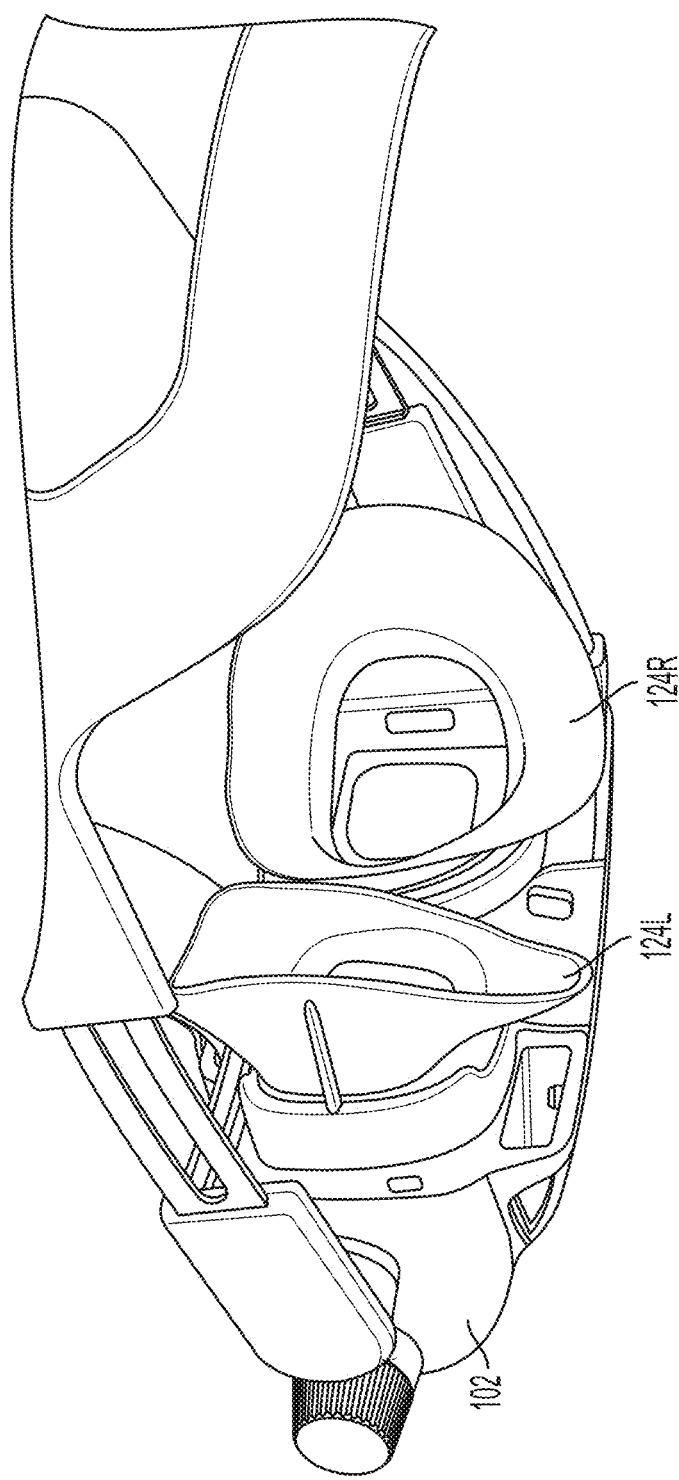
FIG. 1E schematically illustrates a portion of a head-wearable device having a light seal.
Figure 1F:
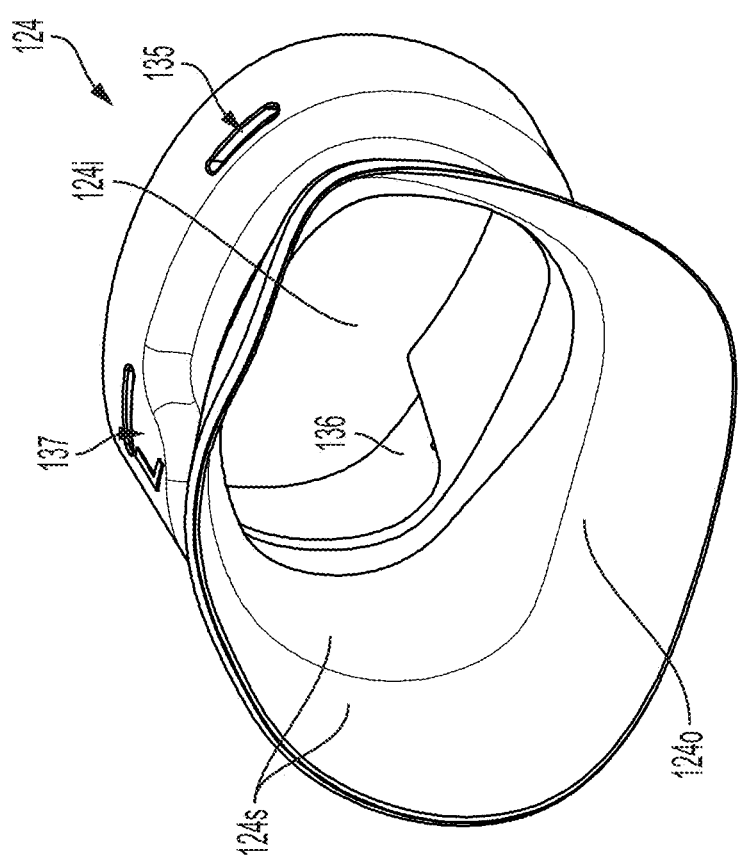
FIG. 1F schematically illustrates a light seal according to some embodiments disclosed herein.
Figure 1F:
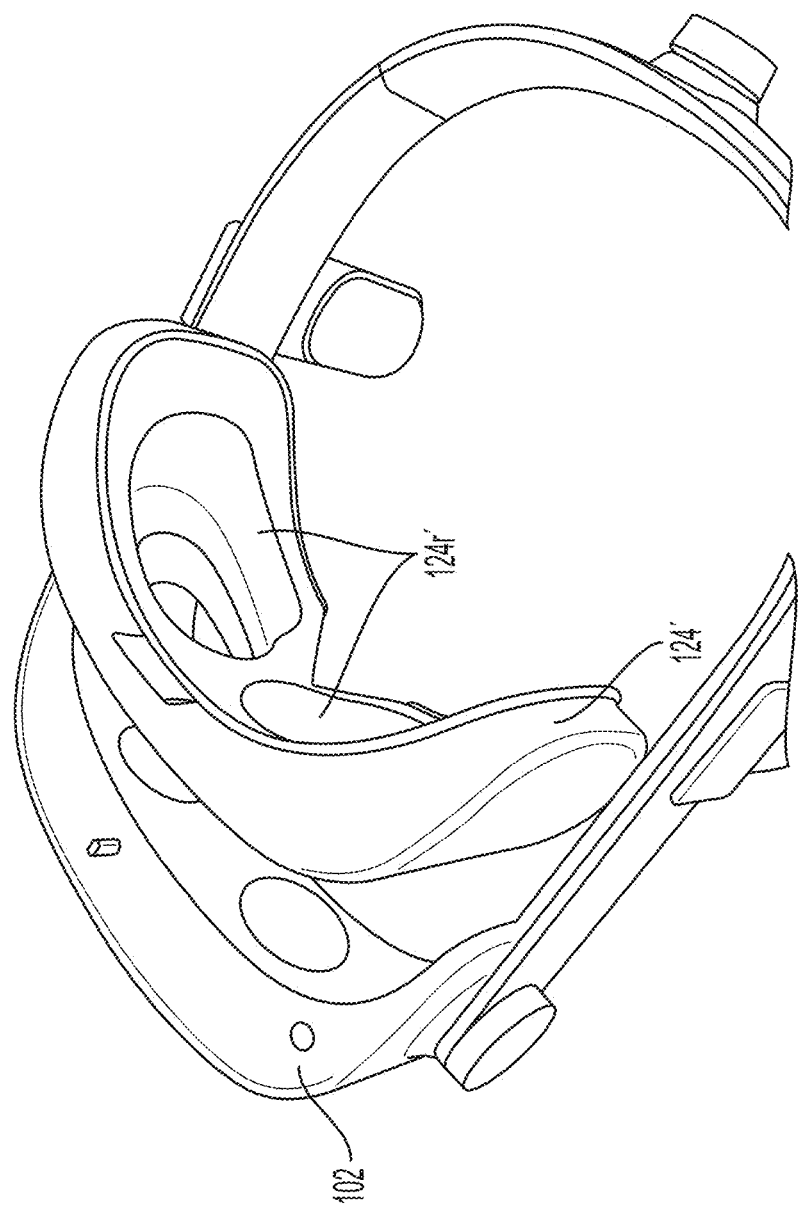
Figure 1F:
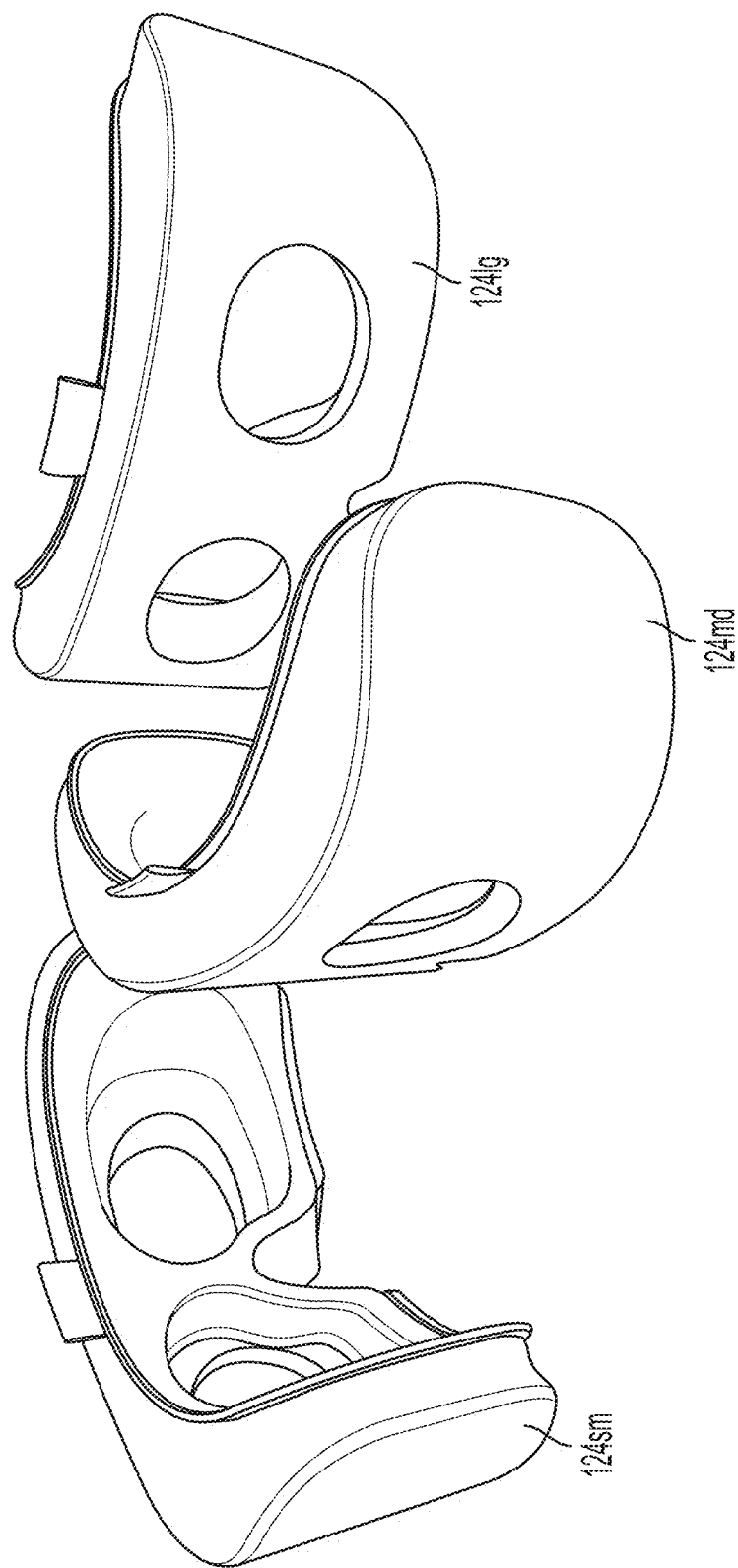

Referring now to FIGS. 1E-1F, the headset 102 can comprise one or more light seals 124R, 124L configured to isolate the optical interface 122R, 122L and at least one eye (e.g., a test eye) of the subject from ambient light. Such isolation of the subject's eye(s) from the ambient light can be important in measurements of dark adaptation and also in performing various other ophthalmic tests and measurements, such as detection of vitamin A deficiency, Sorsby's Fundus Dystrophy, late autosomal dominant retinal degeneration, retinal impairment related to diabetes, diabetic retinopathy, drug induced retinal toxicity, glaucoma, ocular hypertension, retinal hypoxia, retinitis pigmentosa, and fundus albipunctatus.

The light seals 124R, 124L can comprise any suitable shape and material available in the art. For example, in some embodiments, the light seal 124R, 124L can comprise a cup-shaped configuration (for example, as shown in FIG. 1F) that is coupled to the interface 122R, 122L and configured to receive/couple/interact with the eye of the test subject and/or seal the eye from ambient light.

Although shown as having two separate seals for each eye of the test subject, the light seal 124R, 124L can be configured such that it can isolate one or both eyes of the subject from ambient light. Specifically, the light seal 124R, 124L can be configured such that it can independently isolate each eye or both eyes of the subject from ambient light (e.g., can provide same and/or a different, separate, or independent light seal for each eye).

Generally, the light seal 124R, 124L can be configured according to any suitable technique and/or using any suitable materials available in the art informed by the present teachings. For example, the light seal 124R, 124L can be configured such that it is substantially conformable to at least a portion of the subject's head, face, and/or the area surrounding a subject's eye(s). Specifically, as shown in FIG. 1F, the light seal 124 can comprise a first opening 124*i* that is configured to surround an interface 122R, 122L on the headset 102 and a second opening 124*o* that is configured to substantially aligned with at least one eye of the subject when the headset 102 is placed against the subject's eye(s). The second opening 124*o* can comprise a conformable body that is configured to conform to the subject's skin and face (e.g., as it is pressed against the subjects face,) to seal ambient light from entering the eye(s) of the subject.

In some embodiments, the light seal 124 can comprise one or more sensors 124*s* configured to monitor proper and/or effective usage of the light seal 124. The one or more sensors 124*s* can generally comprise any suitable sensor. For example, the one or more sensors 124*s* can comprise one or more light sensors that are configured to measure and/or detect the amount of ambient light leaking through the light seal 124 when it is coupled to the subject's eye so as to seal the subjects eye from ambient light. The one or more light sensors 124*s* can also be configured to measure the intensity of such detected light leakage. The one or more light sensors 124*s* can be positioned at any suitable position on the light seal. For example, as shown in FIG. 1F, in some embodiments, the light sensors 124*s* can be positioned in the vicinity of at least one eye of a subject when the head-wearable device 100 and the light seal 124 are worn by the subject.

Additionally or alternatively, the one or more sensors 124*s* can comprise at least one of: a pressure sensor and a capacitive touch sensor that are disposed in one or more facial contact points. Such pressure sensor and capacitive touch sensors can be used to ensure that the device is placed against the subject's body (e.g., face) correctly, and ensure proper placement of the device and/or the light seal against the subject's body, face, or skin.

Referring back to FIG. 1D, the headset 102 can include one or more coupling features 134 for coupling the headset 102 to the light seal 124. Specifically, as shown in FIG. 1D, the internal surface 102*f* of the headset 102 can comprise one or more features 134 that are configured to connect to corresponding mating features 135, 136, 137 on the light seal 124 (FIG. 1E-1F). Generally, the light seal 190 can be attached to the frame 102 using any suitable means. For example, the light seal 190 can be inserted within a receptacle provided in the frame, glued to the frame, or attached to the frame using other suitable means of coupling.

Although shown as being separate from the headset 102, at least one portion of the light seal 124 can be directly and/or fixedly coupled to the headset 102 of the head-wearable device 100 and/or be an integral part of the headset 102.

Further, although described as being used with a disposable and removable cover, the light seal can comprise any suitable material, for example a material capable of being cleaned with standard and commonly known and available suitable medical cleaners before and/or after use with each subject. Additionally or alternatively, the entire light seal can be disposable and/or replaceable before and/or after use with each subject. For example, as shown in FIG. 1FA, in some embodiments, the light seal 124' can comprise a single-piece light seal having one or more receptacles 124*r'*, each configured to receive at least one eye of the test subject. Further, as shown in FIG. 1FB, the light seal can be provided in one or more sizes 124*sm*, 124*md*, 124*lg*, for example in sizes small, medium, and large, to accommodate different face sizes and shapes.

Moreover, the light seal 124 can comprise one or more portions and/or elements, each of which can be reusable and/or disposable. For example, as shown in FIG. 1G, the light seal 124 can comprise a hygienic cover 125 configured to cover the portion of the light seal that comes in contact with a test subject's skin. The cover 125 can be configured such that it can be removably and replaceably coupled to the light seal 124 such that it can be replaced after use with each test subject. The cover 125 can be a disposable, removable, and/or replaceable layer and can comprise any suitable material in the art. For example, the cover 125 can comprise cotton. Additionally or alternatively, the hygienic cover 125 can comprise a layer of tape (e.g., double-sided tape).

In some embodiments, the cover 125 can comprise a radio frequency identification (RFID) tag or a barcode 126 configured to track proper use of the head-wearable device 100 and/or asset tracking. The RFID tag 126 can comprise any suitable tag known in the art. The RFID tag 126 can be incorporated in and coupled to the light seal 125 and/or the light seal cover 126 in any suitable known manner. For example, as shown in FIG. 1E, the RFID tag 126 can be incorporated in the disposable cover 125 to ensure that the disposable cover 125 is an authentic disposable.

Further, the RFID tag 126 can be configured to enforce single usage of the disposable cover 125. For example, the head-wearable device 100 and the RFID tag 126 can be a passive tag having a factory assigned serial number that is configured to provide information to an RFID reader 127 positioned on the headset 102. In operation, the headset 102 can be configured such that the operation of the headset 102 and the performance of an ophthalmic test via the headset 120 can only be initialized once the RFID tag 126 is brought in the vicinity of the RFID reader 127 to activate the RFID reader 127. This can ensure that a disposable cover 125 provided by the original manufacturer is used every time the head-wearable device 100 is used to conduct an ophthalmic test. Further, in order to ensure single-usage of the cover 125, the system 100 can be configured such that optical test results provided by the device are only displayed/provided once the RFID tag 126 is scanned against the RFID reader 127 for a second time.

Figure 1H:
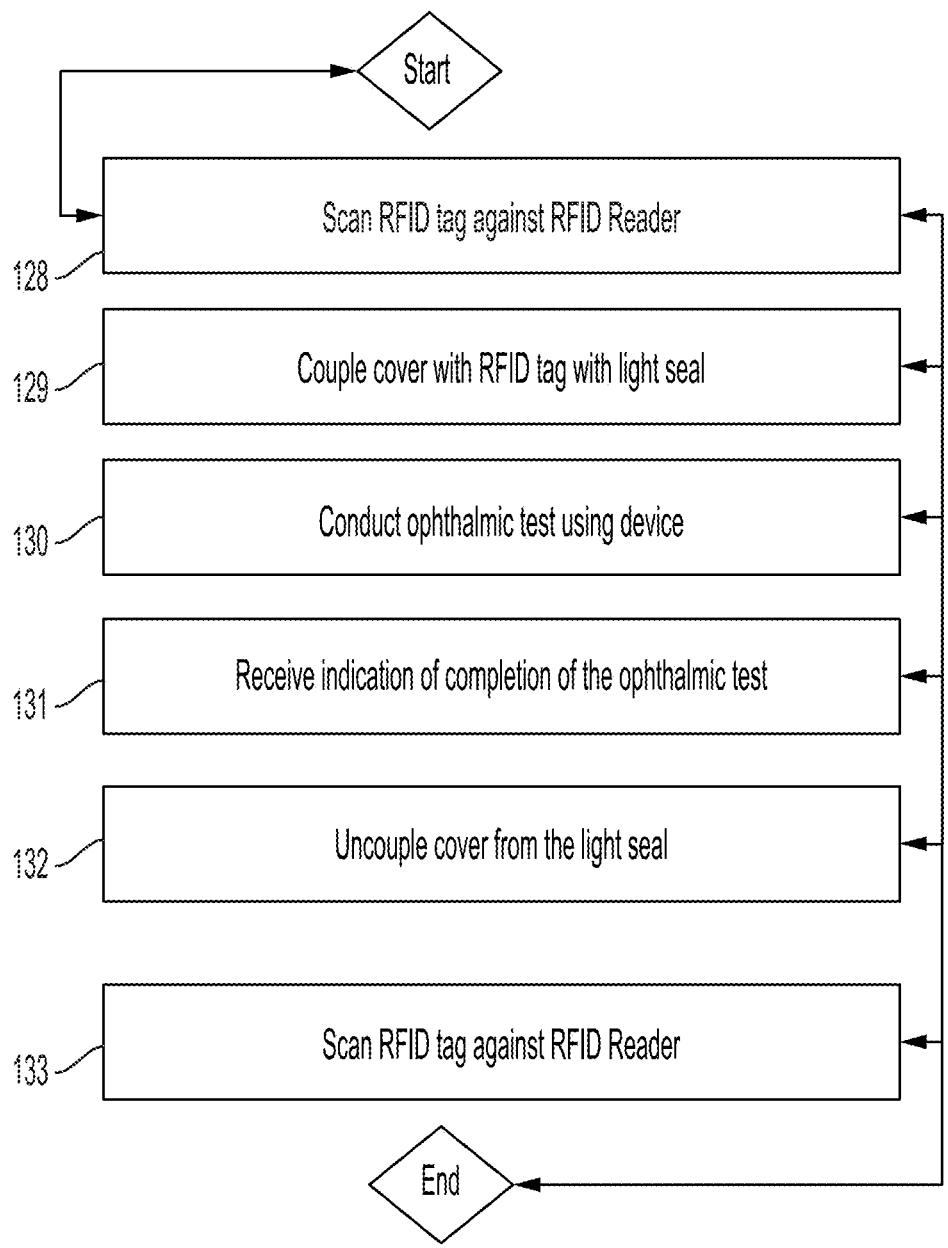
FIG. 1H illustrates an example of procedures that can be used for ensuring single usage of a cover for a light seal according to some embodiments disclosed herein.

FIG. 1H illustrates an example of procedures that can be used for ensuring single usage of a cover 125 according to some embodiments disclosed herein. As shown in FIG. 1H, an ophthalmic test and/or measurement using the head-wearable device 100 can be initiated (box 128) by scanning an RFID tag 126 of a disposable cover 125 against an RFID reader 127 of the head-wearable device 100. Once the test is initialized, the cover 125 (having the RFID tag 126) is coupled with the light seal 124 (box 129). The head-wearable device 100 can then be used for conducting an optical test and/or measurement (box 130). For example, the head wearable device can be placed against the head and/or face of the test subject to conduct the ophthalmic test and measurement and/or the eye of the test subject can be brought into contact with an optical interface of ophthalmic testing system and coupled to the light seal 124 and the cover 125. Upon receiving a confirmation of the completion of the test (explained in more details below, box 131), the cover 125 can be uncoupled from the light seal 125 (box 132). Once removed from the light seal 124, the RFID tag 126 on the cover 125 is scanned against the RFID reader 127 (box 133). As explained in further details below, the scanning of the RFID tag 126 against the RFID reader 127 causes the head-wearable device 100 to display the results of the ophthalmic test at hand on a display 117 of the head-wearable device 100.

Figure 1I:
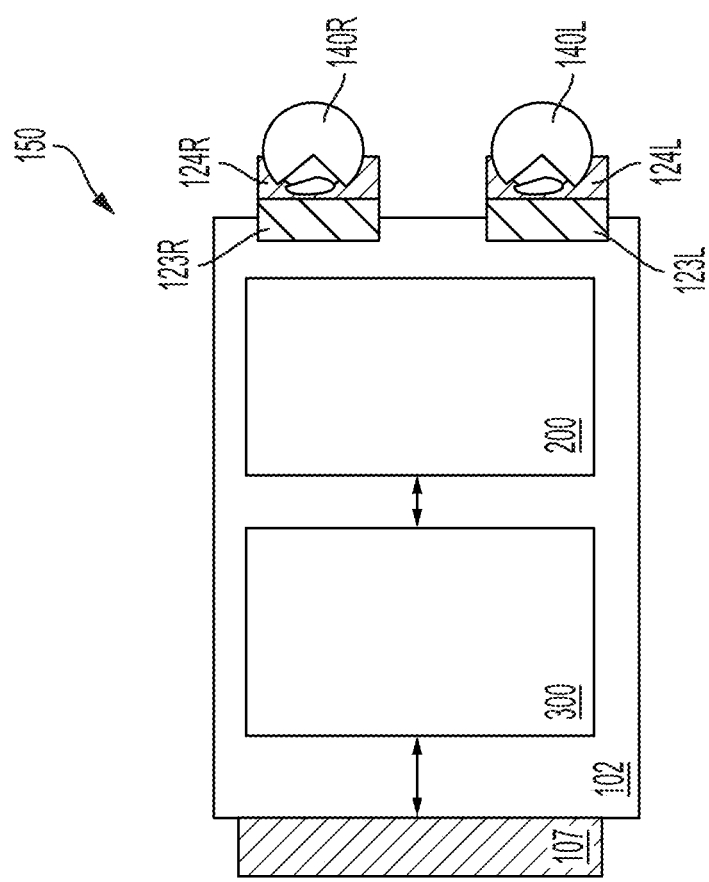
FIG. 1I is a high-level block diagram of an ophthalmic testing system according to some embodiments disclosed herein.

FIG. 1I is a high-level block diagram of an ophthalmic testing system 150 according to embodiments disclosed herein. As noted, embodiments disclosed herein can be implemented in the form of a table-top system and/or in a head-wearable device (for example, as shown in FIG. 1A). When implemented in a head-wearable device, the ophthalmic testing system is implemented in the headset 102 of the head-wearable device. Although described in the context of a head-wearable device, it should be understood that the embodiments disclosed herein can be implemented as a table-top system.

As shown in FIG. 1I and described above, the headset 102 of the head-wearable system can comprise one or more receptacles 123R, 123L, each configured to receive at least one eye 140R, 140L of a test subject. As explained with reference to FIG. 1E, each receptacle 123R, 123L can be coupled with a corresponding light seal 124R, 124L that is configured to obstruct passage of ambient light to the subject's eye(s) 140R, 140L.

As described in further details below, the headset 102 can also include a display 107, an optical system 200 that comprises optical components for conducting various ophthalmic tests and measurements with the embodiments disclosed herein, and digital electronic circuitry and hardware 300 that can be used with, incorporated in, or fully or partially included in an ophthalmic testing and measurement system 150 according to the embodiments disclosed herein.

Figure 2A:
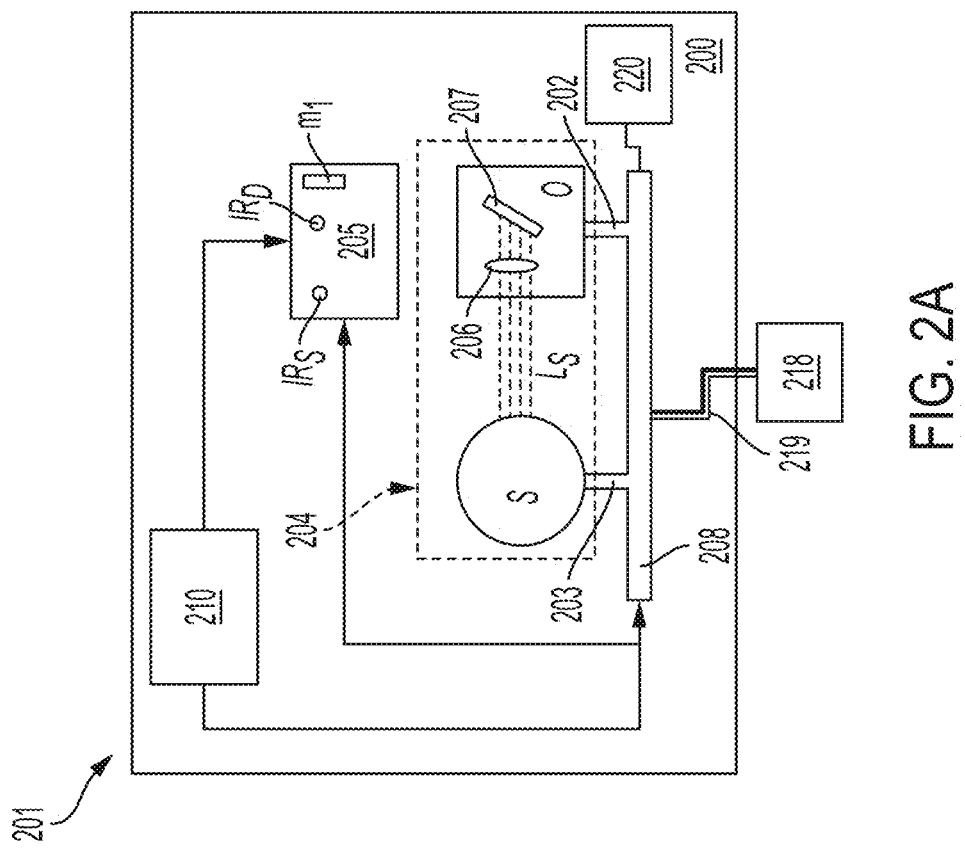
FIG. 2A is a high-level block diagram of an optical system according to some embodiments disclosed herein.

FIG. 2A is a high-level block diagram of an optical system 200 according to embodiments disclosed herein. In the example shown in FIG. 2A, the optical system 200 is shown as having a housing 201 that houses the components of the optical system. However, it should be understood that the optical system 200 need not to have a housing and the various components of the optical system can be disposed within the headset 102 or the housing of a tabletop device.

The optical system 200 can generally comprise one or more light sources (collectively shown as light source S) that are configured to emit one or more beams of light $L_s$ at one or more wavelengths. The light source S can be any suitable light source known and/or available in the art. For example, the light source can be a laser, a light-emitting diode (LED), an organic light-emitting diode (OLED), or a liquid crystal display (LCD) light source. Further, the light source can be a single-mode or a multi-mode light source configured to emit light beams at one or more wavelengths. For example, the light source can be a broad spectrum light source, having one or more filters or other suitable optics, which is configured to emit light beams at any desired wavelength. One skilled in the art should appreciate that the optical system 200 can include any suitable number of light sources.

In some embodiments, the light source S can be configured to generate a stimulus light having a spectrum effective in stimulating the rod-shaped photoreceptors of a subject's eye. By way of example, the stimulus light can have one or more wavelengths in a range of about 400 nm to about 570 nm. In some embodiments, the stimulus light source can be configured to generate stimulus light beams having a duration in a range of about 100 milliseconds to about 400 milliseconds.

As noted in U.S. Pat. No. 8,795,191, the entirety of which is incorporated herein by reference, a subject's ability to dark adapt can be characterized by measuring scotopic sensitivity recovery (i.e., rod function) after photobleaching using psychophysical testing methods known in the art. In such psychophysical tests, typically a test eye of the subject is first pre-conditioned to a state of relative scotopic insensitivity by exposing the eye to a conditioning light (a procedure referred to as "photobleaching" or "bleaching"). After this pre-conditioning (or bleaching), the subject's scotopic sensitivity (or the minimum light intensity that can be detected in a dark environment) is measured at one or more successive times. The measurement can be made by exposing the bleached region of the test eye to a series of stimulus lights of varying intensities. Based on subject feedback as to which stimulus intensities can be detected, a sensitivity, or threshold, is determined for each successive time. The subject is kept in a dark environment throughout the test. The absolute levels and/or kinetics of the resulting threshold curve indicate the subject's ability to dark adapt. Impairment in the subject's dark adaptation parameters may indicate the subject is currently suffering from and/or at risk for a disease state that impairs one or more of the rod and/or cone photoreceptors, the RPE, the Bruch's membrane and the choriocapillaris.

Referring back to FIG. 2A, the light source S can be configured to emit the light beams at one or more predetermined time periods and/or for one or more predetermined time frames. For example, the light source S can be configured to emit light beams configured to stimulate a subject's eye every 1 to 5 seconds or every 2 to 3 seconds. The stimulus light can have an intensity in a range of about 4 $cd/m^2$ to about 4.85 $cd/m^2$, a range of 4 $cd/m^2$ to about 5 $cd/m^2$, a range of about $5\times10^{-5}$ to about 5 $cd/m^2$, a range of about $4.0\times10^{-5}$ $cd/m^2$ to about 5 $cd/m^2$, a range of about $4.0\times10^{-5}$ $cd/m^2$ to about 4 $cd/m^2$, or a range of about $4.0\times10^{-5}$ $cd/m^2$ to about 5 $cd/m^2$.

Additionally or alternatively, the light source S can be configured to generate a bleaching light capable of bleaching photopigments and/or desensitizing a portion of the rhodopsin molecules in a test eye of a subject. For example, the light source S can be configured to emit light beams having one or more wavelengths in a range of about 490 nm to about 510 nm or in a range of about 600 nm to about 700 nm. Further, the light source S can be configured to generate the bleaching light pulses at one or more predetermined time periods and/or for one or more predetermined time frames. For example, the light source S can be configured to emit bleaching light beams having a duration in a range of about 0.5 milliseconds to about 200 milliseconds. Further, the light source S can generate bleaching light beams having one or more intensities. For example, the bleaching light beams can comprise an intensity in a range of about 1.5 log Scotopic Trolands/sec to about 8 log Scotopic Trolands/sec and/or an intensity in a range of about 3 log Scotopic Trolands/sec to about 5 log Scotopic Trolands/sec.

The light source(s) S can also be configured to generate fixation light beams configured to direct the subject's attention at the bleaching or stimulus light (e.g., the light source generating the bleaching and/or stimulus light). In some embodiments, the optical system 200 can be configured to present the subject with a fixation dot 210, where the subject is asked to fixate his/her gaze at least at some point during the ophthalmic test. The fixation light beams can be configured to emit visible light at a wavelength (e.g., in a range of about 605 nm and about 655 nm) and at a desired light intensity (e.g., in a range of from about 1. mlux to about 100. mlux, from about 1. mlux to about 80. mlux, from about 1. mlux to about 460. mlux, or from about 1.47 mlux to 57.6 mlux, depending on pupil size) configured to focus the subject's gaze. Further, although described as a single light source S, the optical system 200 can include two or more light sources S. For example, the optical system 100 can include a light source configured to emit bleaching light beams and another light source configured to emit the stimulus light beams.

As noted above, the light source(s) S can generally be any suitable light source available in the art. For example, the light source(s) S can comprise an LED light source, an OLED light source, and/or an LCD light source. The LED, OLED, and/or LCD light sources can be used for generating at least one of the stimulus and bleaching lights.

Figure 2C:
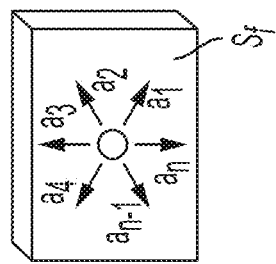
FIG. 2C schematically illustrates an example of a light source according to some embodiments disclosed herein.
Figure 2E:
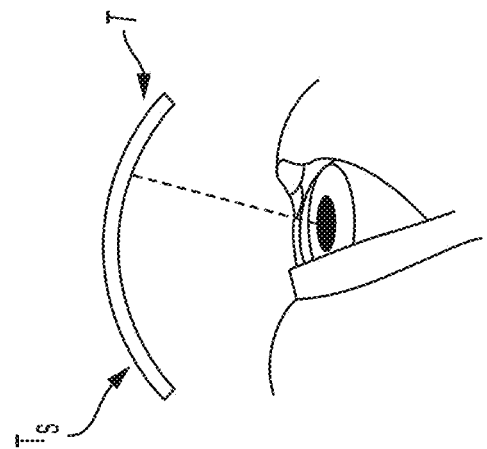
FIG. 2E schematically illustrates yet another example of a light source according to some embodiments disclosed herein.
Figure 2B:
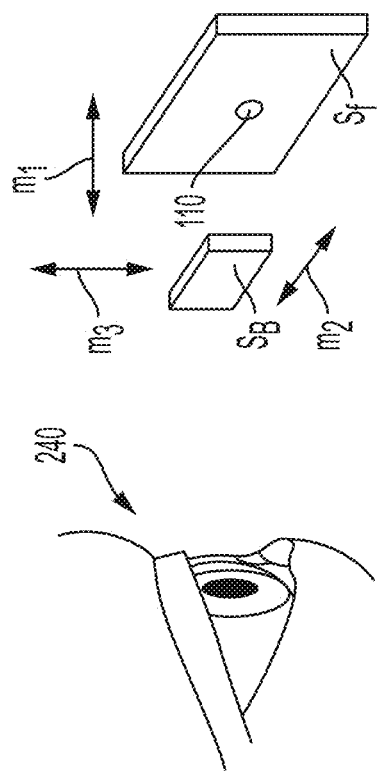
FIG. 2B schematically illustrates examples of light sources according to some embodiments disclosed herein.

For example, as shown in FIG. 2B, at least one LED, OLED, and/or LCD light source Sf and/or at least one LED, OLED, and/or LCD pixel light source Sf can be used to generate the fixation and/or the stimulus lights. Additionally or alternatively, at least one other one LED, OLED, and/or LCD light source SB can be used to deliver the bleaching light. The LED, OLED, and/or LCD light sources, when used as a bleaching light source SB can allow for real-time tracking of the subject's eye 240 and, thereby, correct for possible movements of a subject's eye/pupil (due to wandering eyes) within predetermined limits. Similarly, when used to provide fixation and stimulus light, such light sources (e.g., light source Sf) can provide for real-time alignment of the light source to a subject's eyes.

Specifically, such sources $S_B$, Sf can allow for adjustment of the intensity of the stimulus light provided to the subject's eyes (e.g., using cosine correction techniques) to ensure that appropriate stimulus light levels are directed at the eye, regardless of the angle of alignment between an LED/OLED/LCD pixel source and the subject's eye.

In some embodiments, the angle of alignment between an LED/OLED/LCD pixel source and the subject's eye can be adjusted mechanically. For example, in some implementations, the knob or dial (e.g., dial 118) can be used to manually adjust a fixation light source $S_f$ in the direction shown by arrow $m_1$. Specifically, the dial 118 can be connected to the fixation source $S_f$ and configured to move the fixation source in an axial direction relative to the subject's eye(s). By moving the fixation source $S_f$ relative to the subject's eye(s), the dial 118 can bring the fixation source $S_f$ in focus and/or compensate for possible reflective errors (e.g., nearsightedness (myopia), farsightedness (hyperopia), astigmatism or presbyopia) in the subject's eyes. The dial 118 can be configured such that it can be adjusted by the test subject and/or by the technician/clinician delivering the ophthalmic test to the subject.

Alternatively or additionally, the alignment between the LED/OLED/LCD pixel source and the subject's eye can be achieved automatically. For example, in some implementations, a pupil tracking mechanism can be employed to detect the location and/or size of a subject's pupil. As described in further details below, a processor (e.g., included in the digital electronic circuitry and hardware 300) can receive the detected pupil location and instruct the relevant components of the optical system 200 to bring the LED/OLED/LCD pixel sources in alignment with the subject's eye. Once achieved, such alignment can reduce the amount of cosine correction necessary to ensure proper stimulus intensity due to, for example, a subject with a wandering eye.

Further, in some implementation, the fixation light source Sf can be configured such that it can be automatically adjusted. For example, as explained in further details below, the fixation light source Sf can be configured such that it is controlled by a processor (e.g., included in the digital electronic circuitry and hardware 300) that adjusts and focuses the fixation light in response to receiving a response from the test subject. For example, as detailed below, the processor can be configured to receive a response, indicating whether the subject can clearly view the fixation light and/or the fixation dot 210 and, in response, adjust the position of the fixation light source Sf to bring the fixation light in focus for the subject.

Similarly, the LED, OLED, and/or LCD light sources, when used as a bleaching light source SB, can be configured to move (e.g., in response to feedback signals provided by an eye-tracking mechanism, as detailed below with reference to FIG. 2A), in line with the subject's eye, to achieve alignment with the subject's eye(s). For example, in some embodiments, the bleaching light source SB can be moved in line with the subject's eye through two-dimensional movements in the X-Y plane. Specifically, as shown in FIG. 2B, the bleaching light source SB can be configured to move, in the direction shown by arrow m2 and/or in the direction shown by arrow m3, in front of the source that generates the stimulus and fixation lights Sf. This configuration allows the bleaching light source SB to provide the light beams required to bleach the photoreceptors in the subject's eye(s). Once the bleaching sequence duration is complete, the bleaching source SB can move in order to allow exposure of the subject's eye to the fixation and/or stimulus lights emitted by the fixation and/or stimulus light source(s) Sf.

The fixation and stimulus LED, OLED, and/or LCD light source screens can move in connection with real-time eye tracking. Specifically, the fixation and/or stimulus light source(s) Sf can be configured such that they move, in response to information received from a real-time eye tracking mechanism (e.g., a pupil tracking mechanism) to follow the location of a subject's eye/pupil. As shown in FIG. 2C, the LED, OLED, and/or LCD light source screens can move in any number of positions within the XY plane, for example in the directions shown using arrows a1, a2, a3, a4, . . . , an−1, an, where n is a finite number.

Figure 2D:
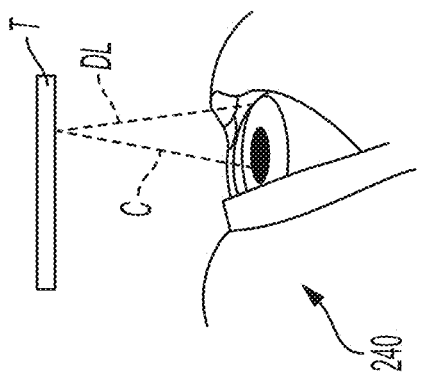
FIG. 2D schematically illustrates another example of a light source according to some embodiments disclosed herein.

FIG. 2D schematically illustrates the manner in which a subject's eye can be exposed to an LED, OLED, and/or LCD light source screen. As shown, the screen T of a light source Sf can be positioned in front of the subject's eye to provide the subject's eye 240 with a direct line of light DL (e.g., a direct line of stimulus light). FIG. 2D also illustrates the cosine angle C for correcting stimulus intensity according to the degree of misalignment of the subject's eye relative to the light source. As noted above, cosine correction techniques can be used to ensure that appropriate stimulus light levels are directed at the eye, regardless of the angle of alignment between an LED/OLED/LCD pixel source and the subject's eye.

Further, as shown in FIG. 2E, the curvature of the LED, OLED, and/or LCD light source screen T can be used to accommodate eye wander with less correction for intensity. Specifically, as shown in FIG. 2E, a concave spherically-curved OLED screen Ts with its center point aligned at the eye/pupil of the subject, can be used to accommodate eye wander without a need to correct for intensity. The concave spherically-curved OLED screen Ts ensures that the subject's gaze is aligned and remains within the coverage range of the beams emitted by the OLED screen Ts, thereby ensuring that appropriate amounts of light are directed at the subject's eye at all times.

Referring back to FIG. 2A, the optical system 200 can further comprise one or more optical components (collectively referenced using reference character O) that are configured to direct the light beams emitted by the light source S to the subject's eye 240. The optical components can be configured such that they direct the light beams emitted by the light source S to any suitable portion of the subject's eye, for example the pupil and/or the retina of at least one eye 240 of the test subject.

The optical components O can generally include any suitable optical elements available in the art. For example, the optical components O can comprise at least one lens 206 that is optically coupled to the light source S and configured to collimate the light beams emitted by the light source S. The lens 206 can comprise at least one aspheric lens 206 adapted to correct for spherical aberration.

Additionally or alternatively, the optical components O can include one or more mirrors 207 that are configured to redirect the light beams emitted by the light source S as needed. For example, the one or more mirrors 207 can be configured to direct the light emitted by the test light source onto a test subject's eye. The one or more mirrors 207 can comprise at least one dichroic mirror that is configured to reflect the light from the test light source S onto the subject's pupil and allow passage of the light returning from the subject's eye into the optical system 200. As detailed below, the light source S can comprise an infrared light source configured to illuminate at least one eye of the subject. The one or more mirrors 207 can comprise at least one dichroic mirror that is configured to reflect the light from the infrared light source onto the subject's pupil and allow passage of the light returning from the subject's eye into the optical system 200 and an infrared light detector $IR_D$ (discussed below). By way of example, the infrared light can have a wavelength of greater than about 700 nanometers.

In some embodiments, the light source S and/or the optical components O can be housed in a sealed package 204. The sealed package 204 can be an integral part of the optical system 200 or can be configured such that it is removably and replaceably mounted within the optical system 200 to provide for removal and/or replacement of the optical components O.

The optical system 200 can further comprise one or more mechanisms 208 for controlling the movements of the light source S and/or the optical system O. Specifically, the light source S and/or the optical components O can be coupled with one or more mechanisms 208 that move and/or rotate the light source S and/or the optical components O within the housing 201 of the optical system 200 and/or within the frame 102 of the headset 102. For example, as noted above, the one or more mechanisms 208 can be coupled to and/or controlled by a processing circuitry that moves and/or instructs movement of the light source S and/or the optical components O in response to receiving real-time information regarding the location of the subject's pupil(s) and/or in response to information or feedback received from the subject. In some embodiments, the one or more mechanisms 208 can comprise one or more moveable platforms 202, 203 on which the light source S and/or the optical components O are mounted. The platforms 202, 203 can be movable and configured such that they allow movements of the light source S and/or the optical components O within the optical system 200, relative to the housing 201 of the optical system 200 (and/or within the headset 102 of the optical testing system 100). In some embodiments, the platforms 202, 203 can be movable along at least two orthogonal directions for aligning the light source S relative to the pupil of the subject's eye 240. Additionally or alternatively, the platforms 202, 203 can be fixedly positioned relative to the housing 201 and/or the headset 102.

Further, the one or more mechanisms 208 can be coupled to a dial or a knob 218/118 (FIG. 1A) that is configured to engage the one or more mechanisms 208 to move the light source S and/or the optical components O. The dial 218 can be configured such that it can be rotated by a user. A cam 219 can be coupled to the dial 218 and configured to transform the rotational motion of the knob/dial 218 to linear translation of the light source S and/or the optical components O.

Alternatively or additionally, the mechanism for moving the fixation light can comprise a motor 220 (e.g., stepper motor), such as an electrically controlled motor. The motor can be configured such that it can be controlled in response to at least one of a user's input of a refractive correction prescription, real-time user control of the linear translation of the fixation light, and/or in response to instructions received from a processor included in the digital circuitry 300 of the ophthalmic testing system.

The optical system 200 can further comprise an automated pupil tracking mechanism 205 that is configured to align and/or adjust the position and/or orientation of the light source S and/or the optical components O, relative to the pupil of the subject's eye 240. The automated pupil tracking mechanism 205 can include a light source (e.g., a visible light source or an infrared light source) $IR_S$ and a light detector (e.g., a camera, a light detector or camera capable of detecting visible light, an infrared light detector, or an infrared camera) $IR_D$. The light detector $IR_D$ can be a camera that is configured to generate an image of the subject's pupil based on the light returning from the at least one eye 240 of the subject. The light source $IR_S$ can be configured such that it illuminates the subject's eye 240. A portion of the light incident on the subject's eye is reflected and returned to the automated pupil tracking mechanism 205. The light detector $IR_D$ detects the returned light and determines the position and/or size of the pupil of the subject's eye 240 based on the detected returned light.

In some embodiments, the light source $IR_S$ can generate the light beams, e.g., at a wavelength greater than about 700 nm for illuminating the subject's eye. Further, as shown in FIG. 2A, the optical system 200 can comprise a mirror $m_1$, which can be a dichroic mirror. The dichroic mirror can be configured to reflect the visible light generated by the light source S, $IR_S$. The dichroic mirror can also allow the passage of the light returning from the subject's eye, in response to being illuminated by the light source $S/IR_S$ and/or direct the reflected light to the light detector $IR_D$.

The light detector $IR_D$ can be mounted in any suitable position on the optical system and/or at any suitable position within the headset 102 (e.g., rear of the optics and/or behind the dichroic mirror $m_1$) and configured to detect and/or image the light passing through the dichroic mirror $m_1$ and returning from the illuminated eye.

As noted above, the automated pupil tracking mechanism 205 can be coupled to at least one of the light source S, the optical components O, and/or the platform(s) 202, 203 and configured such that it aligns at least one of these elements with the pupil of the subject's eye 240. The automated pupil tracking mechanism 205 can further comprise a feedback system (described below with reference to FIG. 6) and be configured such that upon placement of the ophthalmic testing system 200 against a subject's eye 240, it automatically detects the position and/or size of the pupil of the subject's eye 240, and, in response, aligns at least one of the light source S, the optical components O, and/or the platform(s) 202, 203 to the pupil of the subject's eye 240.

Generally, any suitable mechanisms for tracking a subject's eye or pupil can be employed in practice of the embodiments disclosed herein. By way of example, in some embodiments, an eye tracking mechanism similar to that disclosed in published PCT application number US/2006/062557, entitled "Pupil Reflection Eye Tracking System And Method," and herein incorporated by reference in its entirety, can be employed. With reference to FIG. 2F, such an eye-tracking mechanism 9 can include an illumination source 17 (e.g., source $IR_S$ shown in FIG. 2A), which can emit radiation having one or more wavelengths in the infrared or near-infrared portions of the electromagnetic spectrum, e.g., at a wavelength below 1.5 microns. A variety of illumination sources, such as light-emitting diodes (LEDs), can be employed. The illumination source 17 can be configured to emit a beam of light having a diameter less than the pupil diameter, e.g., less than about 1 mm. A beam splitter 27 can be positioned and configured to direct the light emitted by the illumination source 17 into a subject's eye and allow the light reflected 12 from the subject's eye in response to the illumination reach a detector 11.

The detector 11 (for example, detector $IR_D$, shown in FIG. 2A) can be any suitable detector known in the art, for example a quadrant detector that is divided into quarters and has a plurality of concentric, substantially toroidal zones. The detector 11 can be configured to receive radiation reflected from the retina 13 of the eye, defining a spatial extent of the pupil 14 of the eye, and generate data indicative of the position of the received radiation on the detector 11. The generated data can be transmitted to a processor 23 that contains appropriate software 24 for determining the position of the pupil from the obtained data.

The processor 23 can further process the detector data to select a zone of the detector to use and/or to generate an error signal based on the ratio of the detection signals from different detector zones. The error signal generated by the processor can then be transmitted to a controller 25 that can adjust the bleaching and/or the stimulus light sources (illumination source 17) so as to ensure substantial alignment of the light emitted by these light sources with the subject's pupil. The controller 25 can also receive control signals from the processor 23, and based on the control signals, control various elements of the system, such as the optical elements 31, 32 (e.g., mirrors and lenses) positioned downstream of the source 17 and/or upstream of the pupil 14.

Further, as shown in FIG. 2A, a controller 210 can be in communication with the detector IRD to receive electrical signals generated by the detector IRD in response to the detection of the infrared radiation returning from the subject's eye 240. The controller 210 can be configured to determine the relative alignment of the source IRS with respect to the pupil of the subject's eye 240. More specifically, the controller 240 can operate on the electrical signals generated by the detector IRD to generate an error signal, whose magnitude is indicative of the degree of misalignment between the infrared source IRS and the subject's pupil.

If the error signal generated by the controller is greater than a predefined threshold, the controller 240 can cause the movement of the movable platforms 202, 203 to minimize the error signal, thereby bringing the source S in substantial alignment with the subject's pupil. As the light source S, generating the bleaching light, the stimulus light, as well as the fixation light, is fixedly positioned on the platform 202, 203, it can move on the platform, relative the subject's pupil, and result in substantial alignment of the light source S relative to the subject's pupil.

The movable platform 203, 203' upon which the lens is mounted can comprise an automatic alignment mechanism that is configured to continuously align the optics relative to the light sources to direct the light to the subject's pupil. The movable platform 203, 203' can be moved along three orthogonal dimensions, which are designated herein as X, Y, and Z dimensions. The Z-dimension is chosen to be along the direction of the light propagation and the X and Y dimensions are orthogonal to the Z-direction. The movable platform 203, 203' can be moved along these dimensions to ensure that the direction of the light propagation is substantially aligned with the subject's pupil.

Referring back to FIG. 2A, the infrared light source $IR_S$ and the infrared light detector $IR_D$ of the pupil tracking mechanism 205 can be disposed on any suitable position in the housing 201 and/or the headset 102, such as adjacent to the optical interfaces 122L, 122R, adjacent to the transparent windows 123L, 123R, adjacent to the light seals 124L, 124R, on the wall of the rear housing inside the eye chamber including the rear housing, eye cups, and/or on the disposable light seal, adjacent to the eye.

Further, embodiments disclosed herein can generally employ any suitable technique for operating on the detected signals and arriving at a degree of alignment of the light source relative to the subject's pupil. Moreover, upon the detection of a misalignment of the light source relative to the subject's pupil, the controller 210 can cause the movement of the movable platforms 202, 203 via a feedback loop to bring the light source S and/or the optical components O, in substantial alignment relative to the subject's pupil. More specifically, in some embodiments, the controller 110 can actuate various means (e.g., motors) for moving the movable platforms 202, 203 along X, Y and Z axes.

Further, during the performance of an ophthalmic test, the alignment mechanism 205 can continuously track the position of the subject's pupil and continuously correct for any misalignment of the light sources relative to the subject's pupil. In this manner, the alignment mechanism can correct, for example, for involuntary movements of the subject's eye, vibrations and other unwanted motions of the optical system, among others.

In some embodiments, the pupil(s) of the subject's eye(s) can be dilated prior to using the ophthalmic testing system 100 disclosed herein. The automated pupil tracking mechanism 205 can be configured to correct for the subject's pupil size and for any changes induced in the subject's pupil(s). The automated pupil tracking mechanism 205 can also provide these corrections in real time. Alternatively or additionally, the pupil tracking mechanism 205 can be configured to correct for the position of the subject's upper and/or lower eye lids and/or eyelashes in correcting for and determining the subject's pupil size or position. Further, in correcting for the subject's pupil size, the ophthalmic testing system 150 can adjust the intensity of the stimulus and/or the bleaching lights applied to the subject's eye. In other words, the ophthalmic testing system 150 can adjust the intensity of the stimulus and/or bleaching lights applied to the subject's eye based on the size of that subject's pupil(s).

Although not described herein, the optical system 200 can generally include any components required for conducting its intended functions. Non-limiting examples of the functions that can be provided by the optical system 200 include functions required for performing Fundus Retinal Imaging, Retinal Densitometry, Optical Coherence Tomography (OCT), Fluorescein Angiography, OCT Angiography (OCTA), Multi-spectral Imaging, Scanning Laser Ophthalmoscope, Anterior Segment OCT, Deep-field OCT, Retinal Metabolic Imaging, Ocular Blood Flow Imaging, Adaptive Optics, Autofluorescence, Non-mydriatic Fundus Camera, Optic Nerve Imaging, Ultrasound, Anterior Segment Photography, Slit Lamp, and Refractive Eye Care testing including functions of a Pachymeter and Interior Segment testing functions.

FIG. 3 is a high-level block diagram of digital electronic circuitry and hardware 300 that can be used with, incorporated in, or fully or partially included in an ophthalmic testing and measurement system according to the embodiments disclosed herein. The electric circuitry 300 can include a processor 310 that is configured to monitor the operation of the ophthalmic testing system, send and/or receive signals regarding the operation of the ophthalmic testing system, and/or control the operation of the ophthalmic testing system.

The processor 310 can be configured to collect or receive information and data regarding the operation of the ophthalmic testing system 150 and/or the head-wearable device 100 and/or store or forward information and data to another entity (e.g., another portion of an ophthalmic testing system, etc.). The processor 310 can further be configured to control, monitor, and/or carry out various functions needed for analysis, interpretation, tracking, and reporting of information and data collected by the ophthalmic testing system 150 (for example, as implemented in the head-wearable device 100 shown in FIG. 1A). Generally, these functions can be carried out and implemented by any suitable computer system and/or in digital circuitry or computer hardware, and the processor 310 can implement and/or control the various functions and methods described herein.

The processor 310 can further be generally configured to monitor the operation of the ophthalmic testing system 150, send and/or receive signals regarding the operation of the system 150, and/or control the operation of the system 150. The processor 310 can also collect or receive data regarding the operation of the system 150 and/or store or forward the data to another entity (e.g., a medical facility, etc.).

The processor 310 can be connected to a main memory 320, and comprise a central processing unit (CPU) 315 that includes processing circuitry configured to manipulate instructions received from the main memory 320 and execute various instructions. The CPU 315 can be any suitable processing unit known in the art. For example, the CPU 315 can be a general and/or special purpose microprocessor, such as an application-specific instruction set processor, graphics processing unit, physics processing unit, digital signal processor, image processor, coprocessor, floating-point processor, network processor, and/or any other suitable processor that can be used in a digital computing circuitry. Alternatively or additionally, the processor can comprise at least one of a multi-core processor and a front-end processor.

Generally, the processor 310 and the CPU 315 can be configured to receive instructions and data from the main memory 320 (e.g., a read-only memory or a random access memory or both) and execute the instructions. The instructions and other data can be stored in the main memory 320. The processor 310 and the main memory 320 can be included in or supplemented by special purpose logic circuitry. The main memory 320 can be any suitable form of volatile memory, non-volatile memory, semi-volatile memory, or virtual memory included in machine-readable storage devices suitable for embodying data and computer program instructions. For example, the main memory 320 can comprise magnetic disks (e.g., internal or removable disks), magneto-optical disks, one or more of a semiconductor memory device (e.g., EPROM or EEPROM), flash memory, CD-ROM, and/or DVD-ROM disks.

The main memory 320 can comprise an operating system 325 that is configured to implement various operating system functions. For example, the operating system 325 can be responsible for controlling access to various devices, memory management, and/or implementing various functions of the optical testing system 150. Generally, the operating system 325 can be any suitable system software that can manage computer hardware and software resources and provide common services for computer programs.

The main memory 320 can also hold application software 327. For example, the main memory 320 and application software 327 can include various computer executable instructions, application software, and data structures, such as computer executable instructions and data structures that implement various aspects of the embodiments described herein. For example, the main memory 320 and application software 327 can include computer executable instructions, application software, and data structures, such as computer executable instructions and data structures that implement a subject-instruction system (e.g., an automated subject-instruction system, as detailed below), which can be employed to communicate with the subject in order to, for example, instruct the subject during an ophthalmic test.

Generally, the functions performed by the ophthalmic testing system 150 can be implemented in digital electronic circuitry or in computer hardware that executes software, firmware, or combinations thereof. The implementation can be as a computer program product (e.g., a computer program tangibly embodied in a non-transitory machine-readable storage device) for execution by or to control the operation of a data processing apparatus (e.g., a computer, a programmable processor, or multiple computers).

The main memory 320 can also be connected to a cache unit (not shown) configured to store copies of the data from the most frequently used main memory 320. The program codes that can be used with the embodiments disclosed herein can be implemented and written in any form of programming language, including compiled or interpreted languages, and can be deployed in any form, including as a stand-alone program or as a component, module, subroutine, or other unit suitable for use in a computing environment. A computer program can be configured to be executed on a computer, or on multiple computers, at one site or distributed across multiple sites and interconnected by a communications network, such as the Internet.

The processor 310 can further be coupled to a database or data storage 330. The data storage 330 can be configured to store information and data relating to various functions and operations of the ophthalmic testing and measurement system 150. For example, the data storage 330 can store the data collected by the ophthalmic testing and measurement system 150. Further, in some embodiments, the database 330 can be configured to store information regarding detected events that may be of interest to the authorized party. For example, as detailed below, the database 330 can be configured to store the number of detected sudden acceleration or deceleration events that occur in the head-wearable device 100 implementation of the ophthalmic testing and measurement system 150 over a time period.

The processor 310 can further be coupled to a display 317 (e.g., display 117 shown also in FIG. 1A). The display 370 can be configured to receive information and instructions from the processor. The display 370 can generally be any suitable display available in the art, for example a Liquid Crystal Display (LCD) or a light emitting diode (LED) display. For example, the display 370 can be a smart and/or touch sensitive display that can receive instructions from a user and/or provide information to the user.

The processor 310 can further be connected to various interfaces. The connection to the various interfaces can be established via a system or an input/output (I/O) interface 349 (e.g., Bluetooth® USB connector, audio interface, FireWire, interface for connecting peripheral devices, etc.). The I/O interface 349 can be directly or indirectly connected to the ophthalmic testing system 150.

The processor 310 can further be coupled to a communication interface 340, such as a network interface. The communication interface 340 can be a communication interface that is included in the ophthalmic testing and measurement system 150 and/or a remote communications interface 340 that is configured to communicate with the ophthalmic testing and measurement system 150. For example, the communications interface 340 can be a communications interface that is configured to provide the ophthalmic testing and measurement system 150 with a connection to a suitable communications network 344, such as the Internet. Transmission and reception of data, information, and instructions can occur over the communications network 344. Further, in some embodiments, the communications interface 340 can be an interface that is configured to allow communication between the digital circuitry 300 (e.g., a remote computer) and the ophthalmic testing and measurement system 150 (e.g., via any suitable communications means such as a wired or wireless communications protocols including WIFI and Bluetooth® communications schemes).

Figure 4A:
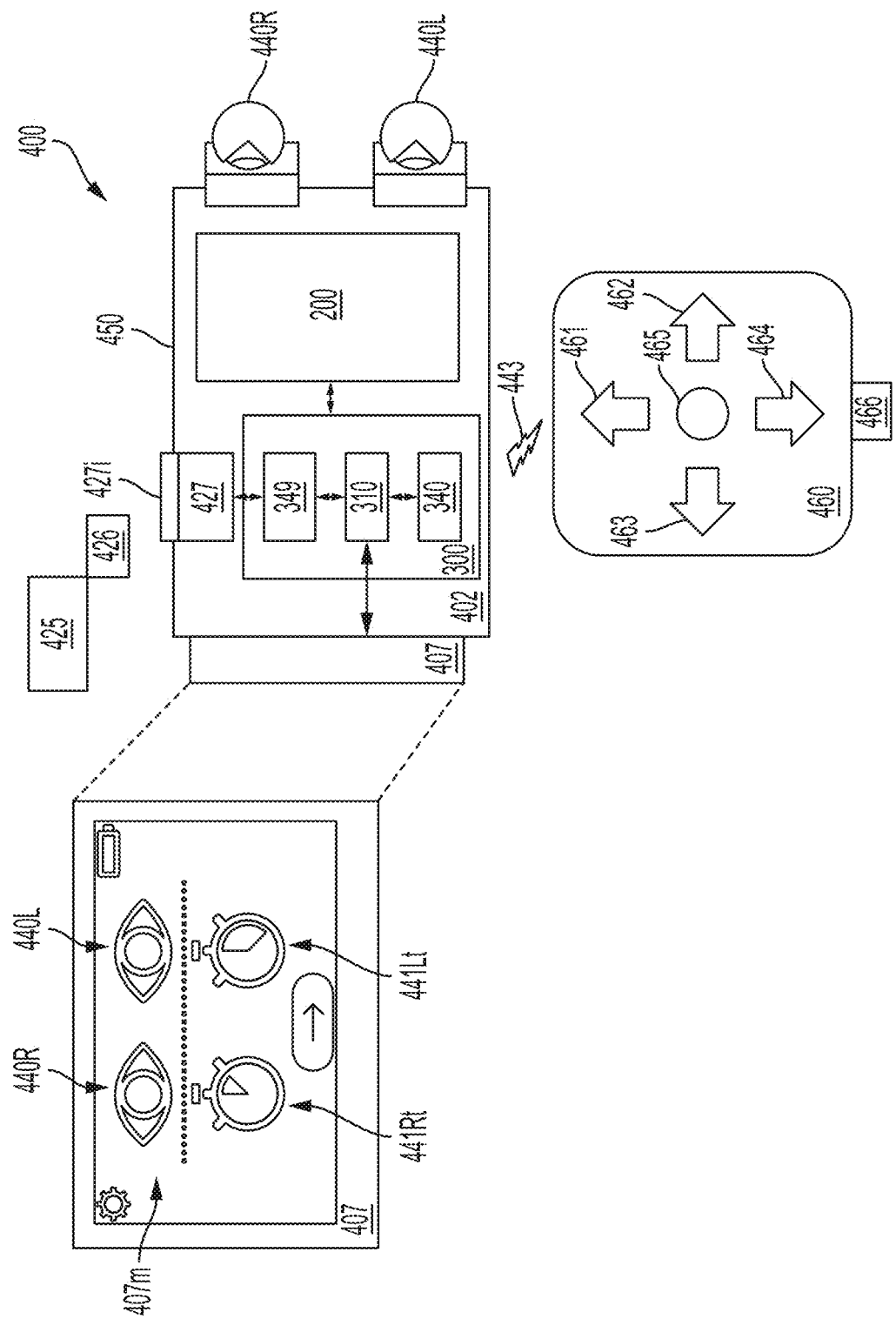
FIG. 4A is a high-level block diagram of an ophthalmic testing system according to some embodiments disclosed herein.

FIG. 4A is a high-level block diagram of a system 400 according to some embodiments disclosed herein. In the example shown in FIG. 4A, the ophthalmic testing and measurement system 450 comprises an interface unit 460 that is configured to 1) receive instructions for operating the ophthalmic testing and measurement system 450 from a provider/clinician providing an ophthalmic test to a test subject and 2) receive a response from the subject.

Specifically, as shown in FIG. 4A and described previously in connection with FIGS. 1A-3, the ophthalmic testing system 450 can be implemented in a headset 402 of a head-wearable device and configured to receive at least one eye 440 of the subject. The ophthalmic testing system 450 can comprise an optical system 200 that includes the various components needed to conduct the ophthalmic tests and measurements disclosed herein and the digital electronic circuitry and hardware 300 for implementing various functions of the ophthalmic testing system 450. As explained in relation to FIG. 3, the digital electronic circuitry and hardware 300 can comprise a processor 310, an I/O interface 349, and a communications interface 340. The I/O interface 349 can be directly or indirectly connected to the ophthalmic testing system 450 and configured to couple the ophthalmic testing system 450 with various interfaces. For example, as noted above, the I/O interface 349 can couple the ophthalmic testing system 450 to an RFID reader 427. The RFID reader 427 can be any RFID reader known in the art. In the head-wearable implementation of the ophthalmic testing system (e.g., FIG. 1A), the RFID reader 427 can comprise an interface 427i that is positioned at any suitable location on the external surface of the head-wearable device.

The RFID reader 427 can be configured to provide asset tracking (e.g., asset tracking of disposables) and ensure that only systems, equipment, and/or parts produced by original equipment manufacturer (OEM) are used with the ophthalmic testing system 450. For example, as noted above, the RFID reader 427 can be configured to ensure single usage of disposable/hygienic covers used to cover the light seals 124 used to isolate the subject's eyes from ambient light.

As described above, in some embodiments, a cover 425 having an RFID tag 426 (e.g., a passive RFID tag) can be used with the light seal. The RFID tag 426 can be configured to enforce single usage of the disposable cover 425. For example, the ophthalmic testing system 450 can be configured such that it can only be used to conduct a test once the RFID tag 426 of the cover is scanned against the RFID reader 427 (e.g., by bringing the RFID tag 426 in the vicinity of the interface 427i of the RFID reader 427). Although described in terms of an RFID tag 426 and an RFID reader, one having ordinary skill in the art should appreciate that any tracking system known/available in the art can be used for asset tracking and management with the embodiments disclosed herein. For example, a barcode 426 can be coupled to the cover and configured to be tracked by a barcode reader 427. Further, in addition to the cover 425, any other part or portion of the ophthalmic testing system 450 can comprise a tracking mechanism, such as an RFID tag and/or a barcode.

As noted, the tracking mechanism 427 (e.g., RFID reader or barcode reader, hereinafter generally referred to as "RFID reader") can be coupled to a processor 310 of the digital circuitry 300 of the ophthalmic testing system 350 directly or indirectly (e.g., through an I/O interface 349). The RFID reader 427 can be configured such that upon scanning an RFID tag 426 (or a barcode or an OCR code, hereinafter generally referred to as "RFID tag"), the RFID reader sends the information stored in the RFID tag 426 to the processor 310 for processing. The processor 310 processes the information and determines whether the information on the RFID tag 426 corresponds to an RFID tag recorded on an original manufacturer's disposable. For example, the database 330 (FIG. 3) of the ophthalmic testing system 450 can comprise a listing of information stored on RFID tags of consumables/parts known to have been manufactured by the original manufacturer of the ophthalmic testing system 450. Upon receiving the information included on a scanned RFID tag, the processor 310 can check the information on the scanned RFID tag against the information in the database 330 to determine whether a match exists. If a match is found, the processor 310 accepts the RFID tag 426 and the consumable 425 as an RFID tag 216 and consumable belonging to the original manufacturer. The processor 310 can also allow an operator/clinician operating the ophthalmic testing system 450 to conduct a test on the subject, and/or the subject herself, to provide identifying information that can be used to uniquely identify that test subject. As detailed below, the identifying information can include any suitable information known and/or available in the art, for example, name, medical record number, biometric information, etc.

As noted above, the ophthalmic testing and measurement system 450 can comprise a interface unit 460 that is configured to 1) receive instructions for operating the ophthalmic testing and measurement system 450 from a provider/ clinician administrating an ophthalmic test to a test subject and 2) receive a response from the subject. In some embodiments, the interface unit 460 can comprise one or more navigation keys configured to allow the provider and/or the clinician to initialize and/or conduct the ophthalmic test at hand. For example, as shown in FIG. 4A, the interface unit 460 can comprise one or more keys 461, 462, 463, 464 configured to provide the clinician with the ability to move a cursor on the screen in the vertical (up and down) and horizontal (left and right) directions. It should be noted that although described as having four keys 461, 462, 463, 464, the interface unit 460 can include any number of keys and provide the clinician with motion in any suitable direction. Further, the provider can move the cursor on the screen in any suitable number of directions, for example the interface can provide a five-way motion of the cursor on the screen.

Further, the display 407 of the ophthalmic testing and measurement system 450 can be configured to allow the clinician to initialize the test and/or facilitate the testing process. Specifically, as shown in FIG. 4A, the display 407 of the ophthalmic testing system 450 can be configured to provide the clinician with one or more menus for use in initializing and/or conducting an ophthalmic test. For example as shown in FIG. 4A, the display 402 can comprise a menu 407*m* that allows the clinician to select at least one eye 440R, 440L of the subject for conducting the test. Once an eye 440R is selected, the display 407 can present the clinician with another menu for selecting a test to perform on the subject selected eye 440R. In some embodiments, the display 407 can allow the clinician to conduct the same or two different tests on the subject's eyes. Further, the display 407 can provide the clinician with the option of conducting more than one test on an eye 440R of the test subject. The tests conducted on the subject's eye(s) can be administered concurrently, in parallel, and/or at different times during the testing process.

Once an eye for testing and one or more tests for conducting on that eye are selected, the display 407 can provide the clinician with information regarding the test, for example time lapsed and/or expected time remaining for completion of the test. For example, as shown in FIG. 4A, the display 407 can provide the clinician with the time remaining 440Rt, 440Lt for completion of the test(s) on each eye 440R, 440L of the subject.

As noted, the display 407 is coupled to the processor and configured to provide and/or receive information from the processor 310. The processor 310 and the digital circuitry 300 of the ophthalmic testing system 450 are also coupled to the optical system 200 and configured to control and/or adjust the optical system 200 to provide a test selected on the display 407 of the ophthalmic testing system 450. This arrangement allows a clinician operating the interface unit 460 to remotely, and without directly coming in contact with the ophthalmic testing system 450, which may be mounted on a subject's head (in a head-wearable implementation), control the operation of the ophthalmic testing system 450.

Figures 1, 4A:
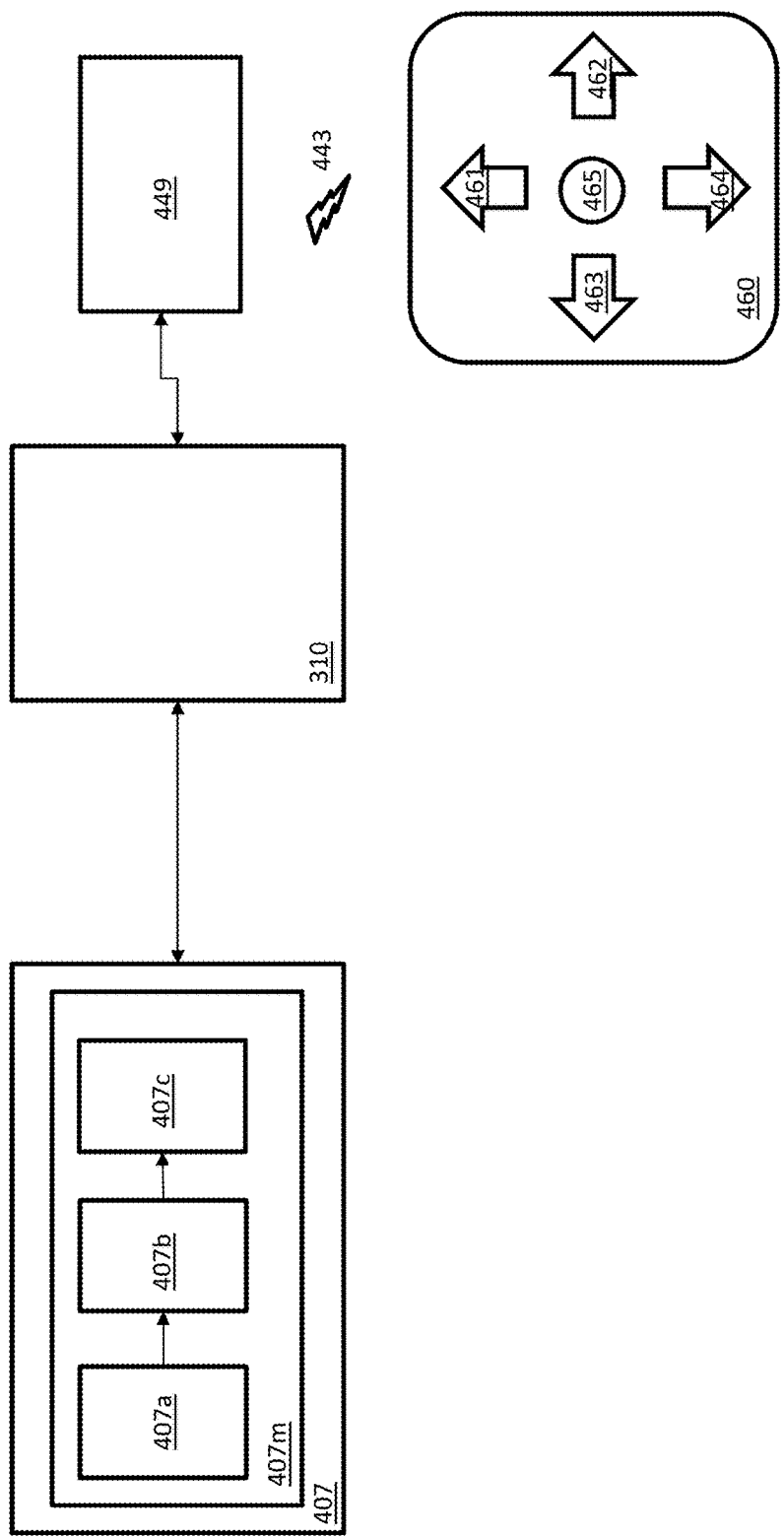
Figure 4B:
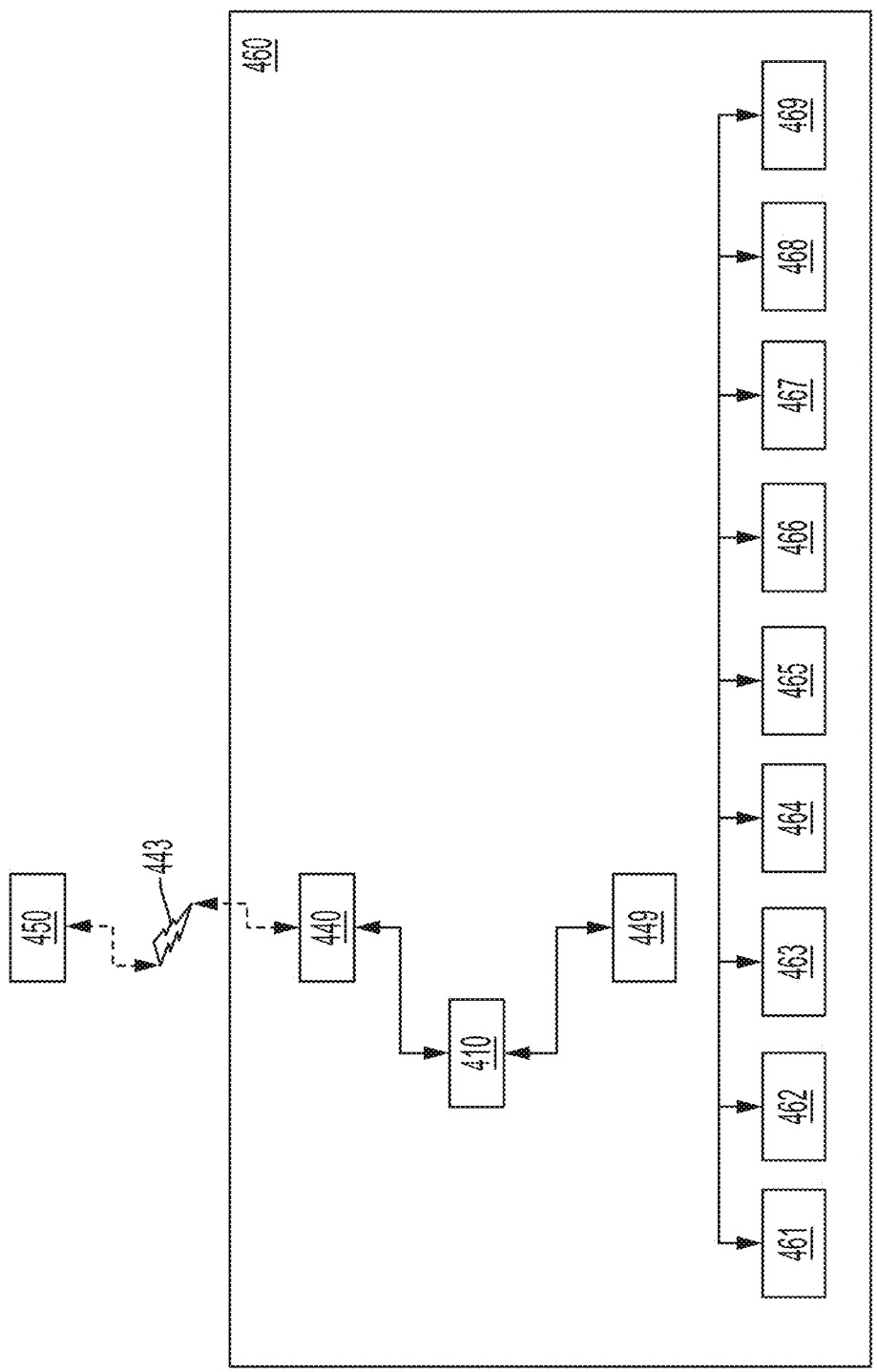
FIG. 4B is yet another high-level block diagram of an ophthalmic testing system according to some embodiments disclosed herein.

FIG. 4B is a high-level block diagram of an interface unit 460 according to some embodiments disclosed herein. The interface unit 460 can include digital circuitry and hardware for conducting and performing various functions of the interface unit 460. The digital circuitry can comprise similar elements as those described with reference to FIG. 3. Specifically, the interface unit 460 can comprise a processor 410 that connects to a communication interface 440 and an I/O interface 449. The I/O interface 449 can be coupled to various I/O interface devices that can receive instructions from the provider/clinician and subject (such as input keys 461, 462, 463, 464, 465), an audio input element 466 (such as a microphone), an audio output element 467 (such as a speaker), a display 468 (such as an interactive display), and other input/output interface devices 469.

It should be understood that although shown a separate unit in FIG. 4A, the interface unit 460 can be an integral part of the ophthalmic testing system 450 and located on board of the ophthalmic testing system (e.g., on a tabletop device and/or implemented in a head-wearable device). Further, the interface unit 460 and the ophthalmic testing system 450 can comprise a single processing circuitry responsible for conducting the functions of the interface unit 460 and the ophthalmic testing system 450.

The audio input element 466 can generally comprise any suitable audio input element known in the art. Generally, any suitable number of audio input elements can be used. For example, the interface unit 460 can comprise one or more microphones 456. The one or more audio input elements 466 can be configured to receive audio input from the test subject, the clinician, or from the testing area surrounding the subject and clinician (e.g., from the subject and/or individuals conducting the ophthalmic test(s)).

In some embodiments, an audio input element 466 (e.g., microphone) can be configured to receive responses of the test subject to the ophthalmic test being performed on the subject. The audio obtained from the test subject (or other individuals) can be forwarded to the processor 410 of the interface unit 450 for analysis and processing. Alternatively or additionally, the audio input can be forwarded to the processor of the ophthalmic testing unit 450 and/or to the processor of another component or device for processing or analysis.

In some embodiments, the audio obtained from the test subject can be forwarded to the processor for processing for analysis and processing. Upon processing, the processor can use the information obtained from the subject to issue instructions to the subject, carry out the test, and/or make appropriate adjustments to the test.

The audio input element 466 can be disposed in any suitable location on or within the ophthalmic testing system 450 and/or at any location within the head-wearable device. For example, the one or more audio input element 466 can be disposed on any suitable position on the head-mount 103 (e.g., adjacent to or in the vicinity of the subject's ear), incorporated in the head-mount 103, incorporated in the headset 102, and/or placed at any desired or suitable location in the vicinity of the ophthalmic testing system 450 (e.g., in the exam room).

The interface unit 460 can further include one or more audio speakers 467, which may be connected to the processor 410 via the I/O unit 449. The one or more speakers 467 can be any suitable audio speaker available in the art and can be disposed in any suitable location on or within the ophthalmic testing system 450. For example, the one or more audio speakers 467 can be disposed on any suitable position on the head-mount 103 (e.g., adjacent to or in the vicinity of the subject's ear), incorporated in the head-mount 103, incorporated in the headset 102, placed at any desired or suitable location in the vicinity of the ophthalmic testing system 450 (e.g., in the exam room), and/or be coupled with the ophthalmic testing system 450 using a wired or wireless connection.

The audio speakers 467 can be configured such that they can be used to communicate (e.g., via audio communication) with the subject. For example, as discussed in further details below, the ophthalmic testing system 450 can include a subject-instructor, implemented by the processor (e.g., implemented in the application software 327) that is configured to communicate with the test subject via the audio speakers 467. The speaker(s) 467 can be utilized to provide verbal/audio commands and instructions to the subject and/or inform the subject of the status of the ophthalmic test. The verbal instructions can be issued by the processor and/or by a clinician or a by a medical professional (or through an automated system). Additionally or alternatively, the audio speakers 467 can be used to provide background music, sounds, or comments (encouraging comments, comments regarding the test, etc.) to the subject in order to improve focus and attention during the test in order to reduce fixation error, error rates and/or failed tests.

As noted, the audio speaker 467 can be configured such that they can be used to communicate (e.g., via audio communication) with the subject. For example, the audio speaker 467 can be configured such that they can be utilized by a medical professional (or through an automated system) to provide verbal/audio commands and instructions to the subject and/or inform the subject of the status of the ophthalmic test.

The audio input 466 and output 467 systems (speakers and microphones described herein) can be coupled to the ophthalmic testing system 450 using any suitable means known in the art. For example, the audio input and/or output systems can connect to the system 450 using a wireless and/or Bluetooth® functionality. In some embodiments, the audio input and/or output functionality can be provided through a wireless headset (e.g., a wireless or a Bluetooth® headphone). The audio speaker 467 and/or any audio input 466 system (microphone) used with the embodiments disclosed herein can generally be any suitable audio system known in the art. In some embodiments, the audio speaker 467 and/or any audio input 466 system can comprise functionalities needed to reduce or cancel background noise. For example, the audio speaker 467 and/or any audio input 466 system can comprise any suitable functionality available in the art that can at least partially isolate the subject's hearing to the verbal guidance provided by system 450 and/or reduce background noise in the audio input provided to the system.

The interface unit 460 can further include one or more displays 468, which can be coupled to the processor 410 via the I/O interface 449. The display(s) 468 can be configured to present relevant information to the subject and/or receive information and/or control signals from the subject and/or clinician. Further, the display 468 can be an interactive display that is configured to receive information from the subject and/or clinician.

Figure 4D:
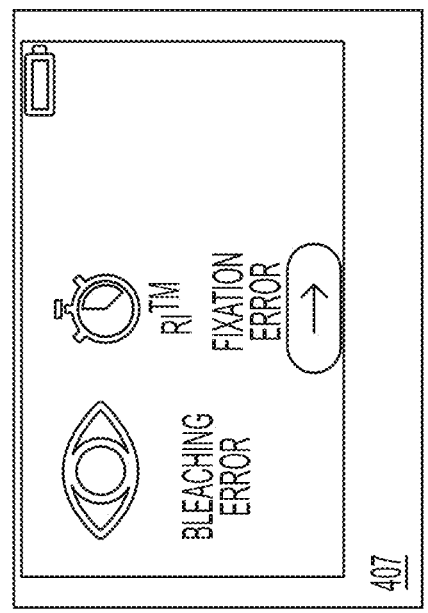
FIG. 4D another example of menu items on a display of an ophthalmic testing system according to some embodiments disclosed herein.
Figure 4C:
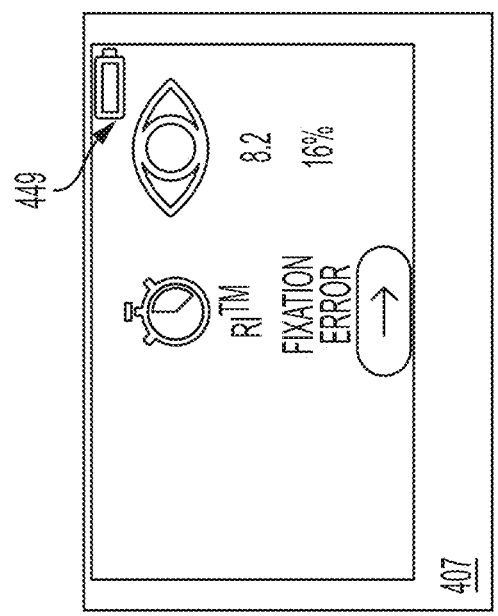
FIG. 4C is an example of menu items on a display of an ophthalmic testing system according to some embodiments disclosed herein.
Figure 4E:
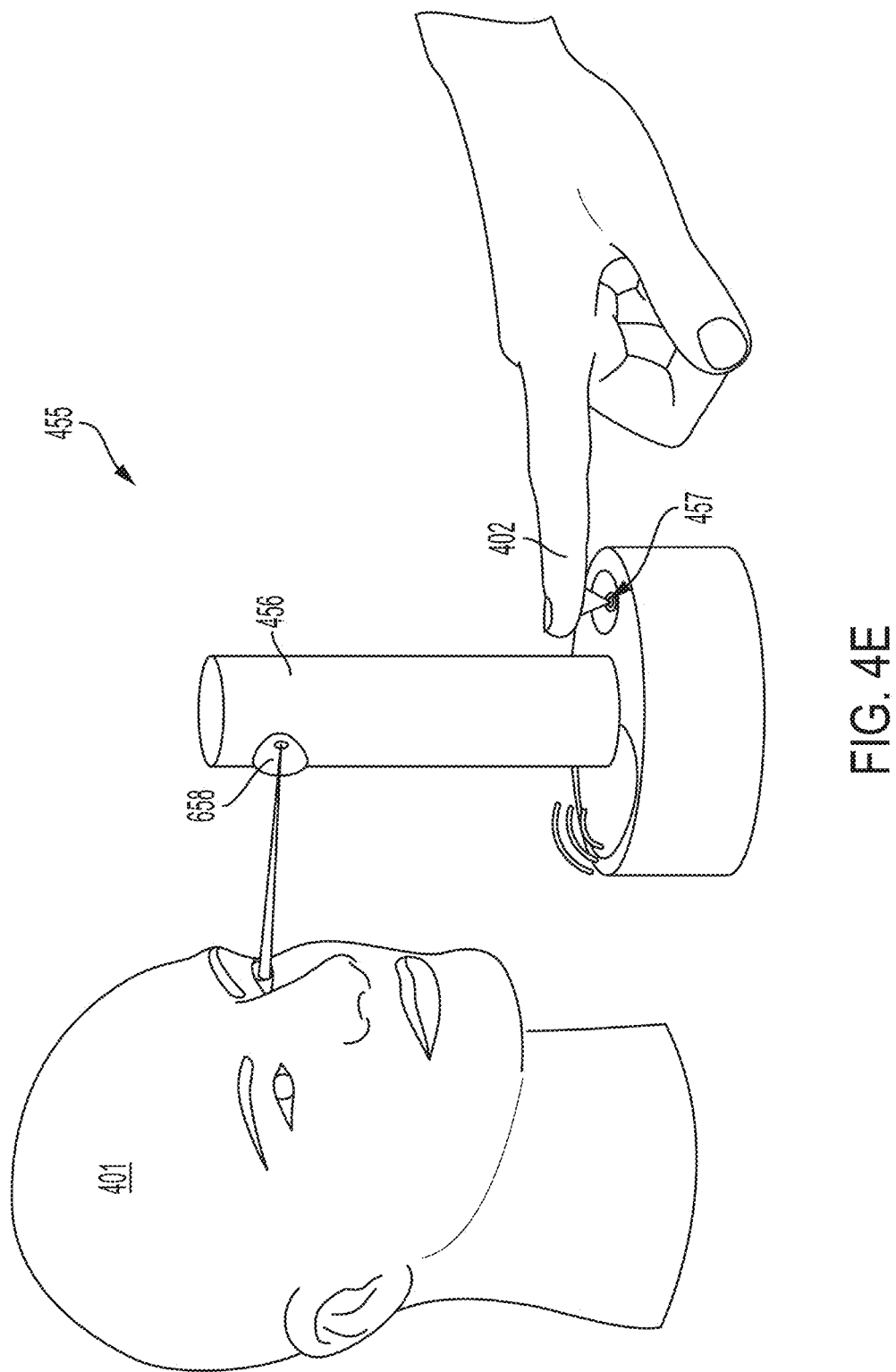
FIG. 4E illustrates a high-level diagram of an interface that can be used to obtain biometric information that identifies a test subject according to some embodiments disclosed herein.

Further, as shown in FIGS. 4C-4E, in addition to presenting/displaying a visual menu of the tests provided by the system 450, the display can also provide/display updates regarding test status and progression (as described above), possible errors, test results, and/or battery status 449. For example, the display can provide information regarding possible fixation (FIG. 4C) and/or bleaching (FIG. 4D) errors, progression and results (FIG. 4C) of a Rod Intercept™ (RI™) offered by MacuLogix Inc. (Harrisburg, PA, U.S.A).

Although not specifically shown in FIGS. 4A-4E, the display 407 can be configured to provide/display various functions, such as providing information regarding the status of the head-wearable system 100 and the headset 102. For example, the display can be configured to display or provide information as to whether the head-wearable system 100 has been securely placed against the subject's head, whether the headset 102 is securely positioned against the subject's eyes 440R, 440L, whether the light seal is sufficiently obstructing passage of light to the test subject's eyes 140R, 140L, etc.

Further, although shown as a display that has been integrated in the system 450, it should be understood that the display can be directly and/or indirectly coupled to the system 450. For example, as shown in FIG. 1A, the display 107 can be disposed on a front face 102F of the headset 102 such that it covers at least a portion of the front face 102F of the headset 102 and is visible, for example to an individual administering an ophthalmic test. Alternatively or additionally, the display 107 can be remotely coupled to the headset 102 using a wired or wireless connection.

In addition to receiving instructions and commands from the provider/clinician, the interface unit 460 can also be configured to receive instructions/responses/commands from the test subject. Generally, the response received from the test subject can be a response provided by the test subject in connection with one or more stimuli provided by the ophthalmic testing system 450 to the test subject. For example, in some embodiments, the interface unit 460 can be configured to receive a response from the subject once a subject recognizes a stimulus light. Specifically, as noted above, the ophthalmic testing system 450 described herein can be configured to conduct a number of tests and measurements, including measurement of a subject's eye's adaptation to darkness. This can be performed by bleaching a region of the subject's retina and subsequently presenting a stimulus light (e.g., in the form of an image) having a lower intensity within the bleached region of the retina. Throughout the test, the subject is directed to fixate their gaze on a fixation light and provide a response when they recognize the stimulus light. The interface unit 460 can be configured to receive the subject's response to the stimulus light.

In some embodiments, interface unit 460 can be configured such that it can toggle between a clinician mode and a subject mode. Specifically, the interface unit 460 can be configured such that 1) it allows for usage of multiple keys and/or operation of a single key in multiple directions, while the interface unit 460 is in the clinician mode and 2) it can be switched to a single key and/or single button response key while the unit 460 is in a subject mode. This allows the system to place the interface unit 460 in a clinician mode and use the multiple keys and/or multi-directional keys to set up and/or initialize the ophthalmic testing system 450. Once the test is ready to be conducted, the system can place the interface unit 460 in a subject mode and hand the interface unit 460 to the subject for use in providing her response (e.g., to the stimulus light).

In some embodiments, the ophthalmic testing system 450 can be configured such that the transition between the clinician and subject modes occurs automatically upon completion of the test setup on the ophthalmic testing system 450. Specifically, as shown in FIG. 4A-1, the clinician can use the multi-directional keys 461, 462, 463, 464, 465 on the interface 460 to navigate through a menu 407 *m* for initiating an ophthalmic test using the ophthalmic testing system 450 described herein. The menu can include multiple sub-menus and options 407 *a*, 407 *b*, 407 *c*, through which the clinician navigates to initiate a test. For example, the clinician can use the interface 460 to select an eye of the subject for performing a test (e.g., right eye, submenu 407 *a*), selecting a test (e.g., dark adaptation, submenu 407 *b*), and finalize setting up the test (submenu 407 *c*). The clinician's selection can be communicated to a processor (e.g., processor 310). The processor 310 can analyze the received information and determine that the test has been initialized and is ready for being provided to the subject. At that time, the processor 310 can communicate with the interface 460 (via the I/O interface 449 and a connection 443 (Bluetooth®) and instruct the interface 460 to switch from the clinician mode to the subject mode. While in the subject mode, the interface can no longer be used to control the device and/or change the setup the ophthalmic test and can only be used to provide a response to the system (e.g., response to a stimulus light).

The processor 310 can monitor the subject's response to the test and/or the progression of the test. Upon completion of the test, the processor 310 can determine that the ophthalmic test is complete and, in response, instruct the interface 460 to transition back to the clinician mode. While in the clinician mode, the interface 460 can be used to issue instructions and control the operation of the ophthalmic device 450.

In some embodiments, the transition between the clinician and test subject mode can be controlled by the processor based on the manner in which the processor analyzes the signals received from the interface 460. Specifically, the processor 310 can be configured such that it analyzes the responses received from the multi-directional keys in accordance with their intended direction as long as an ophthalmic test is not in progress. Specifically, if the processor 310 determines that a test is not in progress (e.g., while the clinician is navigating the menus to setup the test and/or is using the keys to read and/or delete test results), it processes the responses received from the multi-directional keys based on their intended direction (upward motion/key is translated into upward motion on the screen, downward motion/key is translated into downward motion on the screen, etc.). However, once a test is fully setup and/or is in progress, the processor 310 interprets any response received from the interface (regardless of which motion/key is used) as a patient's response to the system (e.g., a patient response to a stimulus light).

Additionally or alternatively, in some embodiments, the clinician can employ a key 486 on the interface unit 460 to switch the interface unit 460 between the clinician and subject modes. Placing the interface unit 460 in the subject mode can provide the subject with a single key for providing her response, thereby reducing potential confusion for the test subject and preventing the subject from altering the setup of the test.

Further, it should be noted that although shown as different keys 461, 462, 463, 464, 465, the interface unit 460 can comprise a single key that can be toggled between being multi-directional (clinician mode) and single directional (subject mode). Moreover, the interface unit 460 can generally comprise any interface configured to receive a response from the test subject and/or receive instructions from the clinician/provider. As noted, the interface unit 460 can be coupled to the I/O interface 349 of the digital circuitry 300 such that information received by the interface unit 460 is directed, through the I/O interface 349 to the processor 310. Similarly, the interface unit 460 can be configured to receive instructions from the processor 310 through the I/O interface 349. The connection between the interface unit 460 and the I/O interface 349 can be established via any suitable communications protocol/technique known in the art. For example, the connection between the interface unit 460 and the I/O interface 349 can be established via wireless (Bluetooth®) or a wired connection.

In some embodiments, the interface unit 460 can be a button or a computer mouse that is pressed or clicked by the test subject every time the subject observes a flash of light. Additionally or alternatively, the interface unit 460 can be an audio inlet configured to receive verbal instructions from the test subject. For example, the interface unit 460 can receive verbal response from the test subject in the form of natural language. Further, the verbal responses can be variable in nature or constrained to one, two, or more fixed words or statements that the ophthalmic testing system is programmed to accept.

As noted above, the processor 310 can employ biometric information of the subject to uniquely identify the test subject. In some embodiments, the ophthalmic testing system 650 can comprise a biometric interface 455 that is configured for use in obtaining the biometric information of the test subject.

FIG. 4E illustrates a high-level diagram of an interface 455 that can be used to obtain biometric information that identifies a test subject. The interface 455 can be coupled to the processor 310 of the ophthalmic testing system 450 (e.g., through the I/O interface 349) and configured to forward biometric information obtained from the test subject to the processor 310. The processor can store the obtained information in the database 330 of the digital circuitry 300 and/use perform any other suitable processing on the obtained information (e.g., match to already existing information in the database 330).

In some embodiments, the interface 455 can comprise a biometric scanner configured to obtain at least one biometric feature of the test subject. For example, the interface 455 can comprise a biometric scanner 456 that is configured to obtain at least one of a facial feature of the test subject 401, information obtained from an iris of the eye of the test subject (e.g., using an iris scanner 458), information obtained from a retina of the eye of the test subject, and/or a fingerprint (using a finger print scanner 467) obtained from a finger 402 the test subject.

As noted, the interface 455 can forward the biometric information obtained by the biometric scanner 456 to the processor 310 for processing and analysis. The processor 310 can use the biometric information to create a new profile for the test subject and/or access an existing profile for the test subject 301. For example, the processor can compare the obtained biometric information with biometric information previously stored in the database 330 to determine if a profile for the test subject has been previously stored in the database. If a profile matching the biometric information exists, the processor 310 can identify the test subject by matching his/her biometric information to the existing profile. If a profile for the test subject is not identified, the processor can store the biometric information of the test subject, along with other information, such as name of the test subject, address of the test subject, any identifiers associated with the test subject, and health insurance information for the test subject, in a new profile for the test subject. Additionally or alternatively, the profile can be obtained from an electronic health record system, such as an electronic health record system that is maintained on a cloud-based server. In such implementations, the processor 310 can access the subject's profile via the communication interface and the communications network. The processor can store a subject's profile in the database 330 on the ophthalmic testing system 450 or a remote database located at another location. Further, the processor 310 can be configured to receive and store, in the memory of the ophthalmic testing system, at least one medical history of the test subject, medical insurance information associated with the test subject, available pretesting diagnostics information associated with the test subject. Alternatively or additionally, the processor 310 can be configured to receive and store, in the memory of the ophthalmic testing system, at least one medical history of the test subject, medical insurance information associated with the test subject, and available pretesting diagnostics information associated with the test subject.

Figure 5A:
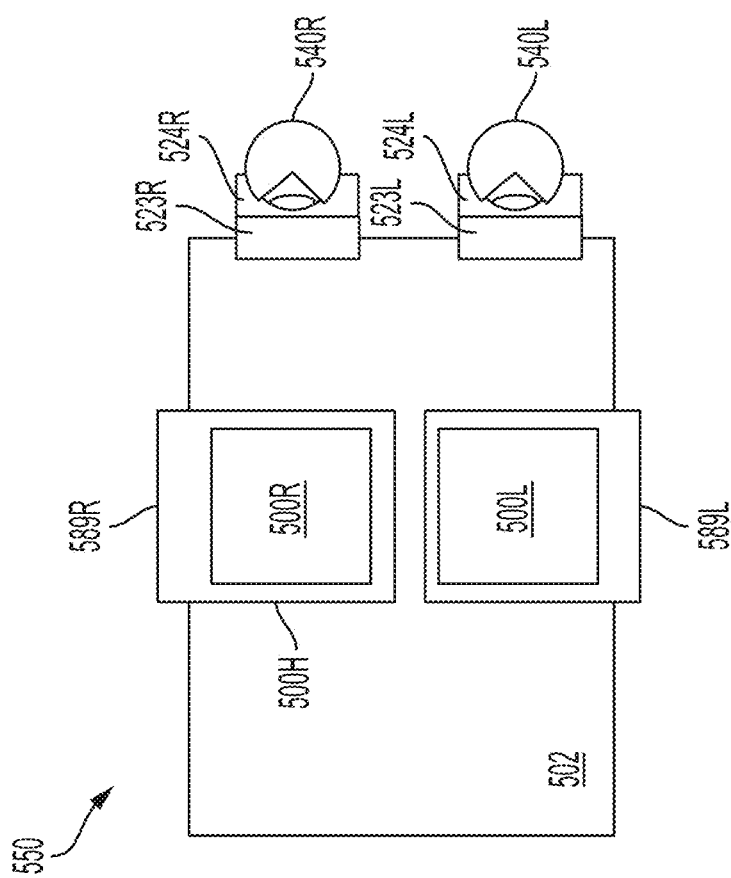
FIG. 5A is a high-level block diagram of an ophthalmic testing system according to some embodiments disclosed herein.

FIG. 5A is a high-level block diagram of an ophthalmic testing system 550 according to some embodiments disclosed herein. As noted, the ophthalmic testing system 550 can be implemented in a table-top device, a device capable of being worn by a test subject, and/or a device capable of being placed against the subject's head and/or face such that at least a portion of the device is disposed adjacent or against at least one eye of the subject (generally referred herein as a "head-wearable device").

The ophthalmic testing system 550 can comprise one or more receptacles 523R, 523L, each configured to receive at least one cartridge 500R, 500L. Each cartridge 500R, 500L can comprise at least one optical system having optical components for conducting various ophthalmic tests and measurements in accordance with the embodiments disclosed herein. Additionally or alternatively, each cartridge 500R, 500L can comprise other elements, such as digital electronic circuitry and hardware 300 that can be used with, incorporated in, or fully or partially included in an ophthalmic testing and measurement system according to the embodiments disclosed herein.

The ophthalmic testing system 550 can generally include any suitable number of receptacles 523R, 523L and can be configured to receive any suitable number of cartridges 500R, 500L. For example, as shown in FIG. 5A, the ophthalmic testing system 550 can comprise two receptacles 523R, 523L, each configured to receive at least one cartridge 500R, 500L. Each receptacle 523R, 523L can be configured to receive the at least one cartridge 500R, 500L removably and replaceably.

The cartridge(s) 500R, 500L can be mounted and received by the ophthalmic testing system 550 (within the housing of a tabletop device and/or in the headset 502 of a head-wearable device) via any suitable means known in the art. For example, each cartridge(s) 500R, 500L can be a removable and/or replaceable system that is configured such that it can be inserted into and removed from the ophthalmic testing system 550 through the receptacle(s) 523R, 523L. The cartridge(s) can further be replaceable and configured such that upon removal from the frame 502 of the ophthalmic testing system 500, they can be replaced with one or more other cartridges.

Each cartridge 500R, 500L can comprise a housing 550H. The housing 550H can include any suitable component known in the art and comprise any suitable shape and/or material. For example, each cartridge 500R, 500L can be sized and/or shaped to ensure that the cartridge 500R, 500L can be received by/fit into a corresponding receptacles 589R, 589L of the ophthalmic testing system 550. In some embodiments, the receptacles 589R, 589L can be configured such that they can receive cartridge(s) 500R, 500L having a predetermined standardized shape and/or size.

Further, inn some embodiments, at least one interface 523R, 523L can be configured to receive a light seal 524R, 524L that is configured to seal an eye of the subject that is interacting with or engaged by the interface 523R, 523L from ambient light. For example, an interface 523R can receive a light seal 524R that seals a corresponding eye 540R of the subject from ambient light.

Figure 5B:
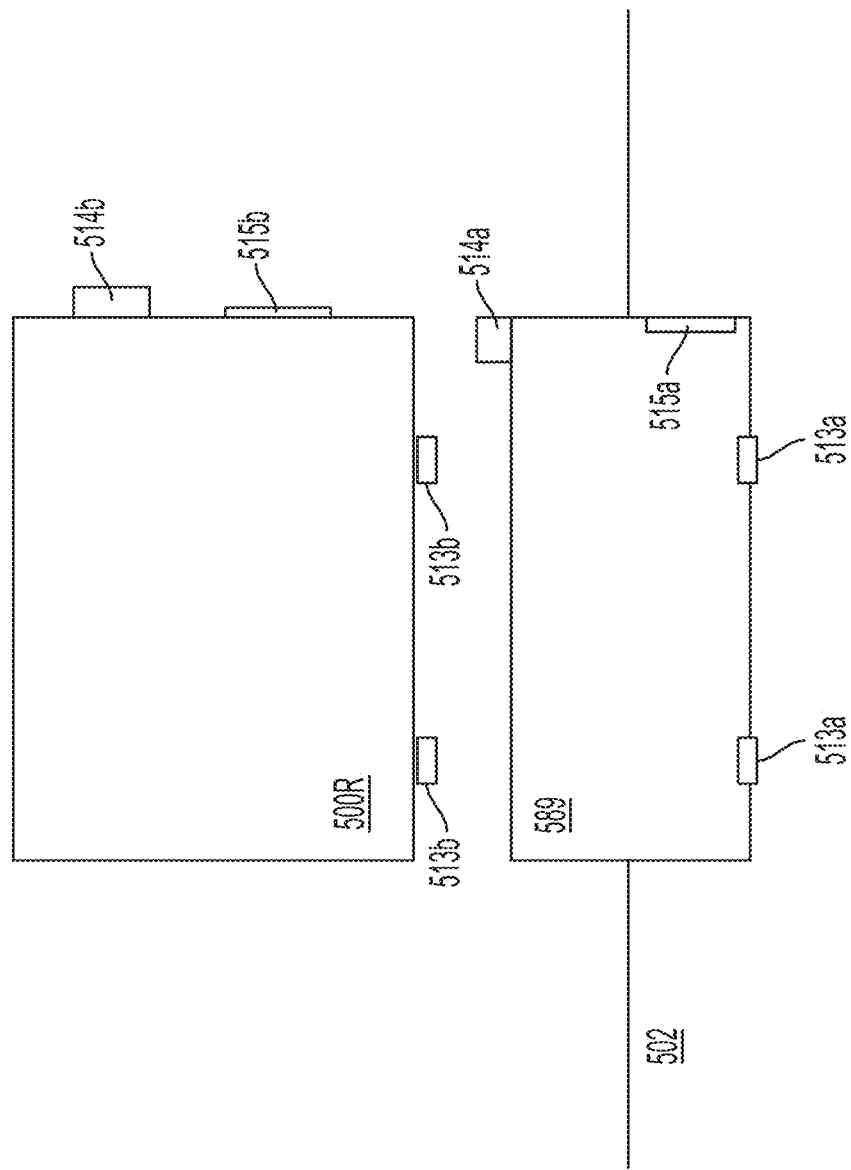
FIG. 5B is another high-level block diagram of an ophthalmic testing system according to some embodiments disclosed herein.

The ophthalmic testing system 550 can also comprise any suitable component for receiving the cartridge(s) 500R, 500L. For example, as shown in FIG. 5B, the ophthalmic testing system 550 can include one or more connections 513a (e.g., electrical connections) that are configured to couple with one or more corresponding connections 513b (e.g., electrical connections) on the cartridge. Specifically, each cartridge 500R can comprise one or more ports 513b that are configured to couple with one or more corresponding connections 513a in the receptacle 589 of the ophthalmic testing system 550. The corresponding ports and connections 513a, 513b can be configured such that upon being coupled to one another they connect the cartridge 500R to the ophthalmic testing system 550 such that the components in the cartridge 500R can be used with the ophthalmic testing system 550 to provide ophthalmic testing and measurement. The ports and connections 513a, 513b can comprise any suitable connection known in the art. For example, the ports and connections 513a, 513b can comprise sockets, male and female electrical and/or data connectors, USB ports and connectors, audio or video connectors, and/or any suitable connector available in the art.

Additionally or alternatively, the receptacles 589R, 589L and cartridges 500R, 500L can have one or more electrical contacts (e.g., gold dots) configured to facilitate communication of operating instructions, drivers, automated sequencing, data, etc. between the cartridge 500R, 500L and their components and the main operating system or firmware of the ophthalmic testing system 550. Further, as detailed below, the cartridge 500R, 500L can contain all the necessary hardware and software required to conduct the given ophthalmic test. Additionally or alternatively, the cartridge 500R, 500L can rely upon the components (e.g., optical components and/or digital circuitry) to some extent for both hardware and software support to supplement aspects of the test function.

The cartridge(s) 500R, 500L and/or the receptacle(s) 589L, 589R can further include one or more locking mechanisms 514a, 514b configured to lock a cartridge 500R in place once coupled to a corresponding receptacle 589L, 589R. The locking mechanisms 514a, 514b can be any suitable locking mechanisms known and available in the art. For example, in some embodiments, the cartridge(s) 500R, 500L can be configured to click and lock into a corresponding receptacle 589L, 589R.

Additionally or alternatively, the cartridge(s) 500R, 500L and/or the receptacles 189 can include one or more tracking systems 515a, 515b, such as a radio frequency identification (RFID) tag or a barcode. The one or more tracking systems 515a, 515b can be configured to provide asset tracking. For example, the cartridge(s) 500R, 500L and/or the receptacle(s) 589R, 589L can include one or more tracking systems 515a, 515b configured to ensure that only systems, equipment, and/or parts produced by original equipment manufacturer (OEM) are used in the ophthalmic testing system 550. Specifically, each of the cartridge(s) 500R, 500L and the receptacle(s) 589R, 589L can include corresponding tracking systems 515a, 515b (e.g., barcodes, RFID tags) that are configured to only allow the cartridge(s) 500R, 500L produced by OEM to be received by the receptacle 589R, 589L. In some embodiments, the tracking system 515a disposed on the receptacle 589R, 589L can be an RFID reader that is configured to read the information stored on a passive tracking system (RFID tag) 515b disposed on a cartridge 500R, 500L.

The tracking system 515a can be coupled to a processor (e.g., processor 310 of the digital circuitry 300 of the ophthalmic testing system) directly or indirectly (e.g., through an I/O interface 349). The RFID reader 515a can be configured such that upon scanning an RFID tag 515b (or a barcode or an OCR code, hereinafter generally referred to as "RFID tag"), the RFID reader sends the information stored in the RFID tag 515b to the processor for processing. The processor 310 processes the information and determines whether the information on the RFID tag 515b corresponds to an RFID tag recorded on an original manufacturer's disposable.

The cartridge(s) 500R, 500L can generally comprise any parts and connections necessary for conducting ophthalmic tests and/or measurements. Further, the ophthalmic testing system 550 can be generally configured such that it can receive cartridge(s) 500R, 500L capable of conducting any suitable ophthalmic tests and/or measurements. For example, ophthalmic testing system 550 can be configured to provide visual function testing using one or more cartridge(s) 500R, 500L capable of conducting a visual field test for detection of a disease or condition, such as glaucoma. Alternatively or additionally, the ophthalmic testing system 550 can be a system configured to receive cartridge(s) used for performing fundus retinal imaging, visual field test, Frequency Doubling Technology Perimetry (FDT), Electroretinogram (ERG), Visual Evoked Potential (VEP), Contrast Sensitivity, Color Vision, Visual Acuity tests including: High luminance/High contrast, Low luminance/High contrast, Low luminance/Low contrast, High luminance/Low contrast, Opotype, vernier acuity, Reading Speed tests in high & low luminance, Glare Testing (e.g., for cataract detection), Motion Perception, Metamorphopsia (e.g., in late AMD), Shape and Texture Discrimination (e.g., in late AMD), Mesopic and Scotopic Visual Fields, Photostress, Microperimetry (Fundus-guided Microperimetry), Tonometer, Stereopsis, Corneal Hysteresis. These examples are non-limiting examples of the tests and/or measurements that can be performed using the embodiments disclosed herein.

Further, the cartridge(s) 500R, 500L can be configured such that a given cartridge can be placed on either a left or a right receptacle 589R, 589L for testing the right and/or the left eye of the subject. Further, the ophthalmic testing system 550 can be configured such that it can receive two cartridge(s) 500R, 500L capable of conducting two different optical tests. The two different cartridge(s) 500R, 500L can provide the ophthalmic testing system 550 with the capability to conduct a different test on each eye simultaneously or in parallel.

In some embodiments, depending on the tests provided by the cartridge(s) 500R, 500L, one or more rules can be enacted to prevent right and left cartridge(s) 500R, 500L from operating simultaneously, where false positive or false negative results or no results can be obtained from having two different tests simultaneously. The one or more rules can be enacted in response to the nature of the tests or screens provided by the cartridge(s) 500R, 500L. Rules governing and controlling simultaneous test functions or simultaneous bilateral eye testing can be integrated in the system to prevent the occurrence of test faults. Simultaneous test rules can require sequenced testing of each eye independently when it is deemed that the subject cannot accurately respond to simultaneous stimulus presentation or other test interface. Additionally, each optical system can be configured to provide the test subject with relevant automated instructions (instructions relevant to the test provided by that optical system) to provide the test subject with active and responsive ontology guidance during the ophthalmic testing.

Figure 5C:
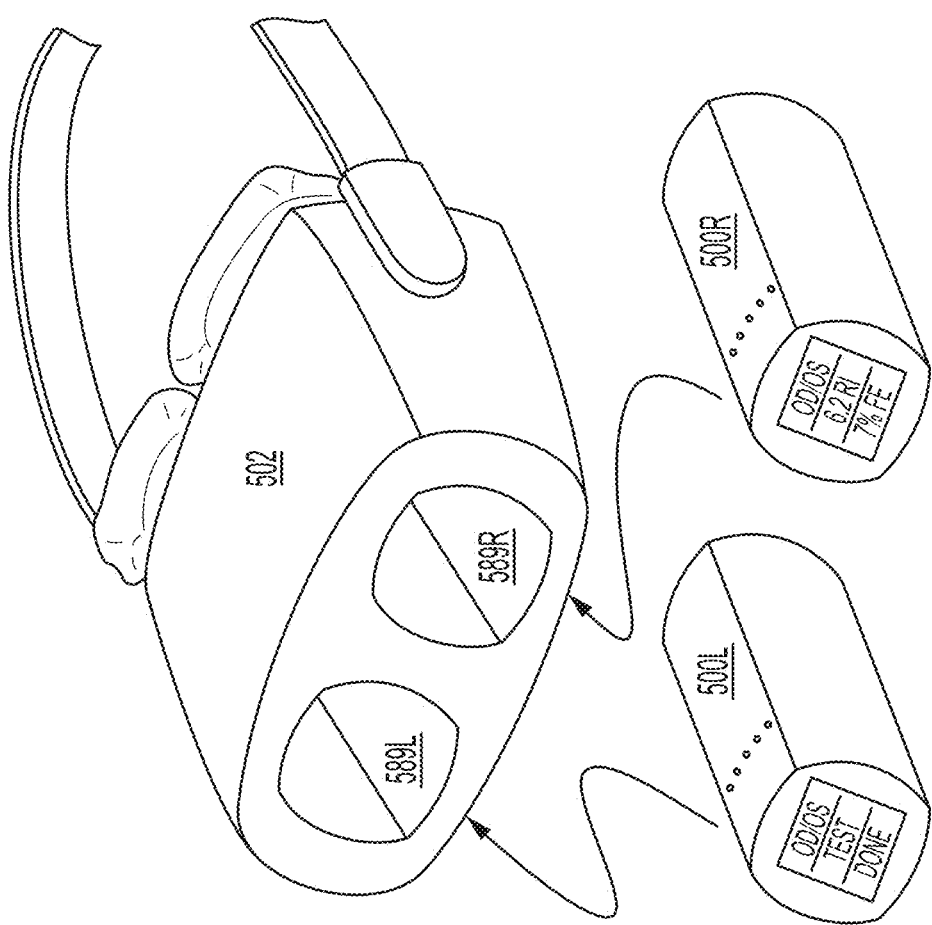
FIG. 5C schematically illustrates an example of a head-wearable implementation of an ophthalmic testing, measurement, detection, and/or diagnosis system according to some embodiments disclosed herein.

FIG. 5C illustrates an example of an ophthalmic testing system 550, as implemented in a head-wearable frame 502, having similar components as the head-wearable device shown in FIG. 1A. As shown, the frame 502 of the head-wearable device can include one or more receptacles or chambers 589L, 589R configured to receive one or more cartridges 500L, 500R. The cartridges 500L, 500R can be configured such that they seal the receptacles 589L, 589R and the internal elements of the headset 502 against the external environment.

In some embodiments, at least one cartridge 500R, 500L can be configured as a light seal having components that are configured to seal the subject's eye from ambient light. For example, a cartridge 500R can comprise at least one material capable of having an adjustable opacity and/or a material configured to have an adjustable opacity in response to a stimulus (e.g., illumination at certain light frequencies or intensities). In some embodiments, the material having adjustable opacity can comprise one or more polarized filters and/or one or more liquid crystal layers.

Figure 6:
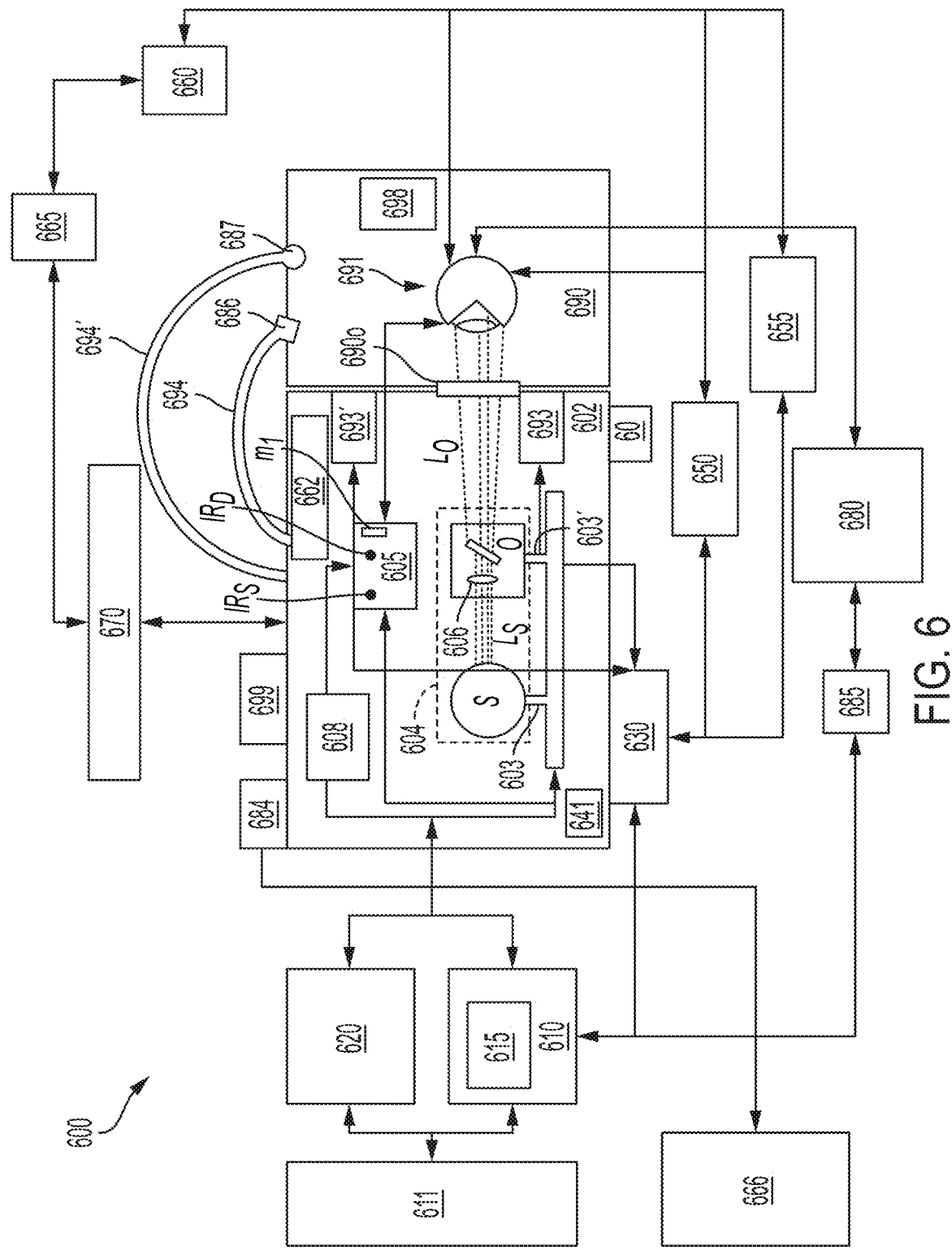
FIG. 6 is a block diagram of an embodiment of an ophthalmic testing system and measurement system.

FIG. 6 is a high-level block diagram of an embodiment of an ophthalmic testing system and measurement system 600 ("system 600") according to some embodiments disclosed herein. In one embodiment, the system 600 can be configured to measure a subject's eye's adaptation to darkness. This can be performed by bleaching a region of the subject's retina and subsequently presenting a stimulus light (e.g., in the form of an image) having a lower intensity within the bleached region of the retina. Throughout the test, the subject is directed to fixate their gaze on a fixation light and press a button when they recognize the stimulus light.

The testing system 600 can comprise a frame 602 that is configured to house various components of the system. The frame 602 can comprise an optical system (described with reference to FIG. 2) that comprises the required optical components for conducting various ophthalmic tests and measurements with the embodiments disclosed herein, and digital electronic circuitry and hardware (described with reference to FIG. 3) that can be used with, incorporated in, or fully or partially included in an ophthalmic testing and measurement system 650 according to the embodiments disclosed herein. It should be noted that although certain elements of the system 600 are shown as being inside or outside of the frame, the arrangement shown in FIG. 6 is a non-limiting example and the components of the system 600 can be disposed in any suitable location, including within, on, or outside of the frame 602 of the system 600.

As described with reference to FIG. 2, the system 600 can comprise a mechanism 601 for controlling the light source S and/or the optical components O. The mechanism 601 can include one or more platforms 603, 603', on which the light source S and/or the optical components O are mounted. The platforms 603, 603' can be movable and configured such that they allow movements of light source S and/or the optical components O within the system 600 and relative to a frame 602 (and/or the frame of the optical system 612). For example, the platforms 603, 603' can be movable along at least two orthogonal directions for aligning the light source S relative to the pupil of the subject's eye 691. Additionally or alternatively, the platforms 603, 603' can be fixedly positioned relative to the frame 602.

The ophthalmic testing system 600 can further comprise one or more optical components (collectively referenced using reference character O) that are configured to direct the light beams emitted by the light source S to the pupil of a subject's eye. Further, in some embodiments, the optical components can be configured such that they direct the light beams emitted by the light source S to retina of at least one eye of a test subject. The optical components O can include any suitable optical elements available in the art. For example, the optical components O can comprise at least one lens 606 that is optically coupled to the light source S and configured to collimate the light beams emitted by the light source S. The lens 606 can comprise at least one aspheric lens 606 adapted to correct for spherical aberration. Additionally or alternatively, the optical components O can include one or more mirrors 607 that are configured to redirect the light beams emitted by the light source S as needed. For example, as described in further details below, the one or more mirrors 607 can be configured to direct the light emitted by the test light source onto a test subject's eye. The one or more mirrors 607 can comprise a dichroic mirror that is configured to reflect the light from the test light source S onto the subject's pupil and allow passage of the infrared light returning from the subject's eye into the ophthalmic testing system 600 (e.g., an infrared light detector $IR_D$ discussed below). By way of example, the infrared light can have a wavelength of greater than about 700 nanometers.

Additionally or alternatively, the optical system 612 can include one or more tracking systems 615, such as a radio frequency identification (RFID) tag or a barcode. The one or more tracking systems 615 can be configured to provide asset tracking. For example, the optical system 612 can include one or more tracking systems 115 configured to ensure that only systems, equipment, and/or parts produced by original equipment manufacturer (OEM) are used in the ophthalmic testing system 600. Specifically, each of the optical system 612 can include corresponding tracking systems 615 (e.g., barcodes, RFID tags) that are configured to only allow optical systems produced by OEM to be used with the system 600.

In some embodiments, the light source S and/or the optical components O can be housed in a sealed package 604. The sealed package 604 can be an integral part of the optical system 612 or can be configured such that it is removably and replaceably mounted within the optical system 612 to provide for removal and/or replacement of the optical components O.

As noted, the mechanisms 601 for controlling the light source S and/or the optical components O can further include one or more dials/knobs 699 adapted to be rotated by a user and a cam system mechanically coupled to the knob and configured to transform the rotational motion of the knob into linear translation of the light source S. The one or more dials 699 can be configured for use in adjusting a viewing distance of an image plane provided by the headset. As described with reference to FIG. 1A, the knob or dial 699 can be used to manually adjust a fixation light source S. Specifically, the dial 118 can be connected to the fixation source $S_f$ and configured to move the fixation source in an axial direction relative to the subject's eye(s). By moving the fixation source $S_f$ relative to the subject's eye(s), the dial 118 can bring the fixation source $S_f$ in focus and/or compensate for possible reflective errors (e.g., nearsightedness (myopia), farsightedness (hyperopia), astigmatism or presbyopia) in the subject's eyes. The dial 118 can be configured such that it can be adjusted by the test subject and/or by the technician/clinician delivering the ophthalmic test to the subject.

Generally, the light source S can be configured such that it is movable in one or more directions. Further, the light source S can be configured to direct fixation lights emitted by the light source S out of the frame 102 such that it brings the subject's attention to the light source S. The light source S can also be movable such that it brings the fixation light into focus when viewed by the subject. Alternatively or additionally, the light source S can be movable in a direction substantially along a propagation direction of the fixation light emitted by the light source S.

As described with reference to FIG. 2F, the system 600 can further comprise an automated pupil tracking mechanism 605 that is configured to align and/or adjust the position and/or orientation of the light source S and/or the optical components O relative to the pupil of the subject's eye 691. The automated pupil tracking mechanism 605 can be coupled to the light source S, the optical components O, and/or the platform 601 and configured such that it aligns at least one of these elements with the pupil of the subject's eye 691. The automated pupil tracking mechanism 605 can further be configured such that upon placement of the ophthalmic testing system 600 against a subject's eye 691, it can automatically detect the position and/or size of the pupil of the subject's eye 691, and, in response, align at least one of the light source S, the optical components O, and/or the platform 601 to the pupil of the subject's eye 691.

As noted above, the automated pupil tracking mechanism 605 can include a light source (e.g., a visible light source or an infrared light source) $IR_S$ and a light detector (e.g., a camera, a light detector or camera capable of detecting visible light, an infrared light detector, or an infrared camera) $IR_D$. The light detector $IR_D$ can comprise a camera that is configured to generate an image of the subject's pupil based on the light returning from the at least one eye 691 of the subject. The light source $IR_S$ can be configured such that it illuminates the subject's eye 691.

A portion of the light incident on the subject's eye is reflected and returns to automated pupil tracking mechanism 605. The light detector $IR_D$ can detect the returned light and determine the position and/or size of the pupil of the subject's eye 691 based on the detected returned light. In some embodiments, the light source $IR_S$ can generate light, e.g., at a wavelength greater than about 700 nm for illuminating the subject's eye. Further, as shown in FIG. 6 and detailed above, a mirror $m_1$, which can be a dichroic mirror, can be configured to reflect the visible light generated by the test light source S and allow the passage of the light returning from the subject's eye in response to illumination by the light source from the test light source S. The light detector $IR_D$ can be mounted in any suitable position on the frame 602 (e.g., rear of the optics), behind the dichroic mirror $m_1$, and configured to detect and/or image the light returning from the illuminated eye and passing through the dichroic mirror $m_1$.

As noted above, any suitable mechanisms for tracking a subject's eye or pupil can be employed with the embodiments disclosed herein. Further, in some embodiments, a controller 610 can be in communication with the detector $IR_D$ to receive electrical signals generated by the detector $IR_D$ in response to the detection of the infrared radiation returning from the subject's eye 691. The controller 610 can be included on the frame 602 and/or remotely coupled to the system 600.

The controller 610 can be configured to determine the relative alignment of the source $IR_S$ with respect to the pupil of the subject's eye 691. More specifically, the controller 610 can operate on the electrical signals generated by the detector $IR_D$ to generate an error signal, whose magnitude is indicative of the degree of misalignment between the infrared source $IR_S$ and the subject's pupil.

If the error signal generated by the controller is greater than a predefined threshold, the controller 610 can cause the movement of the movable platforms 603, 603' to minimize the error signal, thereby bringing the source S in substantial alignment with the subject's pupil. As the light source S (e.g., the light source that generates the bleaching light, the stimulus light, as well as the fixation light) is fixedly positioned on the platform 603, 603', movement of the platform 603, 603' relative the subject's pupil can result in substantial alignment of the light source S relative to the subject's pupil.

The system 600 can further comprise a user interface (subject-response interface) 680 configured for use by the subject to provide the system 600 with feedback in response to the ophthalmic test or measurement being conducted. The subject-response interface 680 can comprise any suitable interface available in the art. For example, the subject-response interface 680 can be a touch sensitive button, a push button, a five-way rocker button, and/or a traditional computer mouse. The subject-response interface can be coupled with a response analyzer 185 that is configured to analyze and assess the subject's response/feedback received through the subject-response interface 680. For example, in one embodiment, the response analyzer 685 can be configured to analyze the feedback of the subject for assessing dark adaptation of at least one eye of the subject. The analyzer can include a processor (e.g., processor 310 shown in FIG. 3A) and a memory (e.g., memory 320) coupled with the processor and configured to store instructions for analyzing the response of the subject (e.g., response to a stimulus light in analyzing dark adaptation).

The infrared light source $IR_S$ and the infrared light detector $IR_D$ of the pupil tracking mechanism 605 can be disposed on any suitable position in the housing 602, such as on the light seal 690, on the wall of the rear housing inside the eye chamber including the rear housing, eye cups, and/or on the disposable light seal, adjacent to the eye. An RFID tag 698 can be incorporated in the light seal 690. The RFID tag 698 can be coupled to the light seal 690 in any suitable known manner. The RFID tag 698 can comprise any suitable tag known in the art. As noted above, in some embodiments, the light seal 690 can comprise a disposable, removable, and/or replaceable layer that is positioned on an external portion of the light seal 690 (e.g., on a surface of the light seal that comes in contact with the subject's face/eye). The RFID tag 698 can be incorporated in the disposable layer of the light seal 690 to ensure that the disposable layer 692 is an authentic disposable and also to enforce single usage of the disposable layer.

As detailed above, any suitable technique can be employed for operating on the detected signals and arriving at a degree of alignment of the light source relative to the subject's pupil. Further, upon the detection of a misalignment of the light source relative to the subject's pupil, the controller 610 can cause the movement of the movable platforms 603, 603' via a feedback loop to bring the light source S and/or the optical components O, in substantial alignment relative to the subject's pupil. More specifically, in some embodiments, the controller 610 can actuate various means (e.g., motors) for moving the movable platform along X, Y and Z directions.

Further, during the performance of an ophthalmic test, the alignment mechanism 605 can continuously track the position of the subject's pupil and continuously correct for any misalignment of the light sources relative to the subject's pupil. In this manner, the alignment mechanism can correct, for example, for involuntary movements of the subject's eye, vibrations and other unwanted motions of the optical system, among others.

In some embodiments, the pupil(s) of the subject's eye(s) can be dilated prior to using the system 600. The automated pupil tracking mechanism 605 can be configured to correct for the subject's pupil size and for any changes induced in the subject's pupil(s). The automated pupil tracking mechanism 605 can provide the corrections in real time. Alternatively or additionally, the pupil tracking mechanism 605 can be configured to correct for the position of the subject's upper and/or lower eye lids and/or eyelashes in correcting for and determining the subject's pupil size or position. Further, in correcting for the subject's pupil size, the system 600 can adjust the intensity of the stimulus and/or the bleaching lights applied to the subject's eye. In other words, the system 600 can adjust the intensity of the stimulus and/or bleaching lights applied to the subject's eye based on the size of that subject's pupil(s).

The ophthalmic testing system 600 can also include a feedback system 608. The feedback system 608 can be coupled to the pupil tracking mechanism 605 (e.g., the infrared light source $IR_S$ and the infrared light detector $IR_D$) and/or the one or more mechanisms 601 for controlling the light source S and/or the optical system O. The feedback system 608 can be configured to detect the position of the pupil of the subject's eye 691 based on the signals generated by the infrared light detector $IR_D$ and/or receive the position of the pupil of the subject's eye 691 from the automated pupil tracking mechanism 605. The feedback system 608 can use the position of the pupil of the subject's eye 691 to cause the movement of the light source S and/or the optical system O through the mechanism 605 (e.g., using the platform 603, 603') and direct and align the light emitted by the light source S at the pupil of the subject's eye 691.

For example, the feedback mechanism 608 can align the light emitted by the light source S based on a shape of the subject's pupil in an image generated by an infrared camera of the infrared light detector $IR_D$. Specifically, the infrared light source IRs can include two or more spot light sources or an aperture configured to produce a known shape to direct toward the subject's eye. The reflection of the infrared light source IRs as captured by the infrared light detector $IR_D$ can be used to measure the distance between two or more infrared spot reflections or measure the size of an infrared shape reflection at the subject's eye. The measured dimension of the reflected infrared feature within the captured image can be used to determine the Z-position (horizontal position) of the eye as a distance away from the infrared light detector $IR_D$, and thus calculable the distance away from the optical system O.

Further, the measurements of infrared spot light reflections and/or infrared features can be used to self-calibrate the system, determine the subject's eye Z-position (horizontal position), and properly determine the subject's pupil size. Given that each subject can have her own unique facial features/dimensional anatomical features (i.e., eye position relative to the subject's head), by calibrating the system for each subject, embodiments disclosed herein can achieve more accuracy. Furthermore, as noted above, the feedback mechanism 608 can adjust the intensity of the test light source based on the size of the pupil of the subject's eyes.

As noted above, the system 600 can further comprise a light seal 690 configured to isolate at least one eye (e.g., the test eye 691) of the subject from ambient light. The light seal 690 can comprise one or more portions and/or elements, each of which can be reusable and/or disposable. For example, the light seal 690 can comprise one or more eye cups that are configured to surround the area around at least one eye of the test subject and seal the at least one eye from ambient light. The one or more eye cups can comprise any suitable material known in the art and can be reusable (can be used with multiple test subjects, does not need to be changed every time a new subject is tested, and/or can be cleaned before/after each use) and/or disposable. The light seal 690 can be attached to the frame 602 using any suitable means. For example, the light seal 690 can be inserted within a receptacle provided in the frame, glued to the frame, or attached to the frame using other suitable means of coupling.

Further, the light seal 690 can be configured such that it can isolate one or both eyes of the subject from ambient light. The light seal 690 can also be configured such that it can independently isolate each eye of the subject from ambient light (e.g., can provide a different, separate, or independent light seal for each eye). Generally, the light seal 690 can be configured according to any suitable technique and/or using any suitable materials available in the art informed by the present teachings. For example, the light seal 690 can comprise a conformable material (e.g., silicone) and/or be configured such that it is substantially conformable to at least a portion of the subject's head. Alternatively or additionally, the seal 690 can comprise a conformable body having at least one opening 690o configured to be substantially aligned with at least one eye 691 of the subject when the frame 602 is worn by the subject. The conformable body can be coupled to the frame 602 such that the combination of the frame 602 and the light seal 690 can isolate the eye 691 of the subject from ambient light when worn by the subject and/or placed adjacent to the subject's face or head.

The light seal 690 can include any suitable mechanism available in the art for adjusting the light seal around the subject's eye 691 and/or for attaching the conformable body of the seal 690 removably and replaceably around the subject's head. For example, the light seal 690 can include a ratchet 692, which can be mounted on the frame 602 and coupled to the light seal 690, and configured to adjust the light seal 690 around the subject's eye/head 691. Such isolation of the subject's eye(s) from the ambient light can be important in measurements of dark adaptation and also in performing various other ophthalmic tests and measurements, such as detection of vitamin A deficiency, Sorsby's Fundus Dystrophy, late autosomal dominant retinal degeneration, retinal impairment related to diabetes, diabetic retinopathy, drug induced retinal toxicity, glaucoma, ocular hypertension, retinal hypoxia, retinitis pigmentosa, and fundus albipunctatus.

Additionally or alternatively, an attachment mechanism 694 can mechanically couple the ratchet 692 to the light seal 690. The attachment mechanism 694 can be a strap that is configured such that it can be used to adjust at least one of a length and tension in the strap 694, and thereby adjust the light seal around the subject's eye 691. Additionally or alternatively, the attachment mechanism 694 can comprise at least one arm coupled to the conformable body of the seal 690. Further, an additional strap 694' can be coupled to the frame 602 of the system 600 and configured to adjust attachment of the frame 602 to the subject's head. A quick release button 686, 687 can be coupled to at least one of the straps 694, 694' to allow facile release of the straps 694, 694'. The straps 694, 694' can comprise any material known in the art, for example an elastic material.

It should be noted that, although shown as being separate from the frame 602, the one or more portions of the light seal 690 can be directly coupled to the frame 602 of the system 600, be removably coupled to the frame 602 of the ophthalmic testing system 600, be fixedly coupled to the frame 602 of the ophthalmic testing system 600, and/or be an integral part of the frame 602 of the ophthalmic testing system 600. Further, it should be noted that in order to ensure hygienic usage of the system, various portions of the system 600 that are expected to come in contact with the test subject's skin, body, hair, face, and/or eye can be lined with a removable, replaceable, and/or disposable layer and/or any suitable material that can be cleaned (e.g., using a medical grade cleaner) before/after use.

The system 600 can further comprise one or more sensors 693, 693'. For example, the system 600 can comprise at least one of: a pressure sensor, a capacitive sensor, and a light sensor. The one or more pressure, capacitive, and light sensors 693, 693' can be included at any suitable location within the system 600 and configured such that they can detect various conditions and status of the system. For example, the light seal 690 can comprise one or more light sensors 693 configured to detect passage/leakage of light through the light seal 690.

The system 600 can further comprise one or more pressure sensors 693 configured to ensure that appropriate contact between the system 600 (e.g., head-wearable device) with the subject's face, head, or eye(s) has been established. The sensors 693 can be disposed at any suitable location (on the light seal) within the system 600, for example on the headset and/or head strap of the head-wearable device.

Additionally or alternatively, the system 600 can include one or more motion sensors 641, 684 configured to track and/or monitor the motion and/or movement of the system 600 and/or the subject. For example, the system 600 can comprise at least one motion sensor 641 (e.g., comprising at least one of an accelerometer and/or a tilt sensor) that is configured to monitor, track, and/or collect information indicating sudden acceleration or deceleration of the system 600. It should be noted that the term "motion sensor," as used herein, is intended to refer to any type of sensor available in the art that can monitor, track, or be used to obtain information regarding motion, location, orientation, and/or position of any component of the ophthalmic testing system 600.

The information collected by the at least one motion sensor 641 can be used in monitoring the general status of the ophthalmic testing system 600. For example, in some embodiments, the system 600 can comprise a motion sensor 641 and/or an inertial measurement sensor (IMS) 693/641 that can be used to collect information regarding unexpected changes in the motion of the device and/or undesired events, such as whether the system 600 has been dropped (e.g., if a head-wearable implementation of the system has been dropped), whether the system 600 has taken any undesired impact, whether the system 600 has been transported from its intended usage facility (practitioners transporting a tabletop implementation between various facilities and possibly damaging the device in the process), etc. The information collected by the sensors 693/641 can be forwarded (e.g., via a processor 310 in the digital circuitry of the system) to an entity that tracks, records, and/or makes use of such information. For example, the information regarding unexpected motions of the device can be transmitted to an entity (e.g., original manufacturer) providing/offering warranties on the device. In this way, the system can automate possible responses to insurance and warranty damage claims made by users because it can track and identify damages that occurred due to user's own negligence (e.g., caused by dropping the device). Further, to ensure successful tracking of devices, the system can maintain its own backup power/battery source to ensure that tracking is accomplished even when the testing system is turned off.

It should be noted that although described with reference to motion and inertial measurement sensors, the ophthalmic testing system 600 can comprise any means for detecting occurrence of unexpected/undesired events in the ophthalmic testing system 600. For example, the ophthalmic testing system 600 can comprise at least one of a motion sensor, a temperature sensor, a humidity sensor, microphone, global positioning system (GPS), gyroscope, light sensor, infrared sensor, proximity sensor, system clock, and/or an accelerometer. The undesired events can also include any event that can be of interest to an authorized party (e.g., original manufacturer). For example, the undesired events can be an opening of a cover of the ophthalmic testing system. The sensors could be integrated into a single printed circuit board or dispersed throughout the testing system on multiple printed circuit boards.

The system 600 can further comprise a subject-instruction system 660 configured to provide the subject with instructions for conducting an ophthalmic test. The subject-instruction system 660 can allow an authorized party (e.g., a medical professional) to communicate with a subject during the ophthalmic test or measurement. For example, the subject-instruction system 660 can be used by a medical professional to provide instructions and/or feedback to a subject undergoing an ophthalmic test or measurement. The subject-instruction system 660 can generally utilize the processor 310, and other elements of the digital circuitry of the system 600 (e.g., at least one random access memory (RAM), permanent memory, communication interface 340, a speaker 467, and appropriate connections (e.g., bus)) that allow the processor 610 to communicate with various components of the system 600, to receive instructions from a medical professional, provide responses, and/or request for assistance/guidance.

In some embodiments, the subject instructions system 660 can issue one or more commands for directing the test subject through the test environment (e.g., testing room). The one or more commands for guiding the test subject include at least one of 1) address or location of an exam room in which the ophthalmic test is administered, 2) information regarding the ophthalmic test, and 3) expected wait time until the ophthalmic test is administered.

The system 600 can further comprise a monitoring system 665 for monitoring at least one attribute of at least one eye of the subject (e.g., measurement of dark adaptation). The monitoring system 665 can be in communication with the automated subject-instruction system 660 and configured to cause the subject-instruction system 660 to provide one or more instructions to the subject in response to monitoring of the at least one attribute of at least one eye of the subject. For example, the monitoring system 665 can utilize the subject-instruction system 660 to provide instructions to the test subject regarding the attribute(s) being monitored. The monitoring system can provide these instructions via the interfaces included in the system 600, for example using audio instructions provided through the speaker 467/650.

The speaker 650 can be coupled with the monitoring system 665 and subject-instructions system 660 and configured to provide the subject with instructions (audio communication) for monitoring the at least one attribute. For example, the speaker 650 can be configured to receive instructions signals from the monitoring system 665 and subject-instructions system 660 and convert these signals into audio signals and provide the subject with audio instructions that direct the test subject to focus her gaze on the fixation light, instructions that direct the test subject to continue responding to the stimulus light, information regarding the amount of time remaining in the test, etc.

Specifically, as detailed below, the monitoring system 665 and the subject-instruction system 660 (e.g., an automated subject-instruction system) can be connected to at least one processor (e.g., processor 310) and configured to send and receive signals to/from the processor. The monitoring system 665 can monitor various attributes of the test (e.g., a subject's response to a stimulus) and send information regarding that attribute (e.g., the subject's response and/or whether the subject continues to provide a response) to the processor. The processor can process the information received from the monitoring system 665 and determine whether any information should be provided to the subject and/or the subject should receive instructions as to how to continue with the remainder of the test (e.g., whether the subject should be instructed to focus her gaze). Upon determining that certain instructions should be provided to the subject (e.g., instructions to continue to focus gaze, instructions to continue to provide responses), the processor can access at least one random access memory module (RAM) or a permanent memory module (e.g., memory 320) and identify at least one relevant form of audio file (e.g., in the form of Waveform Audio File Format) that can be used to provide those instructions to the test subject (e.g., identify an audio file that includes commands for instructing the subject to focus her gaze). The processor can obtain the identified audio files from the memory and cause the execution of the files by instructing the speaker 650 to play the audio files for the test subject. The audio signals can be provided in the form of natural language/verbal commands.

Additionally or alternatively, the automated subject-instruction system 660 and/or the monitoring system 665 can be coupled to a display 670 and configured to display the relevant information and instructions (e.g., subject instructions) for use by the provider (e.g., technician) conducting the ophthalmic testing and measurement. For example, the display 670 can provide the technician with comments (focus your gaze) and prompt the subject to provide the instructions (e.g., reading out the instructions) to the test subject.

Further, the system 600 can comprise an alert mechanism 630 that can provide an alert signal to the subject and/or the practitioner in response to the information provided by the monitoring system 665 and/or the resulting instructions provided by the automated subject-instruction system 660. The alert mechanism 630 can further be configured such that it monitors the one or more sensors 693, 693' and in an event a irregularity or an undesired condition in the contact between the light seal 690 and the subject's face, head, or eye(s) is observed, generate an alert that notifies an operator of the detected conditions. For example, in some embodiments, the monitoring system 665 can monitor the information received from the sensors 693/641 to determine if there is leakage of light through the light seal 690 (based on information received from a sensor monitoring the light seal) and/or if the subject has moved (based on information received from inertial and/or motion sensors) and upon observing such conditions alert the practitioner and/or the subject of these conditions. The alert mechanism 630 can provide the alert signals to the subject and/or clinician via any suitable interface, for example by providing audio signals (e.g., verbal signals) via the speaker 650 and/or visual signals via the display 670.

Moreover, the alert mechanism 630 can be configured to generate an alert in an event a light sensor 693, 693' detects a possible light leakage through the light seal 690. For example, the alert mechanism can be configured to generate an alert in an event passage of light having an intensity greater than 0.005 Scotopic $$\frac{Cd}{m^2}$$

is detected in the light seal 690. The alert system/alert mechanism 630 can further be configured to identify the eye of the subject, in vicinity of which the light leakage is detected. For example, the alert system 630 can be configured to generate an audio alert in response to the detection of the light leakage.

Alternatively or additionally, the alert mechanism 630 can be configured to inform an individual administering the ophthalmic testing and measurement using the system 600 that the ophthalmic testing and measurement is complete. For example, as shown in FIG. 4C, in one embodiment, the alert mechanism 630 can be configured to inform an individual administering a Rod Intercept™ (RI™) test for measurement of dark adaptation using the system 600 that the test is complete and/or if a malfunction has occurred. As shown, the alert mechanism 630 can inform the individual administering the dark adaptation test by generating and/or issuing an alarm signal (e.g., a visual signal as shown in FIG. 4C). The alarm signal can indicate to the individual that the test has been completed and/or that a malfunction (e.g., fixation error) has occurred.

As noted with reference to FIG. 4A, the system 600 can comprise a user interface (subject-response interface) 680 configured for use by the subject to provide the system 600 with feedback in response to the ophthalmic test or measurement being conducted. The subject-response interface 680 can comprise any suitable interface available in the art. For example, the subject-response interface 680 can be a touch sensitive button, a push button, a five-way rocker button, and/or a traditional computer mouse. The subject-response interface can be coupled with a response analyzer 185 that is configured to analyze and assess the subject's response/feedback received through the subject-response interface 680. For example, in one embodiment, the response analyzer 185 can be configured to analyze the feedback of the subject for assessing dark adaptation of at least one eye of the subject. The analyzer can include a processor (e.g., processor 310) and a memory (e.g., memory 620) coupled with the processor and configured to store instructions for analyzing the response of the subject (e.g., response to a stimulus light in analyzing dark adaptation).

Further, as also noted with reference to FIG. 4A, the ophthalmic testing and measurement system 600 can further include a provider interface 611 that can be directly included in the frame 602, coupled to the frame 602, and/or positioned remotely from the frame 602 of the system 600. The provider interface 611 can be configured to be used by a clinician or technician to provide data (e.g., adjustment data) or test interpretation and outcome and/or collect and report information (e.g., test results).

Further, the provider interface 611 can be configured to communicate with an electronic health record (EHR) or practice management system (e.g., to provide structured file data thereto). Such structured file data can be stored in a shared folder that can be accessed by multiple entities. The communication center 610 can employ encryption for such communication.

In some embodiments, the system 600 can also comprise a command center 666 that is configured to control functions of the system 600, such as initiating an ophthalmic test, terminating an on-going ophthalmic test, provide verbal and/or visual commands to one or more subjects wearing the head-wearable devices, etc. In some implementations, the command center 666 can be a mobile device and/or implemented in a mobile device, e.g., an Ipad®, and Iphone®, or similar devices. In some embodiments, the command center 666 can be positioned remotely from the frame 602 of the system 600 and configured to communicate with the system 600 using any suitable communication protocol including wireless communications protocols, such as Bluetooth®, Wi-Fi, or others.

It should be noted that although described as separate components, the various components of the system 600 can be implemented as parts of the same device or system. For example, as described with reference to FIG. 4A, the interface unit 460 can be configured to function as both a subject-response interface and a provider interface and also provide at least some of the functions provide by the command center 666.

Alternatively or additionally, the system 600 can comprise a call button 699, which can be used by subject to communicate with the individual administering an ophthalmic test (e.g., via sending an alert signal to that individual). For example, the call button 600 can be configured to allow a test subject to have a dialogue with an individual administering an ophthalmic test.

Additionally or alternatively, the system 600 can include a power indicator and/or a power switch 60. The power indicator 60 can be coupled to the 102 and configured such that it can be used to power on and/or power off the system 600 and/or indicate the power status of the system 100 (e.g., whether the system is on or off, the amount (percentage) of battery remaining/consumed in, for example, the head-wearable implementation). It should be noted that the power switch 60 can be incorporated in, integrated in, and/or be parts of any other part of the system 600.

Figure 7:
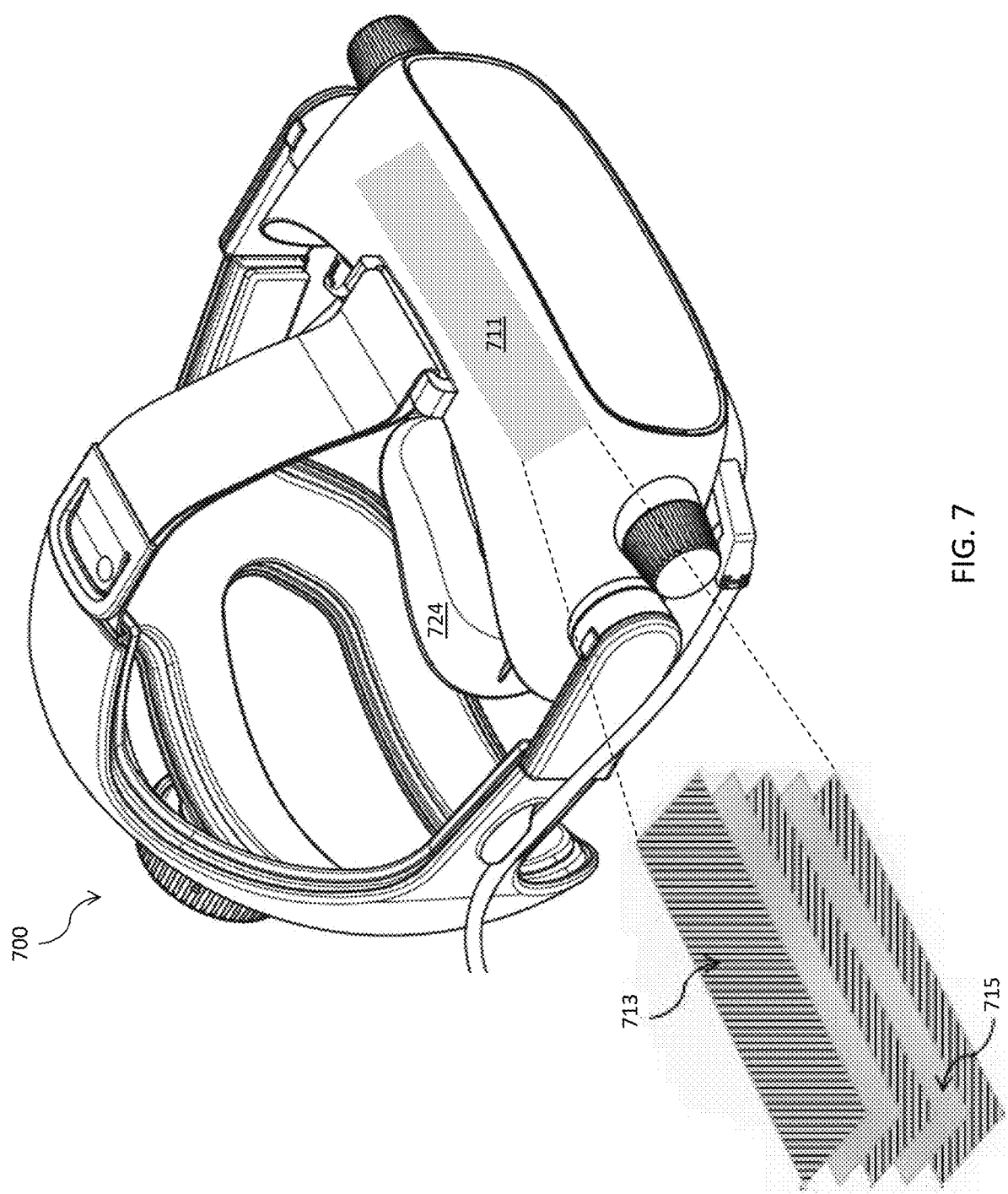
FIG. 7 is a schematic illustration of a head-wearable device according to embodiments disclosed herein.

FIG. 7 is a schematic illustration of a head-wearable device 700 according to embodiments disclosed herein. As noted with reference to FIG. 1A, the head-wearable device 700 can comprise one or more light seals 724R, 724L configured to isolate the optical interface of the head-wearable device 700 and at least one eye (e.g., a test eye) of the subject from ambient light. Additionally or alternatively, in some embodiments, the head-wearable device 700 can be configured such that at least a portion of the headset 202 comprises an opaque region configured to obstruct passage of ambient light to the subject's eye. For example, as shown in FIG. 7, the head-wearable device 700 can comprise at least one opaque portion 711. The opaque portion 711 can comprise a material having an adjustable opacity. For example, the opaque portion 711 of the head-wearable device can comprise a material having an opacity that is adjustable in response to a stimulus.

In some embodiments, the opaque portion 711 can be a liquid crystal that is configured to transition from translucent to opaque upon application of a voltage thereto. Specifically, at least a portion of the opaque region 711 can comprise one or more layers of liquid crystal cells 715 and one or more layers of a light polarizer 713 (e.g., polarized filters) that are configured to achieve a transition between opacity and translucence in response to application of one or more voltages thereto. This configuration can provide more comfort to subjects who may have difficulty with being in a dark environment because it allows the opaque portion 711 of the head-wearable device 700 to gradually transition from being translucent to being fully opaque, thereby providing the test subject with some time to adjust to the environment (after wearing the head-wearable device) before the head-wearable device completely blocks the light passing to the subject's eyes.

The polarized filters 713 can be configured such that they are offset at a predetermined orientation to the underlying filters 215 and are interlayered with the liquid crystal cell layers. For example, in some embodiments, the polarized filters can be offset at about 90 degrees relative to the underlying layers. Since the stimulation of the liquid crystal cells by electricity can change the refraction angle of light passing through the liquid crystal cell layers, the polarized filters and the liquid crystal cell layers can be combined and stacked such that they provide a change the opacity of the opaque portions 711 and prevent passage of the light through the opaque portions 711 (or allow the light to pass through the opaque portions 711).

Figure 8:
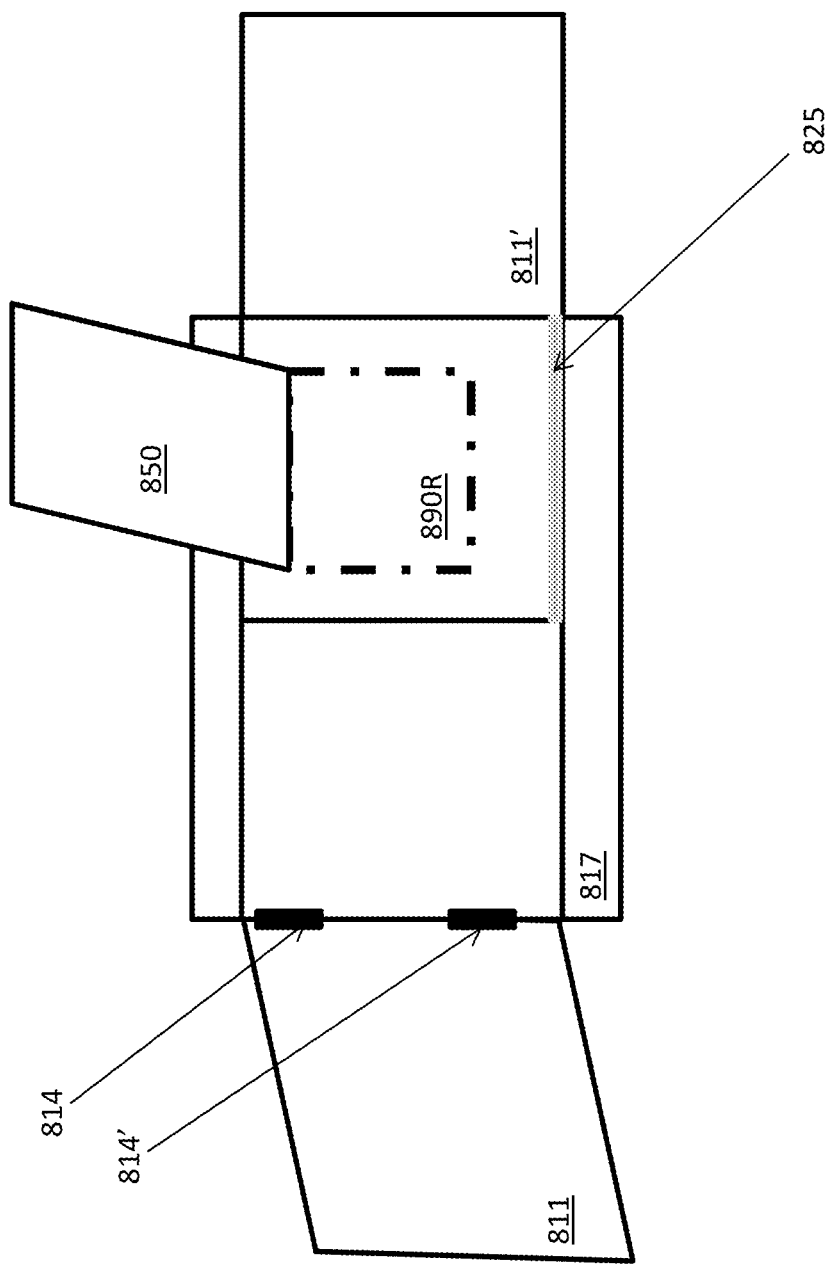
FIG. 8 is a block diagram of an embodiment of an ophthalmic testing system and measurement system.

The opaque portion(s) 711 can be an integral part of the head-wearable device 700 and/or be removably or replaceably attached to the head-wearable device 700. For example, as shown in FIG. 8, at least a portion of the head-wearable device can comprise one or more opaque portions 811, 811' that have been hingedly coupled device 700. In some embodiments, the one or more opaque portions 811, 811' can be coupled to the front face 817 of the head-wearable device.

The opaque portion 811 can be the head-wearable device using at least one hinge 814, 814' and configured such that the opaque portion can be lifted to allow passage of ambient light to at least one eye of the subject. Alternatively or additionally, the opaque portion 811' can comprise a slidable screen configured to be slidably positioned substantially in front of at least one eye of the subject to obstruct passage of light thereto. The head-wearable device can comprise any suitable mechanism needed to accommodate coupling of the opaque portion(s) 811, 811' to the device. For example, at least a portion of the head-wearable device can comprise a rail 825 configured to allow the slidable opaque portion 811' to slide onto the head-wearable device (front face of the head-wearable device).

In some embodiments, a flip seal 850 can be disposed to an area 890R of the front face 817 of the head-wearable device and configured such that upon placement of the flip seal 850 on the front face of head-wearable device, passage of ambient light to the subject's eye(s) is obstructed. Under this configuration, lifting of the flip seal 850 allows passage of the light through the area 890R of the face 817 to the subject's eye(s). In other words, the flip seal 850 and/or the opaque portions 811/811', once placed on the front face of the head-wearable device, are configured to be positioned in substantial register with the subject's eye when the head-wearable device is placed against the subject's face and to block ambient light from entering the subject's eye. Similarly, lifting/sliding the flip seal 850 and/or the opaque portions 811/811' about the hinge 814/814' and/or on the rail 825 can allow the ambient light to enter the subject's eyes.

As noted, in a closed configuration, the light-blocking portions 821, 821 can inhibit, or at least minimize, the passage of ambient light to the subject's eye. In an open configuration, the light-blocking portions can be lifted via rotation about the hinge(s) 814, 814' to expose the cavities/chambers 889L, 889R to allow the ambient light to reach the subject's eye(s). This configuration can allow the positioning of the head-wearable device and mask on the subject's eye, while the subject is still able to receive ambient light, thereby transitioning the light luminance from ambient to a much lower level needed for performing the ophthalmic test. Such a transition is herein referred to as "going dark transition," and can help the subject to adapt more readily to the dark condition required for performing the ophthalmic test.

FIGS. 9A-9E depict various illustrative examples of head-wearable implementations of an ophthalmic testing and measurement device 900/900' according to some embodiments disclosed herein. FIG. 9F illustrates an exploded view of the example shown in FIG. 9E. FIG. 9G illustrates a perspective view of a light seal according to some embodiments disclosed herein.

The head-wearable device 900/900' can generally be configured to perform any suitable ophthalmic diagnostic procedure on at least one eye of a subject 991. For example, the head-wearable device 900/900' can be used in performing an ophthalmic diagnostic test, such as measurement of dark adaptation, in at least one eye of a subject 991.

As shown in FIGS. 9A-9E, and 4C, the headset 902 can include a housing or chamber 902H, in which various components of the ophthalmic testing and measurement device can be disposed. The housing 902H can house the optical and electronic components (e.g., optical systems, etc.) that are required for performing the one or more ophthalmic tests and/or measurements that can be conducted using the head-wearable device 900/900'. The chamber 902H can include a front face 972, a top face 973, a bottom face (not shown), and a back face 974.

Figure 9A:
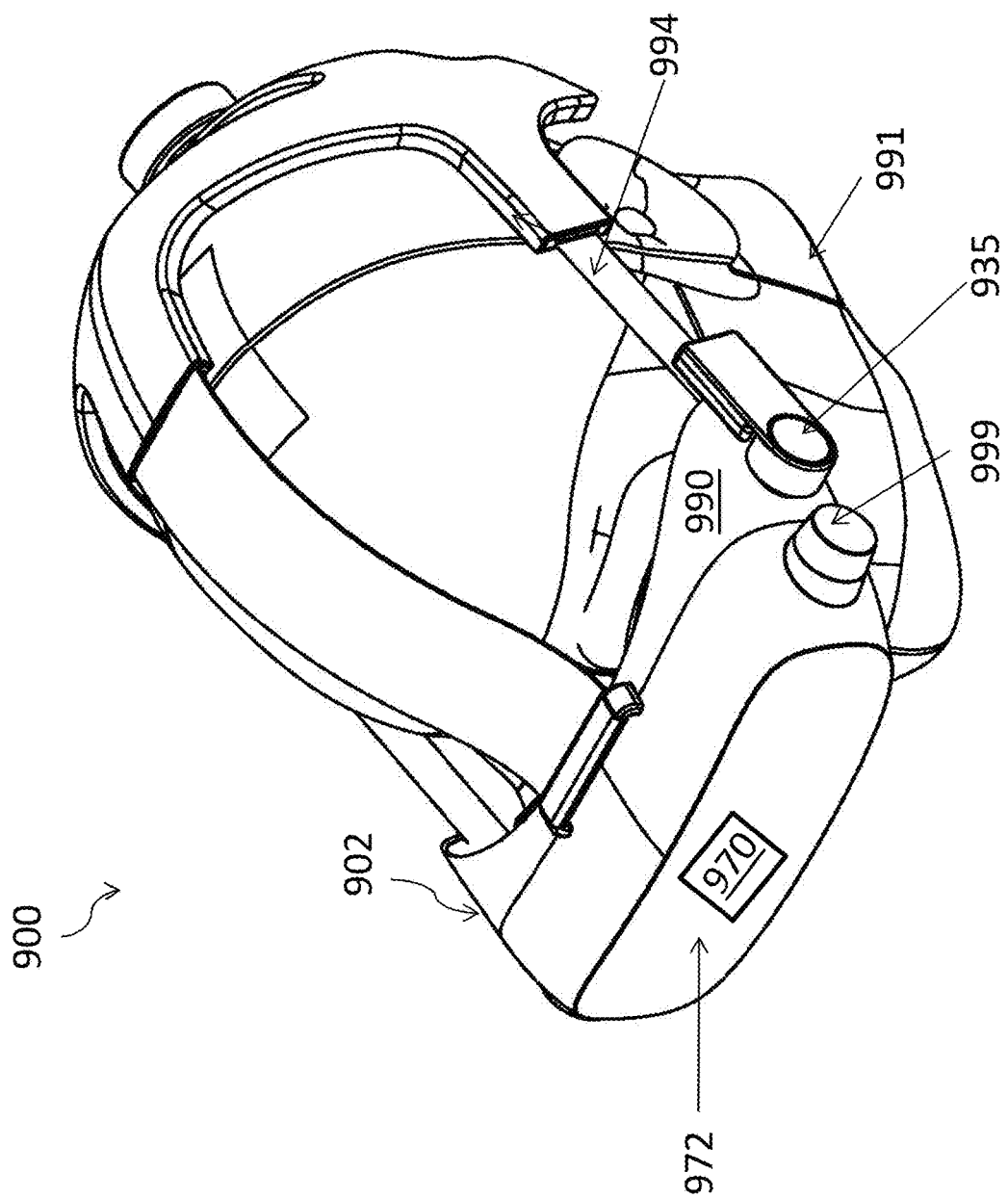
FIG. 9A is a schematic illustration of a head-wearable device according to some embodiments disclosed herein.
Figure 9B:
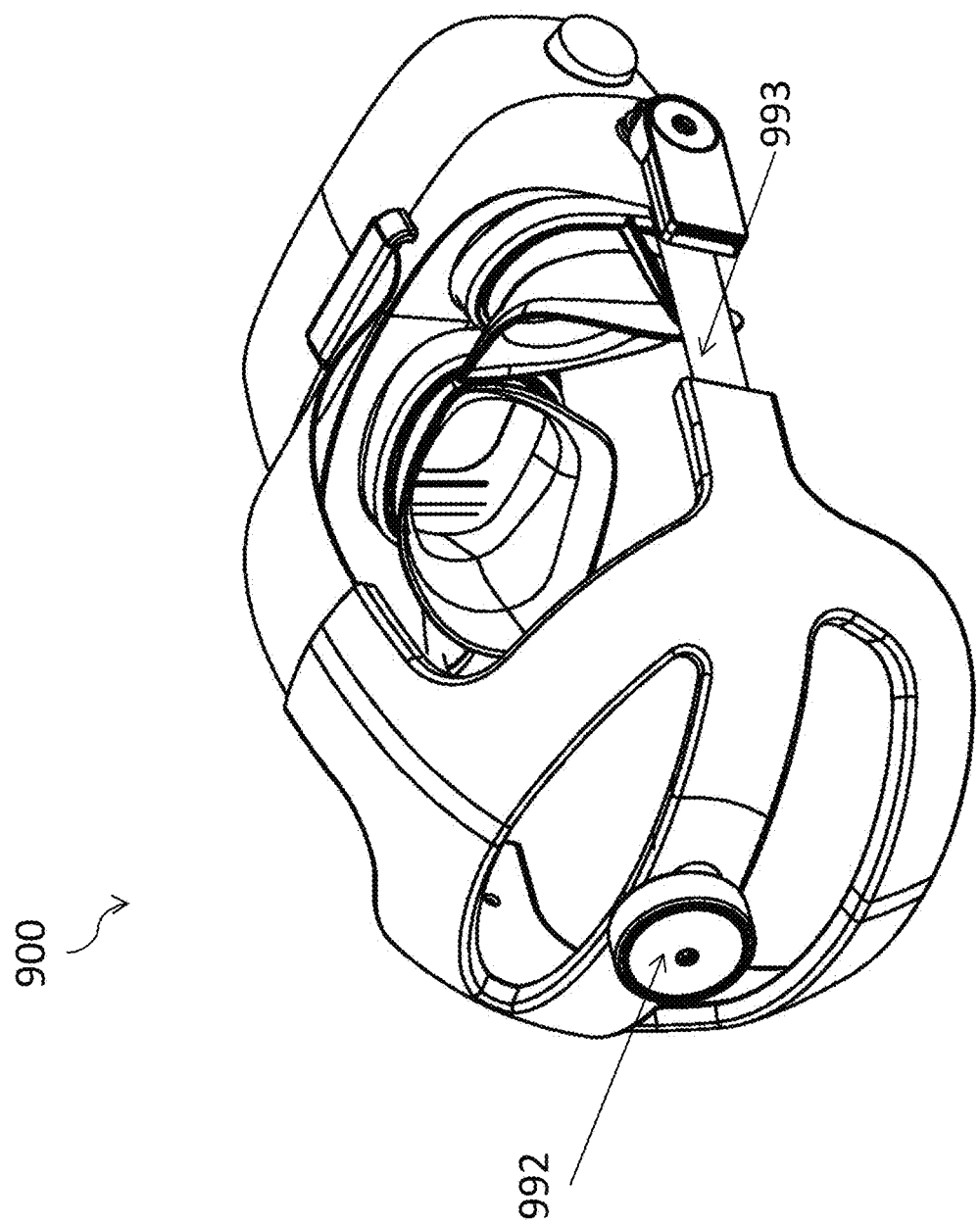
FIG. 9B is another view of a schematic illustration of a head-wearable device according to some embodiments disclosed herein.
Figure 9C:
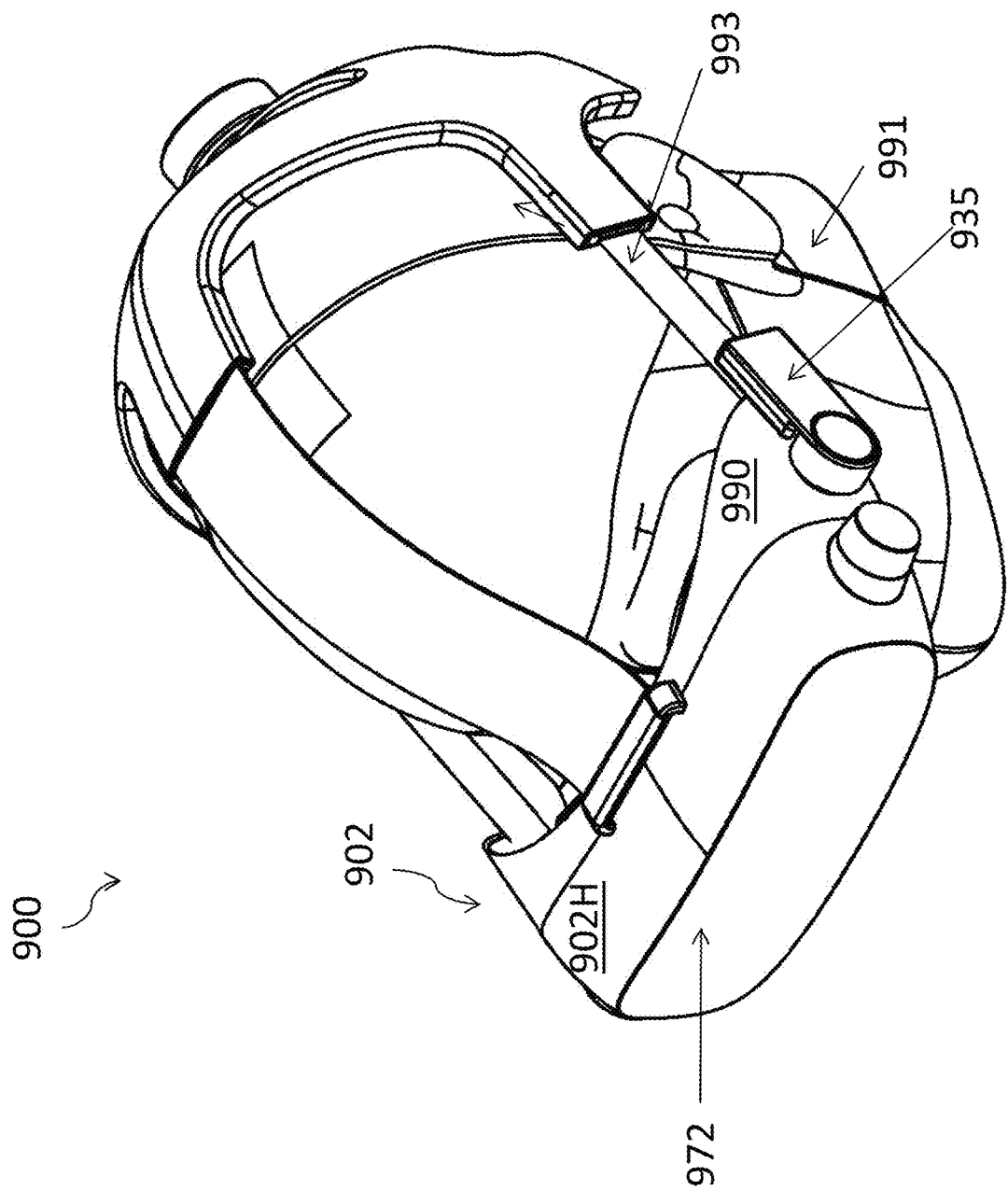
FIG. 9C is another is a schematic illustration of a head-wearable device according to some embodiments disclosed herein.
Figure 9D:
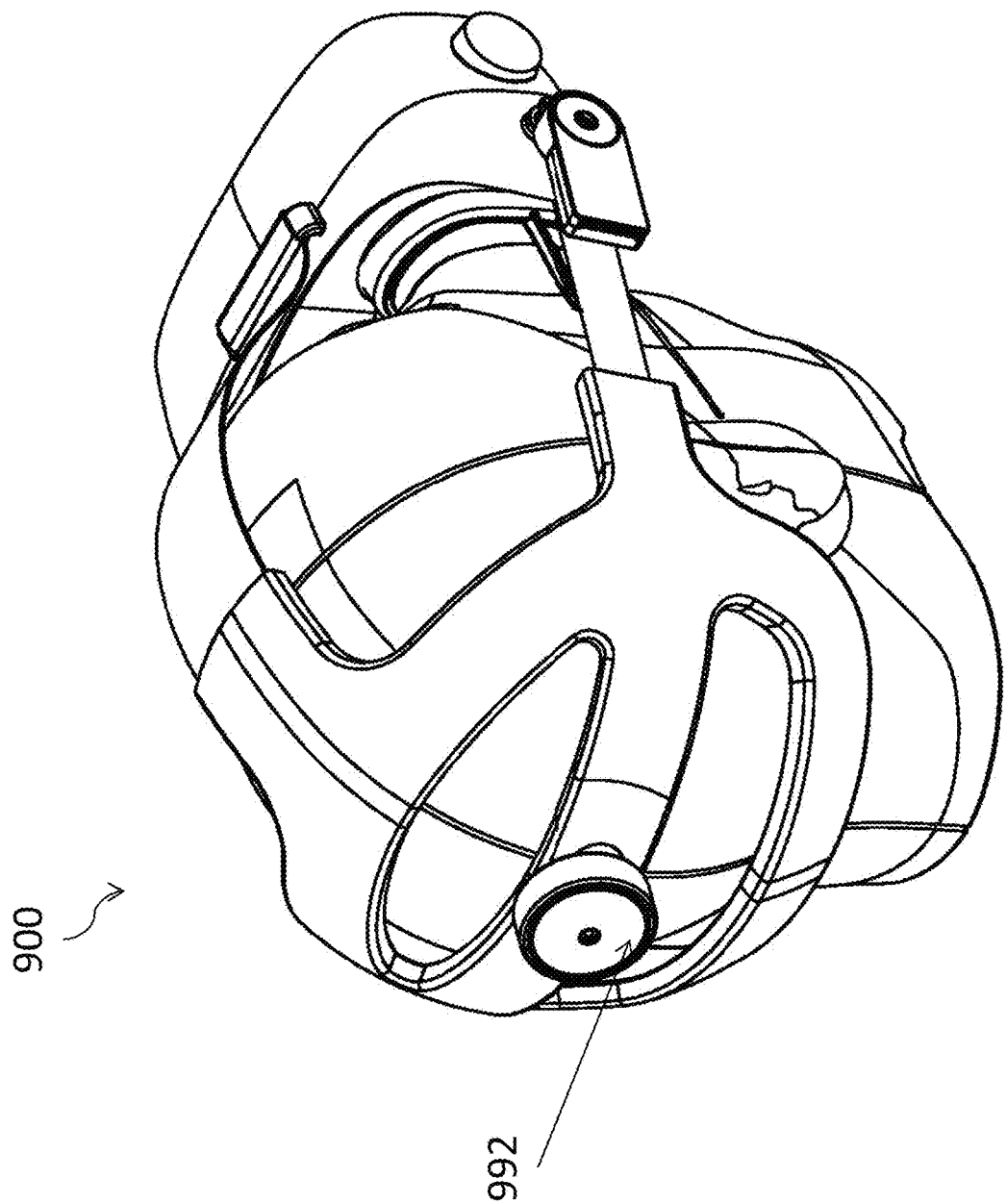
FIG. 9D is another view of a schematic illustration of a head-wearable device according to some embodiments disclosed herein.
Figure 9E:
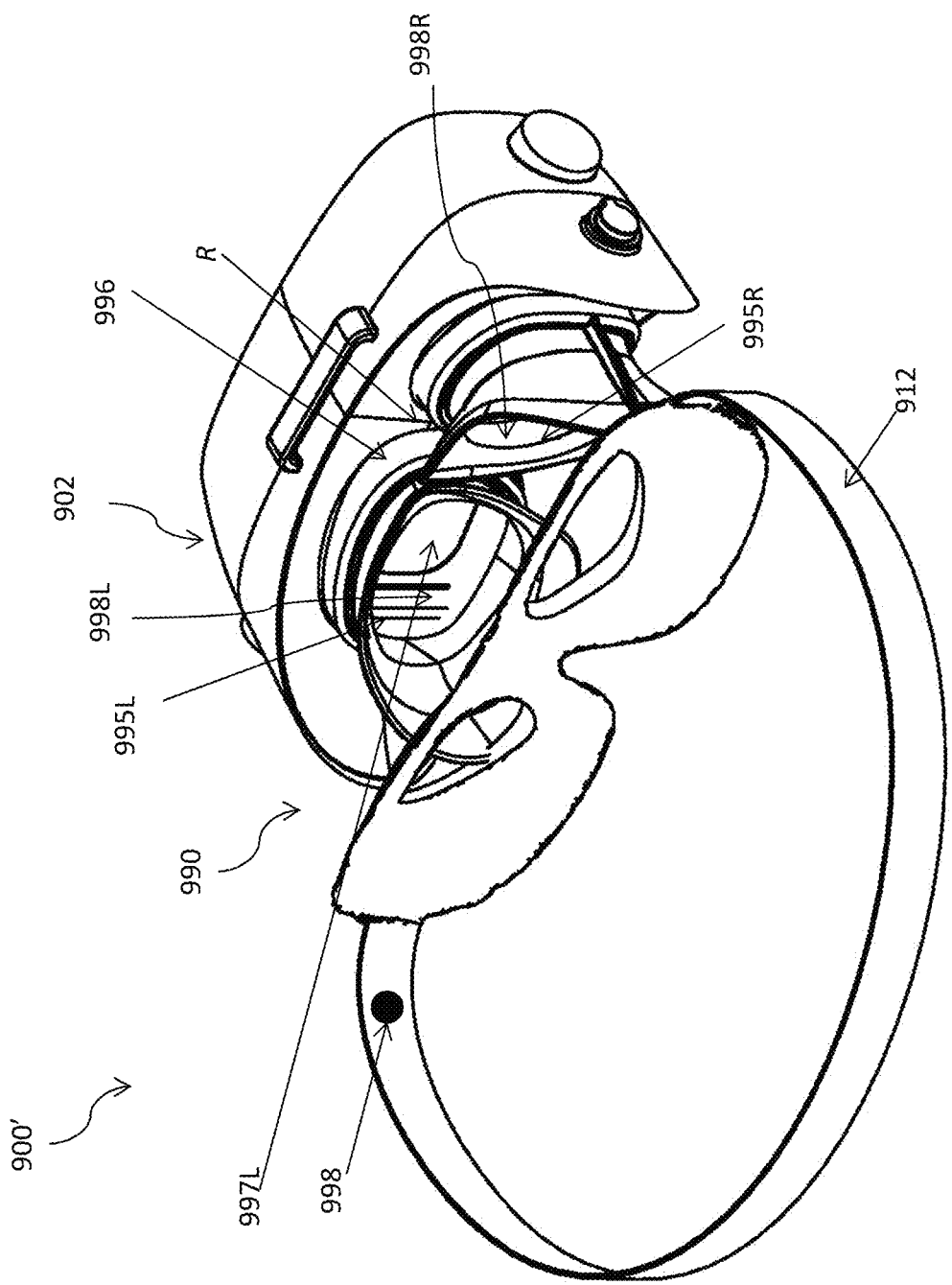
FIG. 9E is another schematic illustration of a headset according to some embodiments disclosed herein.
Figure 9F:
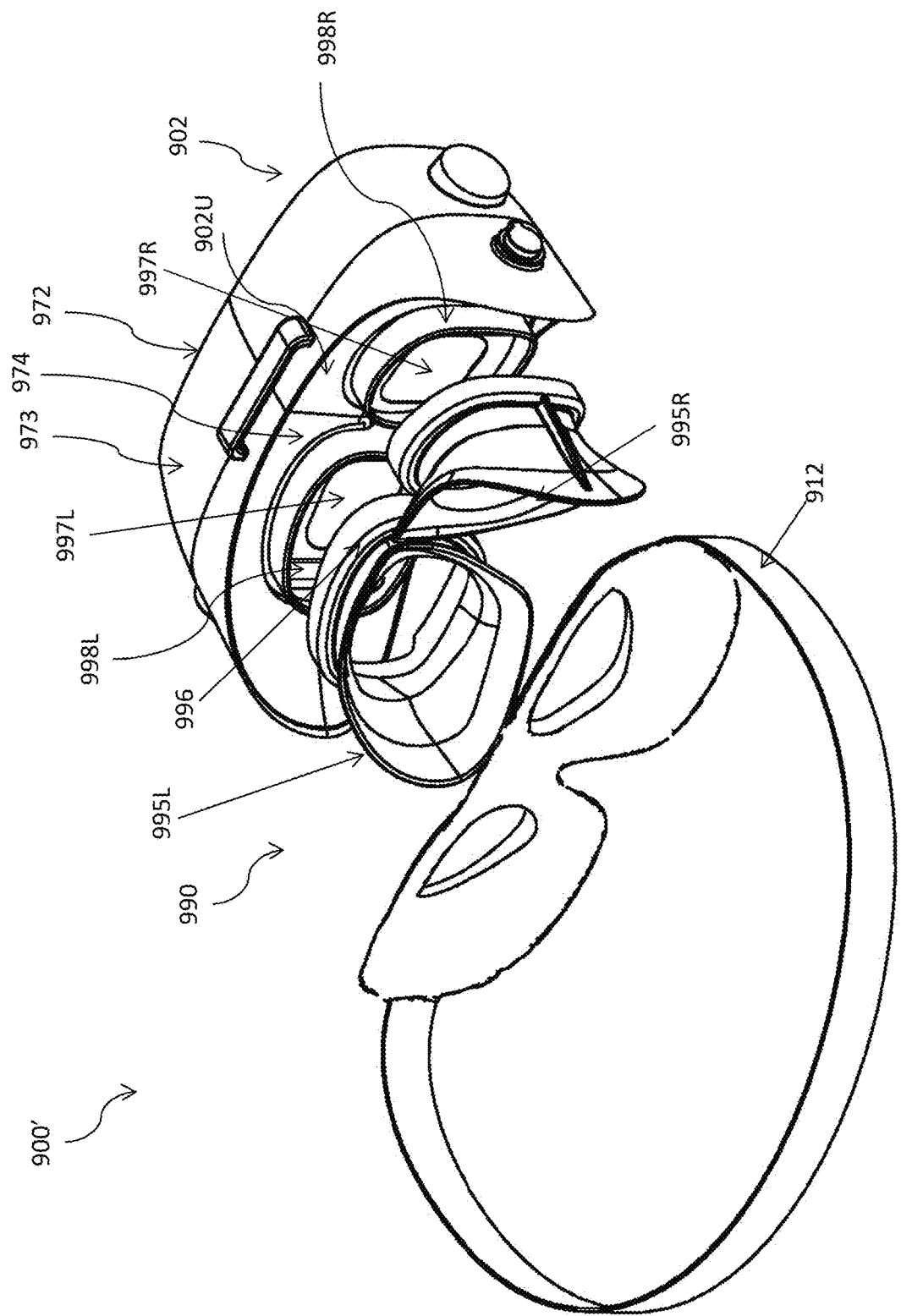
FIG. 9F is another schematic illustration of a headset according to some embodiments disclosed herein.
Figure 9G:
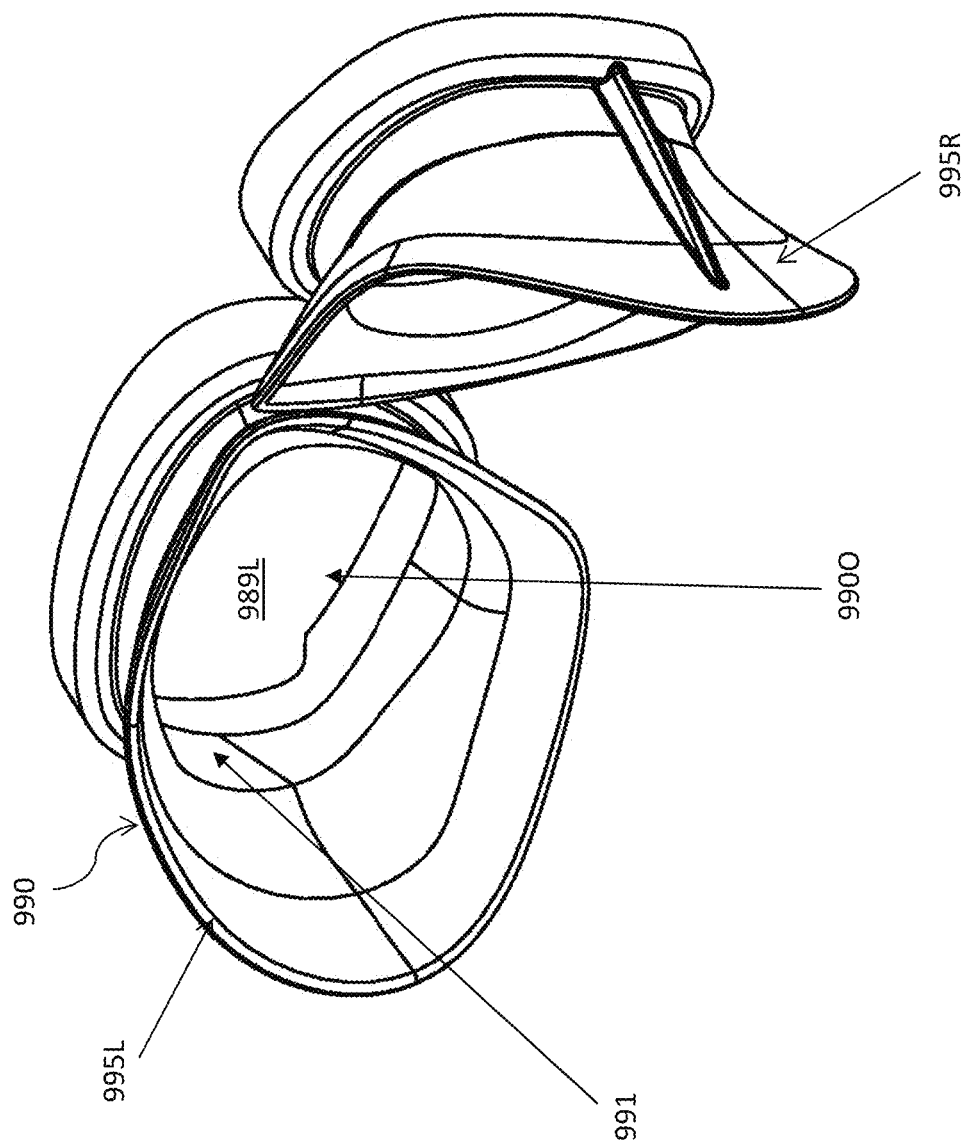
FIG. 9G is a schematic illustration of a light seal according to some embodiments disclosed herein.

As noted with reference to FIG. 9E, the chamber 902H can include one or more partitions that are configured to divide the chamber 902H into two or more compartments, each of which can be associated with one of the eyes of the subject. For example, the chamber 902H can include two compartments 998R, 998L, each of which can be associated with one of the eyes of the subject. The compartments 998R, 998L can comprise external cup-shaped features and be configured such that each compartment 998R, 998L is adjacent to and/or surrounds at least one eye of the subject (e.g., compartment 998R surrounds the right eye and compartment 998L surrounds the left eye).

The interior portions of each compartment 998R, 998L can house various components and can be configured to perform various functions required for conducting the one or more optical tests and measurements performed by the head-wearable device 900/900'. For example, compartments 998R, 998L can house the components required for conducting the same test and/or measurement. Specifically, the compartments 998R, 998L can be configured such that they house the components required for conducting a test or measurement (e.g., measurement of dark adaptation) on one eye or both eyes of the subject. For example, in embodiments that utilize removable cartridges (e.g., cartridges 500R, 500L in implementation shown in FIG. 5A) the compartments 998R, 998L can be configured to house the removable and replaceable cartridges.

Alternatively or additionally, the compartments 998R, 998L can be configured to house the components required for conducting different ophthalmic tests and/or measurements. For example, the compartments 998R, 998L can be configured such that one compartment houses the components required for conducting a first ophthalmic test and/or measurement on one eye of the subject while the other compartment houses the components required for conducting a second ophthalmic test and/or measurement on the other eye of the subject. As noted above, these components can be removable and replaceable and/or be an integral part of the ophthalmic system. Alternatively or additionally, at least one compartment 998R, 998L can be at least partially empty. Further, in some embodiments, at least one compartment 998R, 998L can be at least partially sealed to block ambient light from entering the compartment that houses the components required for conducting the ophthalmic test and/or measurement being provided by the head-wearable device 900/900'.

As noted above, the head-wearable implementations 900/900' of the testing and measurement systems described herein can include a head-wearable headset 902 that can be worn by the subject and/or mounted on the subject's head such that at least a portion of the device is adjacent to at least one eye of the subject. The headset 902 can be mounted on the subject's head using any available and suitable mechanism. For example, as noted above, a strap 994 can be coupled to the headset 902 and configured to allow the subject to wear the head-wearable device 900/900' such that the head-wearable headset 902 is positioned against at least a portion of the subject's head when worn by the subject 991. The strap 994 can be adjustable to ensure that it can be adjusted to fit around each individual subject's head and provide a comfortable fit for each individual subject.

Generally, the strap 994 can be connected to the headset 902 using any suitable or available mechanism. For example, the strap 994 can be rotatably coupled to the headset 902 using one or more adjustable mechanism 935. Alternatively or additionally, the strap 394 can be coupled to the headset 902 using one or more rotatable dials, hinges, and/or ratchets 935. The one or more rotatable dials, hinges, and/or ratchets 935 can be configured such that they allow the strap 994 to rotate to any desired or suitable orientation or dimension.

For example, the strap 994 can be coupled to the headset 902 using a resistive hinge 935 that is configured such that they can provide the strap 994 with from about 5° to about 225° degree of rotation relative to the headset 902. This rotatable feature of the strap 994 can allow the strap 994 to be comfortably fitted to a subject's head. Further, the adjustable mechanism 935 can incorporate a dampener that provides resistance to rotation. Specifically, the dampener can be configured to prevent unwanted rotation of the strap 994 such that the adjustable mechanism 935 requires physical manipulation of the strap 994 and headset 902 to reposition these elements relative to one another.

The strap 994 can comprise one or more layers of materials. For example, the strap 994 can include an internal layer 934 on the side of the strap that is configured to come in contact with the subject's head. Further, the internal layer 934 can be removably and replaceably coupled to the strap 394. For example, the internal layer 934 can comprise a disposable layer that is configured to be disposed and/or replaced after each use (or after a number of uses). In some embodiments, the disposable layer 934 can comprise an adhesive (e.g., Velcro®) that allows for attachment and/or removal of the disposable layer from the strap 994.

Alternatively or additionally, at least one of the strap 994 and the internal layer 934 can comprise a material that allows for surface cleaning of the internal layer 934 and/or the strap 994 before/after each use. For example, at least one of the internal layer 934 and the strap 994 can comprise woven or non-woven natural or polymeric fiber, a material (e.g., metal such as aluminum, stainless steel, copper, etc. or polymer such as Delrin, polycarbonate, polyurethane, etc.) that is capable of being cleaned with traditional medical grade cleaning agents (e.g., rubbing alcohol), etc.

The strap 994 can also include at least one adjustment dial 935 that can be used to adjust the length of the strap 994 and provide a suitable and comfortable fit for the subject's head. The adjustment dial 935 can be configured such that it can be used to adjust the head-wearable device 900/900' around the subject's head to any suitable orientation, length, and/or position. Further, the adjustment dial 935 can be configured such that it can be manually and/or automatically (e.g., under instructions received from a processor 310 (shown FIG. 3)) adjusted to provide a suitable and/or comfortable fit around the subject's head.

The head-wearable device 900/900' can also include a light seal 990 configured to isolate at least one eye of the subject from ambient light. As noted above, the light seal 990 can be coupled to the headset 902 and configured to isolate at least one eye of the subject (e.g., in some embodiments both eyes of the subject) from ambient light.

The light seal 990 can be an integral part of the device 900/900' and/or be removably or replaceably coupled to the headset 90 of the head-wearable device 900. Further, the light seal 990 can generally comprise any suitable material known in the art. For example, the light seal 990 can comprise a polymeric material, such as at least one of silicone, polyurethane, neoprene, polyolefin, nitrile rubber, ethylene vinyl acetate (EVA), polyvinyl alcohol (PVA), and polylactic acid (PLA). Additionally or alternatively, the light seal 990 can comprise a plurality of fibers, such as cellulose fibers and/or a foamed material, such as any of closed-cell or open-cell polymeric foam, alginate foam and starch-based foam.

The light seal 990 can have various features that are configured to facilitate formation of a light seal around at least one of the subject's eyes. For example, the light seal 990 can include one or more flanges 995R, 995L that are configured to conform to the areas surrounding the subject's eyes and/or at least a portion of the subject's head in order to form a seal that inhibits, and preferably, prevents the ambient light from entering the subject's eye(s). The flange 995L, 995R can comprise any suitable available material and be formed to assume any suitable shape and/or size.

As noted, the light seal 990 can be configured to isolate each eye independently from ambient light or isolate both eyes simultaneously from the ambient light. For example, the light seal 990 can be configured to ensure independent isolation of each of the subject's eyes from the ambient light.

In some embodiments, the light seal 990 can include two cup-like portions 998R, 998L, separated from one another by a common segment R in the form of a ridge (FIG. 9E). Each cup-like portion 998R, 998L can comprise a viewing window 997R, 997L that can be configured to allow passage of the light to at least one eye of the subject. Each cup-like portion 998R, 998L can be configured such that it snugly surrounds a corresponding eye of the subject to isolate that eye from ambient light. For example, one or more flanges 995R, 995L can surround the areas adjacent to the eyes of the subject on the subject's head, at least a portion of the subject's nose, and/or any area immediately surrounding the subject's head to isolate each eye from the ambient light independently of the other eye. The light seal, including the disposable liner, can be formed using a variety of different materials (e.g., polymeric materials) and can be disposable or reusable.

In some embodiments, the light seal can comprise a polymeric material. The polymeric material can comprise any of silicone, polyurethane, neoprene, polyolefin, nitrile rubber, ethylene vinyl acetate (EVA), polyvinyl alcohol (PVA), polylactic acid (PLA). Additionally or alternatively, the light seal can comprise a plurality of fibers. For example, the fibers can comprise cellulose fibers. Additionally or alternatively, the light seal can comprise a foamed material. The foamed material can comprise any of alginate foam and starch-based foam.

As noted, the light seal 990 can comprise one or more portions, each of which can be reusable and/or disposable. FIG. 9E depicts an illustrative example of a head-wearable ophthalmic testing and measurement device 900' having a light seal 990 with at least one disposable portion 912. The disposable portion 912 can be a hygienic liner 912 disposed on the surface of the conformable body 996 of the light seal 990 and configured to come in contact with the subject's face/skin when the head-wearable device 900/900' is worn by the subject and/or when the head-wearable device 900' is placed against the subject's face. The hygienic linger 912 can be configured such that it comes in contact with the subject's skin and can be used and/replaced after it comes in contact with a subject's skin. The hygienic liner 912 can be a single-use and disposable item. In some embodiments, the hygienic liner can comprise a double-sided tape (e.g., for facilitating attachment/removal of the liner 912 to/from the strap 993).

In some embodiments, a tracking system 998 (e.g., an RFID tag or a barcode, hereinafter referenced generally as "RFID tag") can be incorporated in the light seal 990. The RFID tag 998 can be coupled to the light seal 990 and/or the liner 912 in any suitable known manner. As described with reference to FIG. 1G, the RFID tag 998 can be incorporated in the disposable layer 912 to ensure that the disposable layer 492 is an authentic disposable (provided by the original manufacturer of the device) and also to enforce single usage of the disposable layer.

In some embodiments, the receptacles or chambers can provide a cavity into which a light mask according to the present teachings can be partially fitted. For example, as shown in FIG. 9F-9G, a portion 991 of the light mask 990 can be fitted into the receptacles or chambers 989L to facilitate positioning of the light mask over the subject's eyes. Specifically, the mask 990 can be coupled to the cavity 989L such that the openings in the mask 990O is in substantial register with the window provided in the cavity 997R/997L. Under this configuration, when the light-blocking portions 811, 811' are closed (e.g., FIG. 8), the subject can view the light emanating from the light source(s) of the ophthalmic testing system that is/are positioned in the head-wearable device 900'. The light sources can be disposed in an upper portion 902U of the head-wearable device 900'. Further, the upper portion 902U of the head-wearable device 900' can include other components, such as electronic components, required for performing an ophthalmic test.

Figure 10A:
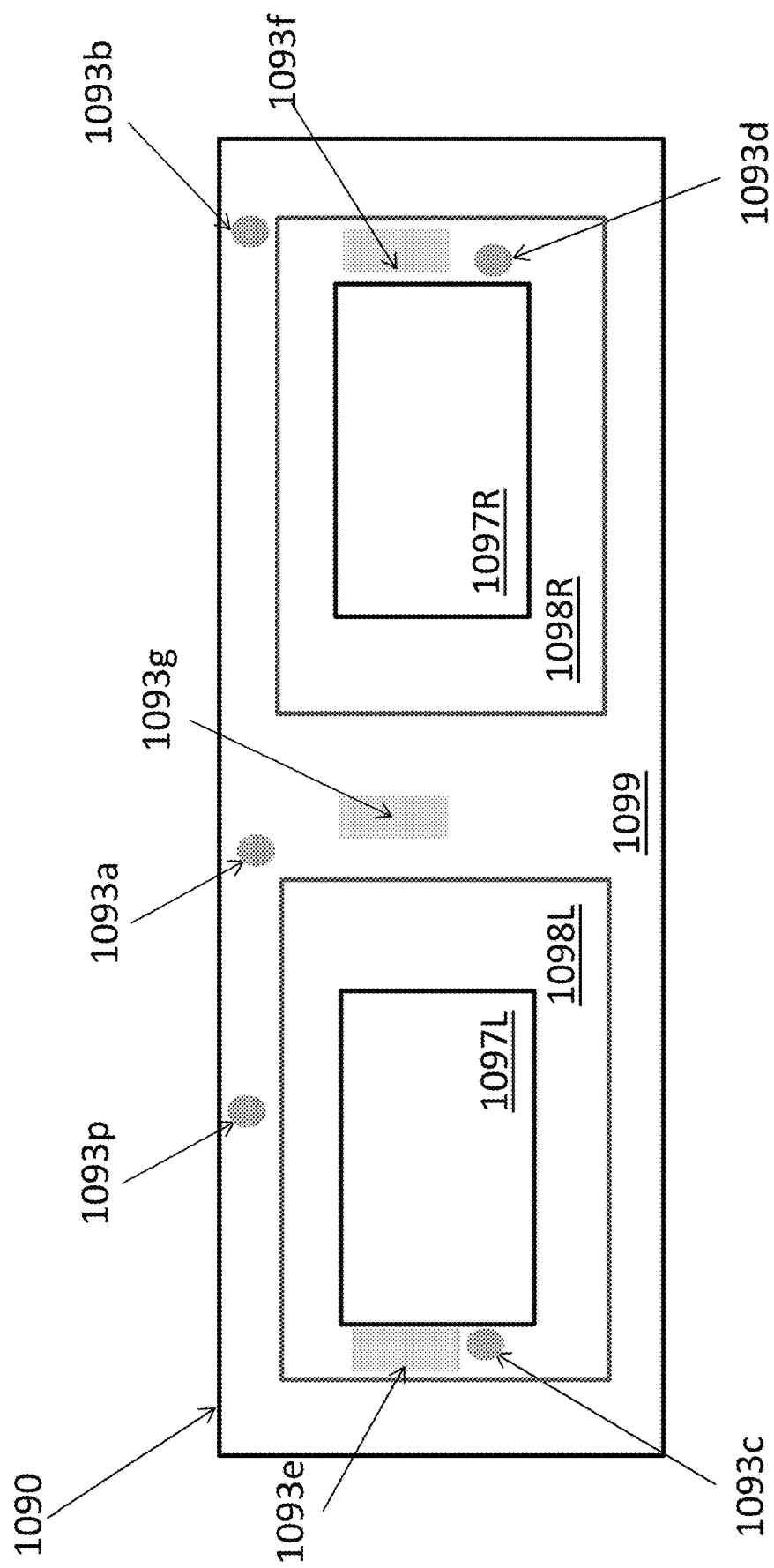
FIG. 10A is a high-level block diagram of a light seal according to some embodiments disclosed herein.

FIG. 10A depicts a block diagram of a light seal 1090 according to some embodiments disclosed herein. As shown, the light seal 1090 can comprise an internal cavity 1099 having one or more cups 1098R, 1098L, each configured to seal one eye of the subject from ambient light. In the example shown in FIG. 10A, the left cup 1098L can be configured to seal the left eye of the subject from ambient light and the right cup 1098R can be configured to seal the right eye of the subject from ambient light. Although shown as connected units, the light seals 1098R, 1098L need not to be connected and can be independent elements (for example, as shown in FIG. 1F). Further, a light seal can be configured such that it can seal either eye (right or left) of the test subject and/or is capable of being coupled to either eye interface (right or left) of a head-wearable implementation.

The light seal 1090 can further include one or more viewing windows that are configured to allow passage of light to at least one eye of the subject. In the example shown in FIG. 10A, light seal includes a viewing window 1097L, 1097R in each cup 1098L, 1098R configured to allow passage of light to the respective eye of the subject.

The light seal 1090 can further comprise one or more light sensors 1093a, 1093b, 1093c, 1093d configured to detect an intrusion or leakage of extraneous or ambient light to the subject's eye(s). The light sensors can be positioned in any suitable manner on the light seal, for example adjacent to the viewing windows 1093c (adjacent to viewing window 1097L), 1093d (adjacent to viewing window 1097R), and be configured to detect possible leakage or intrusion of light into the cavity 1099 of the light seal 1090.

Alternatively or additionally, the light seal 1090 can include one or more light sensors 1093a, 1093b positioned on any suitable location within the cavity 1099 of the light seal 1090. For example, the light seal 1090 can include one or more sensors 1093a, 1093b on the boundaries of the seal 1090 (e.g., where the seal 1090 comes in contact with the subject's face or skin). The light sensors 1093a, 1093b, 1093c, 1093d can comprise any suitable light sensors. For example, the light sensors 1093a, 1093b, 1093c, 1093d can comprise one or more photodiodes (e.g., avalanche photodiodes) configured to sense any intrusion of extraneous light. In some embodiments, the one or more photodiodes can be located in the chamber 1099, inclusive of the any internal volumes of the assembly including on or near the optics, on interior of the eyecup, on or near disposable portions of the light seal, on the inside of the headset, and/or within the optics channel chamber.

The light seal 1090 can further comprise at least one of a pressure sensor and/or a capacitive sensor 1093p. The one or more pressure sensors can be included at any suitable location on the light seal 1090. Such pressure sensors can include, but are not limited to, one or more strain gauges disposed at key points along the elastomeric eyecups 1098L, 1098R and/or on the light seal 1090 to ensure an adequate sealing force is applied.

In some embodiments, the elastomeric eyecup 1098L, 1098R material can be impregnated with a conductive filler (e.g., carbon black) capable of assessing compressive force via change in electrical resistance or electrical capacitance in the eyecup. In such embodiments, sensors 1093g capable of measuring such changes (e.g., capacitive sensors) can be used to ensure an adequate sealing force is applied at all points around the perimeter of the eyecups 1098L, 1098R.

Figure 10B:
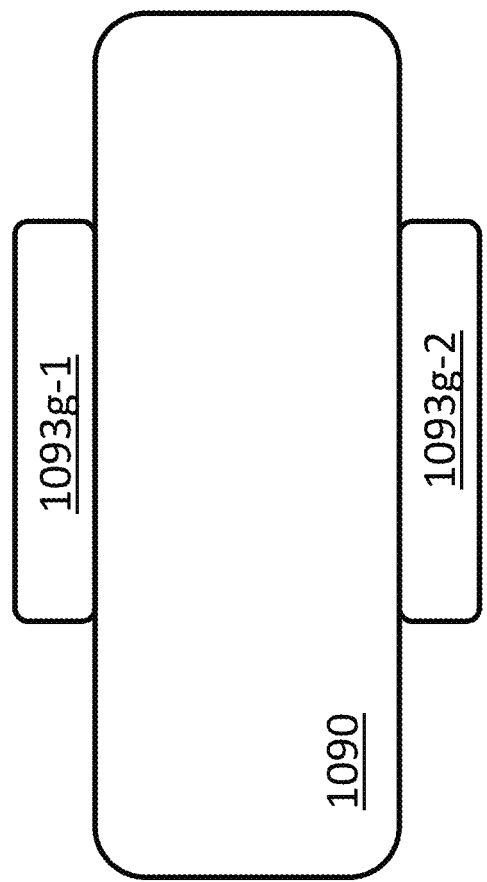
FIG. 10B is another high-level block diagram of a light seal according to some embodiments disclosed herein.

For example, as shown in FIG. 10B, the capacitive sensor 1093g can comprise at least two plates 1093g-1, 1093g-2, disposed on the light seal 1090. By way of example, the capacitive sensor 1093g can comprise two plates 1093g-1, 1093g-2, disposed on opposite sides of the light seal 1090 (e.g., inner side of the light seal and outer side of the light seal). The pressure exerted on the light seal 1090 during use (or reduction of pressure to the light seal) can cause the light seal to deform, thereby reducing (or increasing) plate separation between the two plates 1093g-1, 1093g-2. The reduction of plate separation (or an increase in plate separation) can, in turn, result in an increase (or decrease) in the capacitance of the capacitive sensor, thereby activating the sensor 1093g. The optical system can be configured such that if the capacitance detected by the sensor 1093g falls above or below a predetermined range, it triggers an alarm (e.g., using the alert system 630) indicating a possible leakage of light through the light seal 1090.

Alternatively or additionally, a disposable light seal 1090 incorporating a polymeric material impregnated with a conductive filler (e.g., carbon black) capable of assessing compressive force via a change in electrical resistance can be used to ensure an adequate sealing force is applied at all points around the perimeter of the eyecups 1098L, 1098R and/or disposable light seal 1090. Any other sensors, for example sensors (e.g., mechanical switch, magnet and Hall effect sensor, LED light switch, ultrasound sensor, etc.) capable of sensing a distance and/or proximity of the headset to at least a portion of the subject's eye can be employed in accordance with embodiments disclosed herein.

As noted above, a processor (e.g., processor 310 of an ophthalmic testing system according to embodiments disclosed herein) can be coupled to the sensors and configured to receive and process the information obtained by the sensor(s) included in the light seal 1090. In response, the processor 310 can trigger an alarm signal and/or provide a notification (e.g., via audio or visual notification) alerting a practitioner and/or the test subject of possible leakage of light through the light seal 1090.

Figure 11:
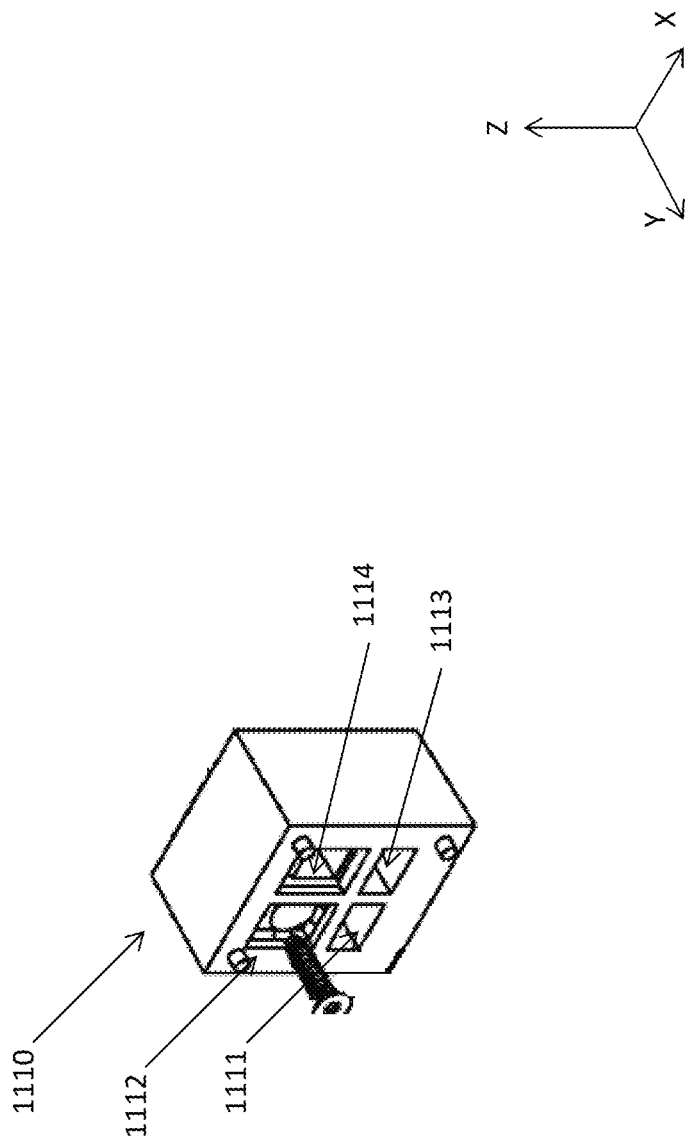
FIG. 11 depicts an illustrative example of an optical chamber according to some embodiments disclosed herein.

FIG. 11 depicts an illustrative example of an optical chamber 1110 in which the optical components (sources and optics) of the head-wearable device can be stored. The optical chamber 1110 can comprise one or more compartments. For example, the chamber 1110 can be divided into four compartments 1111, 1112, 1113, 1114. Further, each compartment of the chamber 1110 can be arranged to include one or more light sources and or optical elements. The one or more light sources can be configured to generate and/or deliver light at one or more luminance levels. For example, at least one light source can be configured to deliver a light at a first luminance level capable of bleaching photopigments and/or desensitizing a portion of the rhodopsin molecules in a test eye of a subject (the eye of the subject that is undergoing ophthalmic testing and/or measurement). A light source having such capabilities is generally referenced herein as a bleaching light source and light rays illuminated at such illuminance levels are generally referenced herein as a bleaching light. At least another light source can be configured to deliver a light at a second luminance level capable of isolating the response of the rod-shaped cells and stimulating the rod-shaped cells with no or little stimulation of the cone-shaped cells. A light source having such capabilities is generally referenced herein as a stimulus light source and light rays illuminated at such illuminance levels are generally referenced herein as a stimulus light. At least one other light source can be configured to deliver a light at an illuminance level configured for use for focusing the test eye of the subject. A light source having such capabilities is generally referenced herein as a fixation light source and light rays illuminated at such illuminance levels are generally referenced herein as a fixation light.

The one or more light sources can be used to provide a bleaching protocol to the individual undergoing visual testing. The bleaching protocol can be varied as needed according to any suitable and available technique. For example, the bleaching protocol can be configured to expose the test eye of the subject to a bleaching light. As noted above, the bleaching light is configured to desensitize at least a portion of the rhodopsin molecules in the test eye on exposure to the bleaching light. Visual recovery (e.g., dark adaptation) is then measured via the stimulus light. Accordingly, the bleaching light is configured to serve as a standardized baseline from which visual recovery can be measured.

Generally, any bleaching protocol that can provide a standardized baseline can be used with the embodiments described herein. The bleaching light is generally configured to be brighter than the stimulus light and the absolute intensity values of the bleaching light and stimulus light can be varied as desired. Generally, bleaching lights having higher intensity levels (larger absolute value of the intensity level) require shorter exposure time periods to achieve the baseline required for measuring dark adaptation. In some embodiments, the intensity of the bleaching light can be, for example in a range of about 1.5 log Scotopic Trolands/sec to about 8 log Scotopic Trolands/sec and/or an intensity in a range of about 3 log Scotopic Trolands/sec to about 5 log Scotopic Trolands/sec.

As noted above, the bleaching protocol can desensitize a desired amount of rhodopsin molecules and provide a standardized baseline to measure visual recovery to the stimulus light. The intensity of the bleaching light or the time of exposure to the bleaching light can be modulated to produce the desired amount of desensitization. For example, an equivalent of about 50% to 100% of the rhodopsin molecules can be desensitized. The intensity of the bleaching light can also be adjusted to desensitize the appropriate amount of rhodopsin molecules. For example, a bleaching light intensity of 7.65 log Scotopic Trolands/sec can be used to bleach approximately 98% of the rhodopsin molecules, while a bleaching light intensity of 5.36 log Scotopic Trolands/sec can be used to bleach approximately 50% of the rhodopsin molecules, while a bleaching light intensity of 1.56 log Scotopic Trolands/sec can be used to bleach approximately 20% of the rhodopsin molecules. If desired, alternate bleaching light intensities which desensitize less than 50% or more than 50% of the rhodopsin molecules can also be used.

Generally, the bleaching light can comprise one or more wavelengths in a range of about 490 nm to about 510 nm. In some embodiments, the bleaching light can comprise no wavelength component outside the range of about 490 nm to about 510 nm. Alternatively or additionally, the bleaching light can comprise one or more wavelengths in a range of about 600 nm to about 700 nm. In some embodiments, the bleaching light can comprise no wavelength component outside the range of about 490 nm to about 510 nm. Further, the light source emitting the bleaching light can be configured to generate bleaching light pulses having a duration in a range of about 0.5 milliseconds to about 200 milliseconds. Furthermore, the bleaching light can comprise an intensity in a range of about 1.5 log Scotopic Trolands/sec to about 8 log Scotopic Trolands/sec.

After the bleaching protocol is executed, visual recovery can be monitored and measured via the stimulus light. This recovery of light sensitivity can be mediated primarily by the retina and can measure predominately rod-mediated sensitivity. The subject can be asked to provide a series of responses to the stimulus light, which can be varied in intensity according to one or more index factors. These index factors can be used to determine a dark adaptation status of the subject. Additionally or alternatively, the response of the subject can be used to determine a threshold measurement, wherein the threshold can be defined using the stimulus light intensity at which the subject reports the stimulus light as being visible. The threshold can generally be defined using any suitable technique. One example of threshold measurement is described in detail in U.S. application Ser. No. 13/028,893, the entire teachings of which are incorporated herein by reference.

Referring back to the example shown in FIG. 11, the device can comprise one or more fixation light source $S_1^F$, $S_2^F$, a bleaching light source $S_1^B$, and a stimulus light source $S_1^S$. The bleaching light source $S_1^B$ can be adjusted to provide a bleaching light at any suitable intensity (e.g., high or low intensity light). Further, the bleaching light can comprise an intensity in a range of about 1.5 log Scotopic Trolands/sec to about 8 log Scotopic Trolands/sec.

The fixation light source, the bleaching light source $S_1^B$, and the stimulus light source can generally comprise any suitable light source available in the art. For example, these light sources can be laser and/or an LED light sources. In one embodiment, the bleaching light source $S_1^B$ can be an achromatic camera flash or a bank of LED lights. Further, although described as separate light sources, one skilled in the art should appreciate that a single light source can be used, in some embodiments, to generate one or more of the illumination levels employed herein. Further, although the bleaching light source is described as an internal component of the head-wearable device, in some embodiments, the bleaching light source can be omitted from the head-wearable device, and the bleaching can be carried out independently of the head-wearable device.

As noted above, the bleaching light source $S_1^B$ can generally comprise any light source capable of emitting a light beam having a desired spectrum for bleaching the photopigments in the test eye. For example, the bleaching light source $S_1^B$ can comprise one or more LEDs (bank of LEDs) that are configured to emit a light beam 403 (e.g., white light beam).

Similarly, the stimulus light source $S_1^S$ can comprise a spectrum effective in stimulating the rod-shaped photoreceptors of a subject's eye. For example, the stimulus light can comprise one or more wavelengths in a range of about 400 nm to about 750 nm. Alternatively or additionally, the stimulus light source $S_1^S$ can be configured to generate light stimuli having a duration in a range of about 100 milliseconds to about 400 milliseconds. In some embodiments, the stimulus light can comprise an intensity in a range of about $5 \times 10^{-4}$ cd/m² to about 5 cd/m2. In one embodiment, the initial target stimulus intensity can be 4.85 cd/m2, although other initial intensities can be used. In some embodiments, the stimulus light can comprise an intensity in a range of about $4.0 \times 10^{-5}$ cd/m² to about 5 cd/m².

As noted previously, with reference to FIG. 6, a pair of mirrors can be positioned at an angle relative to one another and configured to direct the light emitted by the light sources to the subject's eye. The optics can also include one or more lenses that direct the light to the subject's eyes. For example, as noted above, a convergent lens can be mounted onto the movable platform 603, 603', and positioned in the path of the light in front of the subject's eye for collimating the light reflected by the mirror(s) before its entry into the subject's eye through the pupil. The bleaching light source $S_1^B$ can generate visible light (e.g., light having a wavelength in a range of 450 nm to 560 nm) at a desired light intensity (e.g., 3 log scotopic Tds to 7 log scotopic Tds). The stimulus light source $S_1^S$ can generate visible light (e.g., 45 nm to 560 nm) and at a desired light intensity (e.g., $5 \times 10^{-4}$ scotopic cd/m² to 5 scotopic cd/m²).

The fixation light sources $S_1^F$, $S_2^F$ are configured to direct the subject's gaze toward the respective bleaching light $S_1^B$ and the stimulus light $S_1^S$. The fixation light sources $S_1^F$, $S_2^F$ can emit visible light at a wavelength and at a desired light intensity though other wavelengths and light intensities can also be employed.

Figure 12:
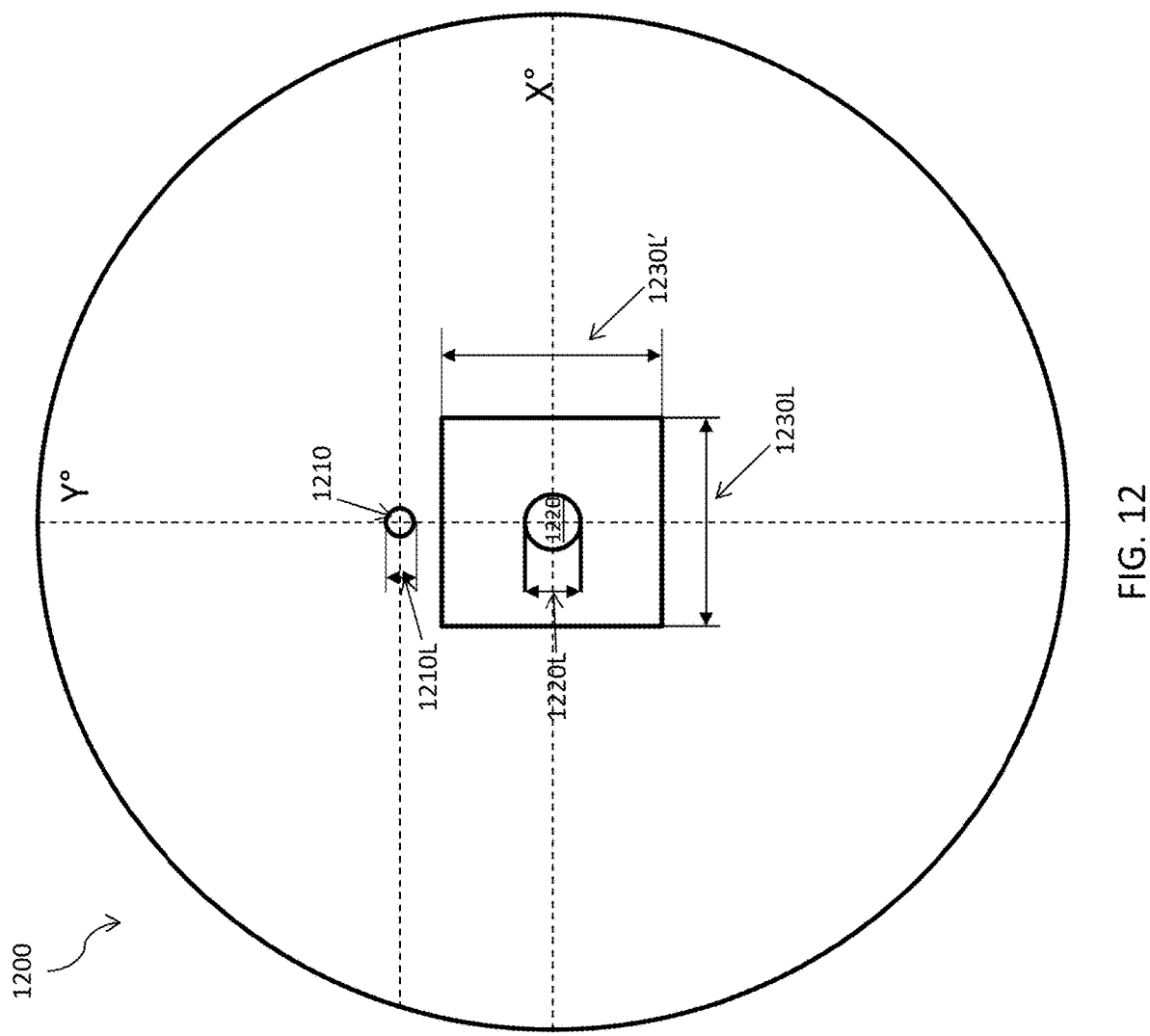
FIG. 12 is a schematic illustration of an image plane that can be presented to a test subject according to some embodiments disclosed herein.
Figure 13:
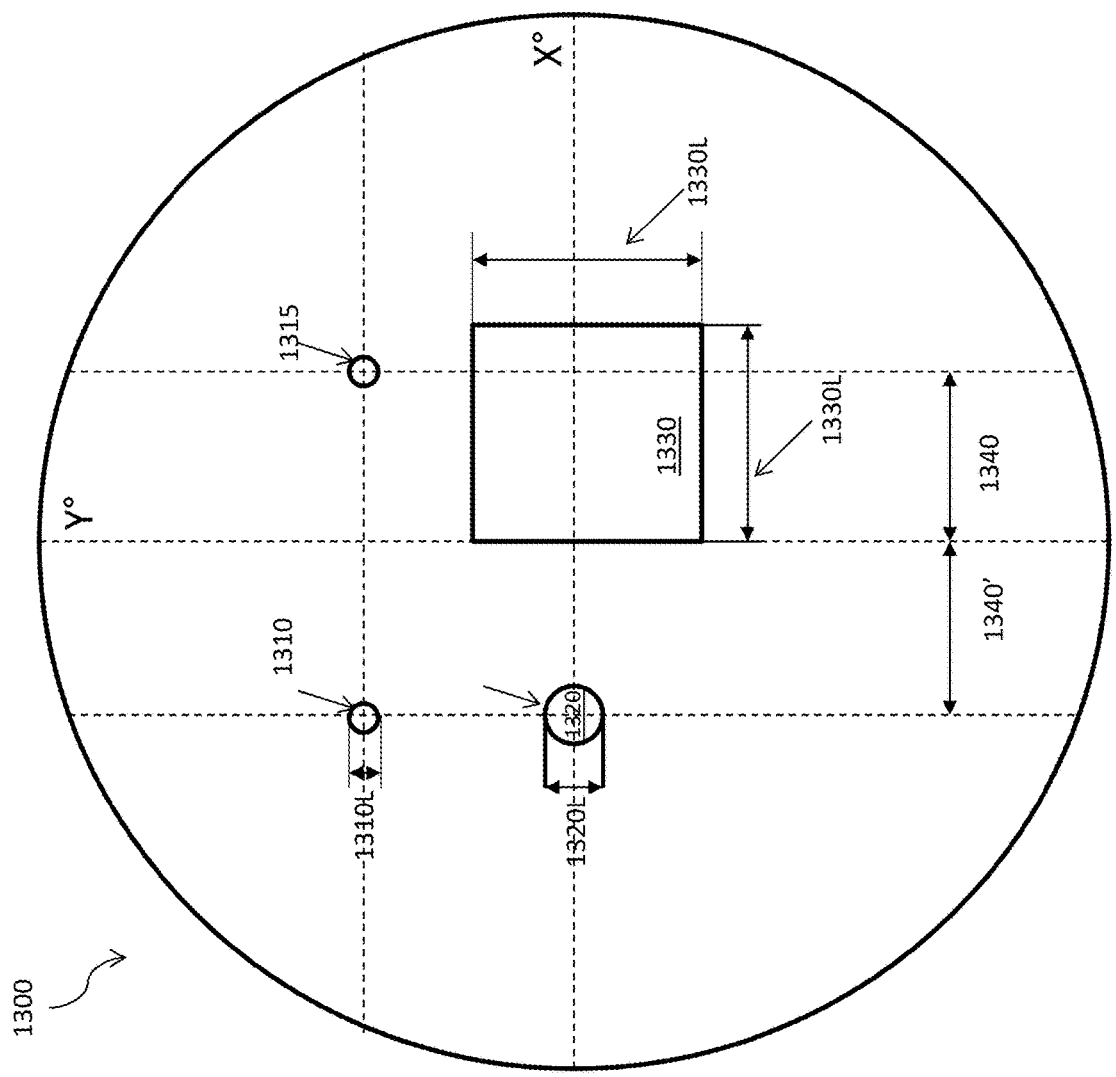
FIG. 13 is another schematic illustration of an image plane that can be presented to a test subject according to some embodiments disclosed herein.

During the testing and measurement, an image plane can be presented to a test subject. FIGS. 12-13 illustrate examples of two different image planes 1200, 1200' that can be presented to a test subject. The image planes can be used with tabletop and/or a head-wearable implementations of the ophthalmic testing systems described herein.

As noted above, the image plane 1200 can comprise a fixation dot 1210 that is presented to the subject using an implementation of the ophthalmic testing system according to embodiments disclosed herein. The subject is asked to fixate her gaze during the ophthalmic test (with some rest periods) on the fixation dot 1210. As the subject continues to fixate her gaze on the fixation dot 1210, a bleach area 1230 is presented in the image plane 1200. The subject is directed to fixate his/her gaze on the fixation light and is initially presented with a bleach pulse of light using the bleach aperture. After the bleach process is complete, the image plane is altered to present a smaller stimulus light area 1220 to the user for the rest of the test.

As shown, the bleach area 1230 can comprise an area (having a length 123L) that is configured to be larger than the stimulus area 1220 (having a length 1220L) in order to ensure that the stimulus area 820 is presented within the bleach area 1230 and not on any fringes of the bleach area 1230. The bleach area 1230 and the stimulus area 1220 can comprise different shapes to facilitate distinguishing between the presentation of the bleach area 1230 and the stimulus area 1220. For example, the bleach aperture 1230 can be square-shaped (having a first length 1230L) and the stimulus area 1220 can be circular (with a diameter having a second length 1220L, where the first length is larger than the second length), thereby allowing the subject to easily distinguish between the presentations of the bleach light and its after effects and the stimulus light. The fixation dot 1210 can also comprise an area (having a length 1210L) that is smaller than the areas of the bleach 1230 and stimulus 1220 areas.

FIG. 13 illustrates the image plane 1300 presented to the subject in another embodiment (e.g., a head-wearable implementation of the ophthalmic testing systems disclosed herein). In the embodiment shown in FIG. 12, the subject's eye remains positioned on the optical axis for all phases of the test. However, in the embodiment shown in FIG. 13 (which can be utilized in a head-wearable implementation), the optics can be positioned along the X-axis and configured such that they can be moved (via motorized control) along the X-axis.

Specifically, the image plane 1300 can comprise a bleach fixation light area 1310, having a first diameter 1310L. The test subject can be asked to focus her gaze on the bleach fixation light area 1310 during the bleaching process. In order to carry out the bleaching process, the bleaching area 1330 (having a first length 1330L) is moved in the image plane (e.g., along the X-direction 1340) such that a center of the bleaching area 1330 is aligned with the subject's pupil. Upon completion of the bleaching process, the subject is asked to focus her gaze on the stimulus fixation point, which can have a similar diameter 1310L as the bleach fixation light area. The bleach region is moved away from the alignment with the subject's pupil (e.g., along the X-direction 1340) and the stimulus region 1320 is moved (e.g., along the X-direction 1340') to align the center of the stimulus with the subject's pupil.

As noted, the bleach area 1330 and the stimulus area 1320 can comprise different shapes to facilitate distinguishing between the presentation of the bleach area 1330 and the stimulus area 1320. For example, the bleach aperture 1330 can be square-shaped (having a first length 1330L) and the stimulus area 1320 can be circular (with a diameter having a second length 1320L, where the first length is larger than the second length), thereby allowing the subject to easily distinguish between the presentations of the bleach light and its after effects and the stimulus light. The fixation dots

1310, 1315 can also comprise an area (having a length 1310L) that is smaller than the areas of the bleach 1330 and stimulus 1320 areas.

In some embodiments, the head-wearable device can be directly centered on the pupil, in the optical center throughout the test (i.e., the optical assembly is not shifted as described above). Using this approach, the subject can rotate his/her eye to the bleach fixation light for the bleach phase, and the stimulus fixation light for the stimulus phase. Each of these two test approaches requires appropriate device calibration based on the pupil position used for the test.

As noted, the head-wearable device can use motorized optical assemblies to accurately position the pupil and move the optical assembly to center the bleach center and the stimulus for the bleach and stimulus portions of the test, respectively. The range of intra-pupil distance for device pupil positioning is generally identified as 54 mm to 72 mm. In some embodiments (e.g., table top implementations), a motorized chin rest can be used to accurately position the pupil at the optical axis. Some variance of pupil positioning is found throughout the test based on a subject's posture and comfort throughout the test.

The bleach/stimulus lights can be projected directly through the image plane when the bleach is performed. When the stimulus is performed, a neutral density filter and ground glass diffusor are introduced between the LED and image plane, and the image plane aperture is changed to the stimulus aperture. Hotspots can be eliminated through use of a ground glass diffusor or other suitable diffuser materials known in the art when the stimulus is presented, and through defocus of the LED with respect to the image plane position when the bleach is performed. The LED used for the bleach/stimulus can include an integrated collimating lens with a narrow projection range. Corrective lenses can be introduced using a lens holder to improve the image quality presented to the user.

Figure 14A:
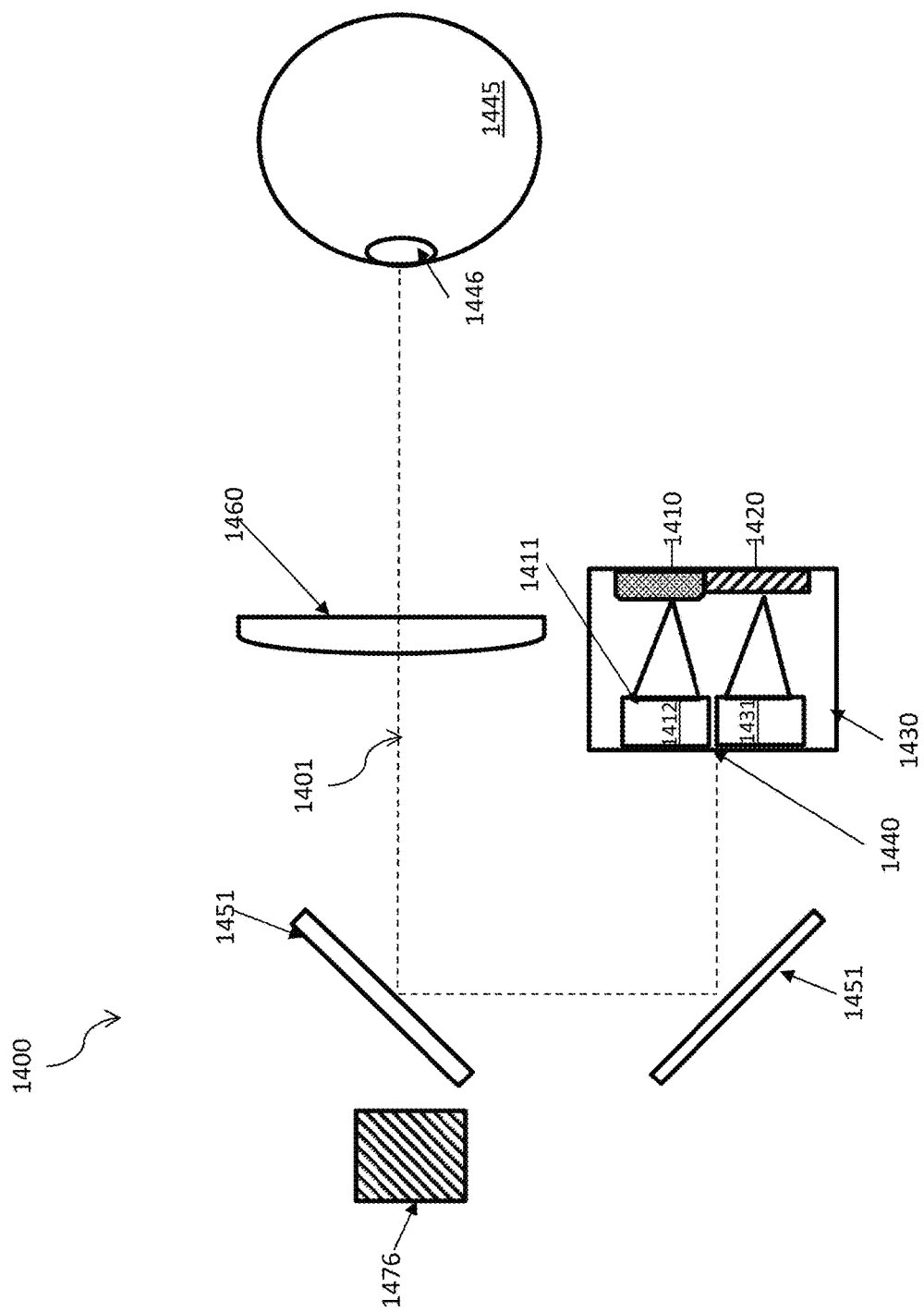
FIG. 14A illustrates a high-level cross-sectional view of some of the optics that can be used in a head-wearable implementation according to some embodiments disclosed herein.
Figure 14B:
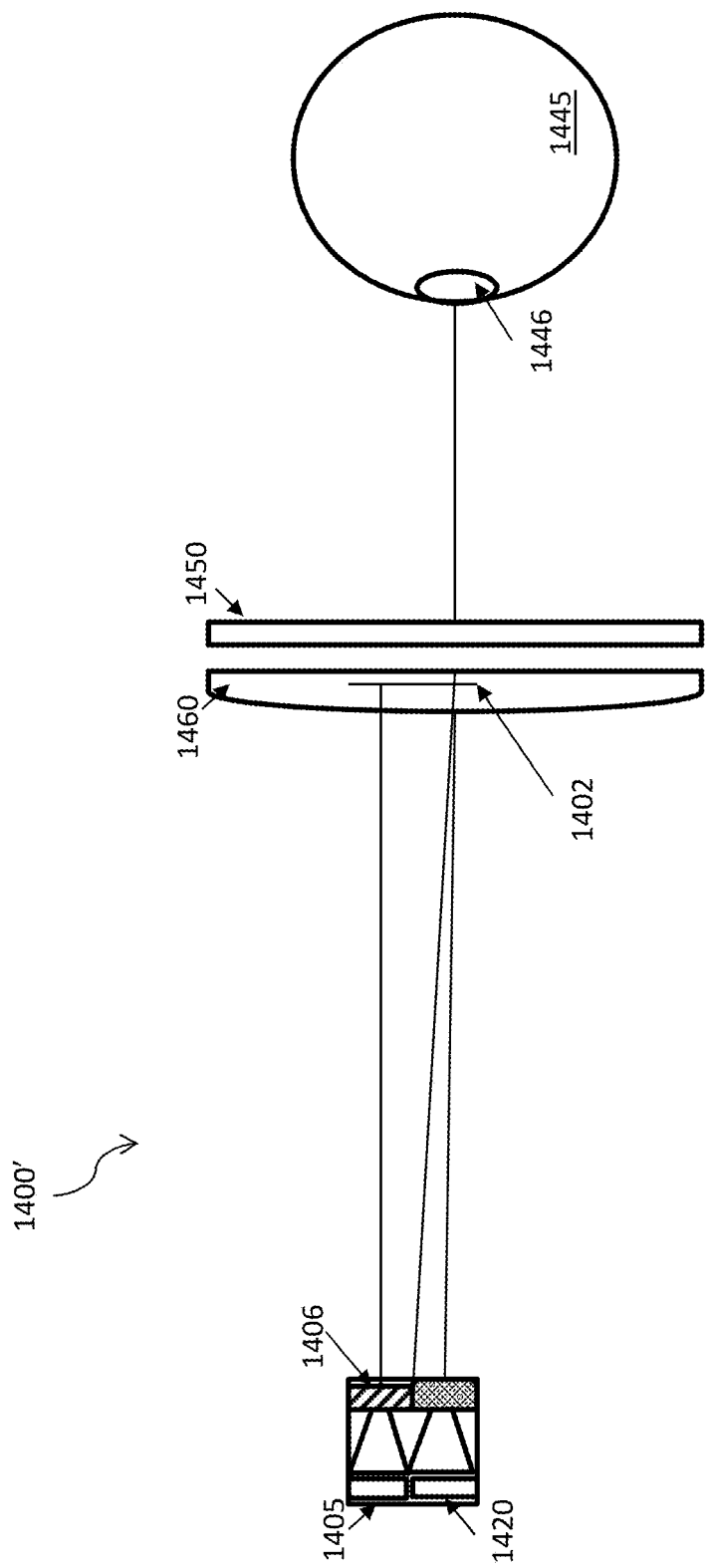
FIG. 14B illustrates another high-level cross-sectional view of some of the optics that can be used in a head-wearable implementation according to some embodiments disclosed herein.

FIGS. 14A-14B illustrate a high-level cross-sectional view 1400, 1400' of some of the optics that can be used in a head-wearable implementation according to some embodiments disclosed herein.

In FIGS. 14A-B, the center of the viewing optic 1401, as observed from the top, and a reference plane 1402 are shown. The light sources that present the fixation 1405, bleach 1420, and/or stimulus 1410 lights to the test subject can be disposed in a housing 1430, which can be any suitable housing available in the art. In some implementations, the fixation light 1405 can be presented through a diffusor 1406 in order to make the fixation dot appear with improved image uniformity (e.g., no hot spots). The bleach light 1420 can be projected directly, through an added collimating lens 1431, and through the image plane 1440, when the bleach is performed. The stimulus light can be presented through a neutral density filter 1411 and diffusor 1412 before exiting the image plane 1440.

Hotspots can be eliminated through use of the diffusor(s) 1406, 1412 for the fixation and stimulus lights, and through defocus of the light through positioning of the collimating lens 1431 with respect to the image plane 1440 position when the bleach is performed. The light source used for the bleach can include a wide-beam integrated lens. The collimating lens can be introduced after the bleach light to provide a narrow projection range. As noted above, in some embodiments, a user adjustment knob/dial can be provided in the headset to adjust the image plane distance and subjectively improve the image quality presented to the user. The knob adjusts the distance between image plane 1440 and the viewing optic 1460 to perform a spherical equivalent correction.

The image plane can be viewed via the viewing optic (e.g., 50 mm FL lens) 1460 and a protective window 1450, with no optical power positioned close to the viewing optic 1460. Light sealing features can be configured to position the eye 1445 and pupil 1446 in any suitable location (e.g., 23 mm from the surface of the protective window 1450). In some embodiments, the range of the distance from viewing optic 1460 (e.g., the 50 mm FL lens) to the eye 1445 can be 10 mm to 80 mm, 20 mm to 60 mm, or 30 mm to 40 mm.

Further, as noted above, the pupil position 1446 can be subject-dependent and determined using a pupil imaging camera 1476. As also noted previously, the optics 1400 can also comprise one or more mirrors 1451 (e.g., at least one dichroic mirror) that is configured to reflect the light from the test bleach and stimulus light sources 1410, 1420 onto the subject's pupil.

Figure 15:
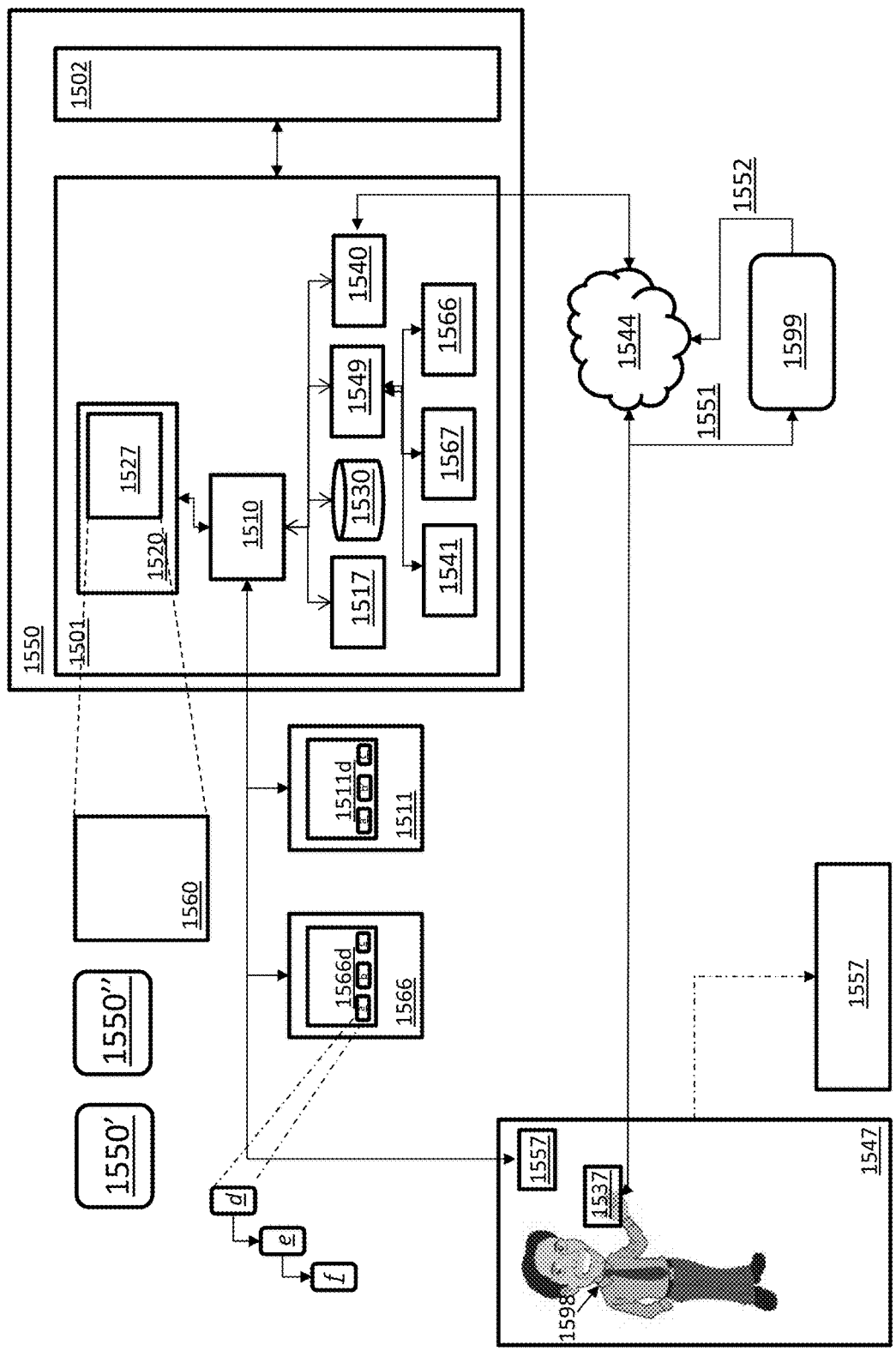
FIG. 15 is a high-level block diagram of an interface system according to some embodiments disclosed herein.

FIG. 15 is a high-level block diagram of an interface system according to embodiments disclosed herein. As noted with reference to FIG. 3, an ophthalmic testing system 1550 according to embodiments disclosed herein can include digital circuitry and relevant hardware 1501 that implement the various functions of the ophthalmic testing system 1550. Further, as detailed above, the digital circuitry 1501 can include various components including a processor 1510 that is configured to monitor the operation of the ophthalmic testing system, send and/or receive signals regarding the operation of the ophthalmic testing system, and/or control the operation of the ophthalmic testing system.

The processor 1510 can be configured to collect or receive information and data regarding the operation of the ophthalmic testing system 1550 and/or the head-wearable device 100 and/or store or forward information and data to another entity (e.g., another portion of an ophthalmic testing system, etc.). The processor 1510 can further be configured to control, monitor, and/or carry out various functions needed for analysis, interpretation, tracking, and reporting of information and data collected by the ophthalmic testing system 1550 (for example, as implemented in the head-wearable device 100 shown in FIG. 1A). Generally, these functions can be carried out and implemented by any suitable computer system and/or in digital circuitry or computer hardware, and the processor 1510 can implement and/or control the various functions and methods described herein. The processor 1510 can further be generally configured to monitor the operation of the ophthalmic testing system 1550, send and/or receive signals regarding the operation of the system 1550, and/or control the operation of the system 1550. The processor 1510 can also collect or receive data regarding the operation of the system 1550 and/or store or forward the data to another entity (e.g., a medical facility, etc.).

Generally, the processor 1510 and the CPU 1515 can be configured to receive instructions and data from the main memory 1520 (e.g., a read-only memory or a random access memory or both) and execute the instructions. The instructions and other data can be stored in the main memory 1520. The processor 1510 and the main memory 1520 can be included in or supplemented by special purpose logic circuitry. The main memory 1520 can be any suitable form of volatile memory, non-volatile memory, semi-volatile memory, or virtual memory included in machine-readable storage devices suitable for embodying data and computer program instructions. For example, the main memory 1520 can comprise magnetic disks (e.g., internal or removable disks), magneto-optical disks, one or more of a semiconductor memory device (e.g., EPROM or EEPROM), flash memory, CD-ROM, and/or DVD-ROM disks.

The main memory 1520 can hold application software 1527. For example, the main memory 1520 and application software 1527 can include various computer executable instructions, application software, and data structures, such as computer executable instructions and data structures that implement various aspects of the embodiments described herein. For example, the main memory 1520 and application software 1527 can include computer executable instructions, application software, and data structures, such as computer executable instructions and data structures that implement a subject-instruction system (e.g., an automated subject-instruction system, as detailed below), which can be employed to communicate with the subject in order to, for example, instruct the subject during an ophthalmic test.

The processor 1510 can further be coupled to a database or data storage 1530. The data storage 1530 can be configured to store information and data relating to various functions and operations of the ophthalmic testing and measurement system 1550.

The processor 1510 can further be coupled to a display 1517. The display 1570 can be configured to receive information and instructions from the processor. The display 1570 can generally be any suitable display available in the art, for example a Liquid Crystal Display (LCD) or a light emitting diode (LED) display. For example, the display 1570 can be a smart and/or touch sensitive display that can receive instructions from a user and/or provide information to the user.

The processor 1510 can further be connected to various interfaces. The connection to the various interfaces can be established via a system or an input/output (I/O) interface 1549 (e.g., Bluetooth® USB connector, audio interface, FireWire, interface for connecting peripheral devices, etc.). The I/O interface 1549 can connect to any suitable interface, for example a microphone 1566, a speaker 1567, and one or more sensors 1541.

The processor 1510 can further be coupled to a communication interface 1540, such as a network interface. The communication interface 1540 can be a communication interface that is included in the ophthalmic testing and measurement system 1550 and/or a remote communications interface 1540 that is configured to communicate with the ophthalmic testing and measurement system 1550. For example, the communications interface 1540 can be a communications interface that is configured to provide the ophthalmic testing and measurement system 1550 with a connection to a suitable communications network, through which transmission and reception of data, information, and instructions can occur. As noted above, the system 1550 can further comprise an optical system 1502 that comprises optical components for conducting various ophthalmic tests and measurements with the embodiments disclosed herein.

The one or more sensors 1541 can comprise any suitable sensors, for example one or more motion sensors configured to track and/or monitor the motion and/or movement of the system 1550 and/or the subject. For example, the system 1550 can comprise at least one motion sensor 1541 (e.g., comprising at least one of an accelerometer and/or a tilt sensor) that is configured to monitor, track, and/or collect information indicating sudden acceleration or deceleration of the system 1550.

In some embodiments, the system 1550 can comprise a motion sensor and/or an inertial measurement sensor (IMS) that can be used to collect information regarding unexpected changes in the motion of the device and/or undesired events, such as whether the system 1550 has been dropped (e.g., if a head-wearable implementation of the system has been dropped), whether the system 1550 has taken any undesired impact, whether the system 1550 has been transported from its intended usage facility (practitioners transporting a tabletop implementation between various facilities and possibly damaging the device in the process), etc.

The processor 1510 can monitor the sensors and can be configured to receive and process the information collected by the sensors 1541 can be forwarded. As noted, the information regarding movements of the ophthalmic testing system 1550 can include information regarding sudden acceleration or deceleration of the ophthalmic testing system 1550.

The processor 1510 can process this information to determine whether the device has suffered an impact (such as a fall or a drop) or experienced any other event, information about which can be of interest to an authorized party 1599. Upon processing the information collected by the sensors 1641, the processor 1510 can transmit information regarding undesired events and/or information regarding the status of the system 1550 to an entity that tracks, records, and/or makes use of such information. For example, the information regarding unexpected motions of the device can be transmitted via a communications network 1544 to an entity 1566 (e.g., original manufacturer) that provides/offers warranties on the system 1550.

The authorized party 1599 can be any entity authorized to receive information about the ophthalmic testing system 1550, such as an insurance provider (e.g., a party that has insured the ophthalmic testing system), a party that has warrantied any part of the system and/or any of the services offered by the device, and/or any person or entity that owns or operates the system.

For example, in some embodiments, the authorized party 1599 can be an original device manufacturer that warranties at least a portion of the parts and/or services included in/provided by the ophthalmic testing system 1550. Additionally or alternatively, the authorized party 1599 can be at least one of a remote entity responsible for maintenance of the ophthalmic testing system 1550 and an insurance provider providing insurance on the ophthalmic testing system 1550.

The processor can be configured to execute instructions to perform one or more tasks in response to receiving information from the sensor(s) 1541. Generally, the processor can comprise pre-established rules corresponding to different magnitudes of sensor readings and these rules can govern the nature of a notification to the user or entity 1599.

For example, the processor 1510 can be configured to execute instructions configured to quantify severity of any undesired event (e.g., sudden acceleration or deceleration events) detected by the sensor(s) 1541. In some embodiments, the processor 1510 can be configured to quantify the severity of the undesired event. For example, the processor 1510 can comprise instructions that classify or quantify sudden acceleration or deceleration events as mild, medium, and severe. For example, the processor can be configured to compare the data received from the one or more sensors and couple that data with predetermined thresholds to classify a sudden acceleration or deceleration event as mild, medium, and severe.

The processor 1510 can further be configured to generate a notification 1551 in response to receiving information (from the sensor(s) 1541) which can be of interest to the authorized party 1599 and/or transmit the generated notification to the authorized party 1599. The notification 1551 can be transmitted to the authorized party using any scheme known and available in the art. For example, the system 1550 can be configured to transmit the notification 1551 via the communications network 1544. The communications network 1544 can be any communications network known and available in the art. Further, the system 1550 and the processor 1510 can use any means (e.g., communications links, communications protocols, etc.) known and available in the art to communicate with the authorized party 1599. The system 1550 can include any communications means necessary to communicate with the authorized party via the communications network 1544.

In some embodiment, the authorized party 1599 can be a designated device configured to receive the notification 1551 generated by the ophthalmic testing system 1550. The designated device can be any suitable device known and available in the art. For example, the designated device can be any of a mobile device, a desktop computer, earbud, smart glasses with pop-up message window.

The third party/designated device 1566 can be configured to issue a response signal 1552 to the ophthalmic testing system 1550 in response to receiving the notification generated by the ophthalmic testing system 1550. The response signal 1552 can comprise instructions that can be executed by the processor 1510 to perform one or more tasks. For example, the one or more instructions can comprise instructions that, once executed by the processor, perform at least one or more of disabling the ophthalmic testing device 1550, providing a visual warning signal to the test subject 1598 (e.g., through the display 1517), and providing an audible warning signal to the test subject 1598 (e.g., through the speaker 1567).

Additionally or alternatively, the ophthalmic testing system 1650 can be configured to generate an alarm signal in response to detection of undesired events in the ophthalmic testing system 600 (e.g., sudden acceleration or deceleration of the ophthalmic testing system). In some embodiments, the alarm signal generated by the ophthalmic testing system 1550 can be output through at least one speaker 1567. As noted, the processor 1510 can be coupled to the at least one speaker 1550 via an input/output (I/O) interface 1549 of the ophthalmic testing system 1550 and configured to instruct the speaker 1550 to generate an alarm signal if/when an undesired event (e.g., sudden acceleration or deceleration of the ophthalmic testing system) is detected. In some embodiments, the alarm signal can comprise a message in natural language.

Further, in some embodiments, the one or more sensors 1541 can be configured to sense and/or track movements of the test subject 1598. For example, the system 1550, in various head-wearable implementations, can comprise one or more sensors 1541 (e.g., motion sensors, GPS sensors, accelerometers, gyroscopes, etc.) configured to detect or determine whether the test subject 1598 wearing the system 1550 has moved from his/her original position (e.g., from the position at which the system 1550 was placed on or against the subject's head). The sensor(s) 1541 can be configured to detect any type or amount of movement that may be of interest to the person or entity administering the ophthalmic test.

Further, the processor 1510 can be configured to perform similar procedures as those performed in response to detection of movement of the ophthalmic testing system 1550. Specifically, the processor 1510 can be configured to generate an alarm signal, send or receive signals, and/or receive and execute instructions in response to detection of any type or amount of movement that may be of interest to the person or entity administering the ophthalmic test. By way of example, in one embodiment, the processor 1510 can be configured to issue a signal that alerts a practitioner that a movement that may be of interest to the practitioner has occurred. In some embodiments, the processor 1510 can cause the display 1517 of the system 1550 to provide a visual message on the display 1517 of the system 1550.

As noted above, the ophthalmic testing system 1550 can include a subject-instruction system 1560 that is configured to issue various instructions for carrying out the test to the subject. The subject-instruction system 1560 can be implemented in the electronic circuitry of the ophthalmic testing system 1550, for example in application software 1527, and configured such that one or more instructions for guiding a subject can be stored in the form of instructions and/or audio files (e.g., in the form of Waveform Audio File Format) in the main memory 1520. The subject-instruction system can be configured such that upon initialization of the testing system 1550, the processor 1510 transfers audio files for instructing the subject using the subject-instruction system 1560 from the main memory and causes the execution of the files. The subject-instruction system 1560 can communicate, via the I/O interface 1549, with the one or more speakers 1567 of ophthalmic testing and measurement system 1550, and instruct the speakers 1567 to play the relevant audio files for the subject.

In some embodiments, the subject-instruction system 1560 can be employed to guide a subject, automatically, through an ophthalmic test or measurement. For example, the subject-instruction system 1560 can guide a subject through the required steps for performing an ophthalmic test, such as a dark adaptation test.

The subject-instruction system 1560 can be configured to be initialized in response to any suitable trigger known in the art. For example, the subject-instruction system 1560 can be configured such that it is initialized in response to the system 1550 being turned on, in response to activation of a button (e.g., on the display 1517), in response to the frame of the device coming in contact with the subject's skin (touch sensitive), and/or in response to the head-wearable headset being worn by the subject. Once initiated, the subject-instructions system 1560 can provide the subject with an explanation of how the test is performed and/or guide the subject through the procedures required for completion of the ophthalmic test and/or study. In one embodiment, the subject-instructions system 1560 can be mounted on the headset of a head-wearable implementation and configured to instruct the subject during the ophthalmic test and/or study (e.g., during performance of a dark adaptation measurement).

The subject-instruction system 1560 can further be configured to guide the test subject 1598 through an ophthalmic test by establishing, using the processor 1510, verbal communication with the test subject 1598. The verbal communication with the subject can be conducted using natural language. Additionally or alternatively, the verbal communication with the test subject 1598 can be performed by using one or more pre-recorded messages configured for delivery to the test subject 1598 before, during, and after the ophthalmic test. The pre-recorded messages can be stored in the database 1530 and accessed by the processor 1510 at various point during the ophthalmic test. The processor 1510 can use the audio speaker 1567 to conduct verbal communication with the test subject 1598.

The verbal communication can comprise one or more commands conveyed to the test subject 1598. For example, the verbal communication can include commands that guide the subject through the test by instructing the subject to focus on a certain fixation point, instructing the subject to keep his/her eyes open, instructing the subject to blink/not to blink at certain points of time during the test, etc. Additionally or alternatively, the one or more commands can include communications exchange (e.g., by providing verbal commands to the subject and receiving natural language responses from the subject) between the system 1550 and the subject. In order to achieve the communication exchange, the system 1650 can utilize an audio inlet (e.g., speaker 1566) to receive communication messages from the test subject 1598. The communication messages can be issued by the test subject 1598 in natural language.

For example, the one or more commands can comprise communications exchange requesting information regarding subject's records (e.g., subject's address, phone number, insurance, prescriptions, preferred pharmacy, etc.), advertisements for recommended treatments or tests, education regarding lifestyle changes associated with a condition or slowing disease progression, etc. In some embodiments, the one or more commands can provide the subject with information such as referral to another provider or physician (e.g., ophthalmologist, retina specialist, etc.).

Further, the one or more commands can comprise commands provided for guiding the test subject 1598 through the ophthalmic test. For example, the verbal communication can comprise at least one of 1) greeting the test subject 1598, 2) commands providing address or location of an exam room in which the ophthalmic test is administered, 3) information regarding the ophthalmic test, and 4) expected wait time until the ophthalmic test is administered.

The processor 1510 can be configured to monitor the response received from the test subject 1598 via the interface 1555. In some embodiments, the processor 1510 can be configured to store the response received from the test subject 1598 for future analysis and compare the response received from the test subject 1598 to a baseline response stored in the memory. The processor 1510 can further be configured to adjust at least one function of the ophthalmic testing system based on the response received from the test subject 1598. For example, the processor 1510 can be configured to monitor a test subject's response to a stimulus light and, based on the subject's response, determine whether the length of the test should be shortened or extended. Alternatively or additionally, the processor can be configured to change various configurations of the ophthalmic testing system 1550 based on the response received from the test subject 1598. For example, the processor can change at least one of position of a component of the optical system and orientation of a component of the optical system. Additionally or alternatively, the processor can adjust at least one of 1) position of a component of the optical system, 2) orientation of a component of the optical system, and 3) length of the ophthalmic test. In some embodiments, the processor can also provide the test subject 1598 with additional instructions upon receiving a response from the test subject 1598.

As noted, the system 1550 can comprise an audio inlet, such as a microphone 1566 that is configured to receive a verbal response from the test subject 1598. The verbal response of the test subject 1598 can be provided to the system 1550 in the form of natural language and be processed by the processor 1510. The processor 1510 can process the verbal response of the test subject 1598 and provide the test subject 1598 with additional commands and instructions. The additional commands can comprise at least one of 1) natural language commands, 2) pre-recorded audio commands, 3) computer-generated audio commands, 4) visual commands, and 5) physical commands or prompts (e.g., vibrations).

The system 1550 can process the instructions received from the subject by extracting one or more active elements of an active ontology associated with the user's response, determining at least one task for which to provide the test subject with assistance based on the active ontology, and providing the test subject with assistance by performing the at least one task. Generally, any suitable technique available in the art can be used to extract the active ontology associated with the user's verbal response.

In some embodiments, the verbal response of the test subject 1598 can comprise one or more requests for assistance. The one or more requests can be issued by the test subject 1598 in natural language. In response to receiving the verbal request for assistance, the processor 1510 can extract one or more active elements of an active ontology associated with the one or more requests, determine at least one task for which to provide the test subject 1598 with assistance based on the active ontology, and provide the test subject 1598 with assistance by performing the at least one test. Non-limiting examples of assistive tasks can include provision for a rest break or pause in the test, clarification of how to don or remove the given ophthalmic test system, clarification or repeating of test instructions, and additional information or education about the test procedure, instrumentation, anatomy, and/or physiology related to the test.

As noted, the subject-instructions system 1560 can be configured to guide a test subject 1598 through the test and the test environment. For example, upon arriving at the testing location 1547, the test subject 1598 can be paired with a device 1537 configured to track and/or report the exact location of the test subject. The device 1537 can be a mobile device associated with the subject 1598. The device 1537 can be configured such that it communicates the location of the test subject 1598 within the test environment 1547 to the processor 1510. In other words, the processor 1510 can be configured to communicate (via a communication link or network 1544) with the location-determining device 1537 associated with the test subject 1598 to monitor the location of the test subject and guide the test subject 1598 through the testing location 1547 to the exam room 1557. It should be noted that although shown as the processor 1510 of the ophthalmic testing system 600, the processor can be any processor in the testing location 1547, for example a processor implemented in or coupled with the location-determining device 1537. Further, embodiments disclosed herein are not limited to use with ophthalmic testing systems. Generally, the systems, methods, and apparatus disclosed herein for guiding test subjects through a testing location to an exam room can be used in any testing or exam facility (having medical or non-medical nature) or any facility in which a client is instructed to wait and/or needs to be directed to a location where he/she receives his/her intended services. Further, any portion of the systems disclosed herein can be implemented on a chip. For example, the systems for determining the health of the system can be implemented on a chip and installed in any device, the health which an authorized party may be interested in tracking.

Referring back to FIG. 15, the processor 1510 can further be configured to communicate with a plurality of speakers 1557 dispersed throughout the testing location 1547 for guiding the test subject to the exam room 1557. The processor 1510 can activate each of the speakers based 1557 on proximity of the location of the test subject location-determining device 1537 to that speaker 657. Alternatively or additionally, the processor 1510 can be configured to communicate with a program executing on the subject location-determining device 1537 for presenting a map to the test subject and visually guiding the test subject to the exam room 1557. In some embodiments, the location-determining device 1537 can comprise an RFID tag interfacing with RFID readers distributed throughout a clinic or office. Further, in some implementations, the location-determining device can comprise a smartphone interfacing with an office or clinic-based WiFi or Bluetooth® network.

The processor 1510 can issue one or more commands comprising pre-recorded messages to the test subject 1598. The one or more commands can be configured for delivery to the test subject before, during, and after the ophthalmic test. The processor 1510 can also receive one or more requests for assistance from the test subject 1598. The one or more requests can comprise at least one of 1) questions regarding the test and 2) complaints regarding the test.

Further, the processor can be configured to execute instructions that provide the test subject with assistance by performing at least one of: 1) guiding the test subject 1598 in conducting the ophthalmic testing, 2) notifying a practitioner monitoring the ophthalmic testing, 3) adjusting at least one function of the ophthalmic measurement and testing device, and 4) configuring at least one element of the ophthalmic measurement and testing device.

Figure 16:
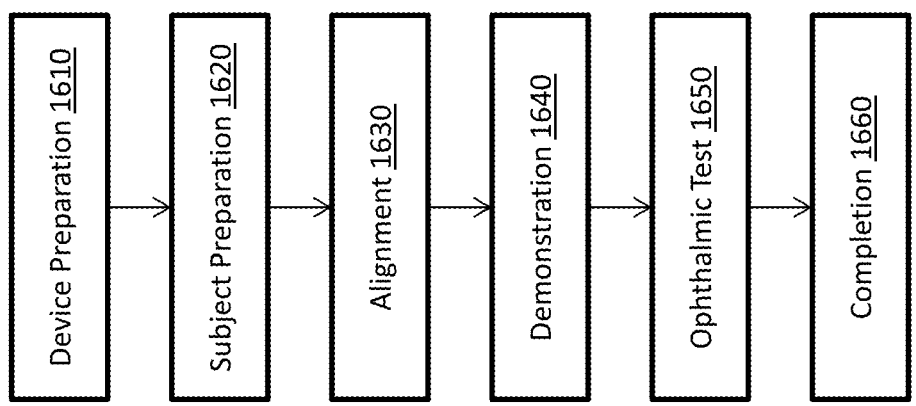
FIG. 16 is a high-level flow diagram of the procedures that can be used by the subject-instruction system according to some embodiments disclosed herein.

FIG. 16 is a high-level flow diagram of the procedures that can be used by the subject-instruction system 1560 to provide the subject with instructions for performing and/or completing of the ophthalmic test and/or study. As shown in FIG. 16, the procedures can comprise device preparation 1610, subject preparations 1620, alignment 1630, demonstration 1640, ophthalmic test 1650, and test completion 1660.

During device preparation 1610, the test subject is prepared for the ophthalmic test and test parameters are set. The test subject can be prepared by a technician, physician, or a practitioner and/or by an automated system that automatically sets the parameters for conducting the test. Specifically, during subject preparations 720, the test subject can be provided with an introduction to the ophthalmic testing system (e.g., the head-wearable implementation of the system) and provided with guidance as how the system operates and/or the procedures that the subject must follow in order to complete the ophthalmic test. The subject can receive the introductory comments from a live technician, physician, or a practitioner and/or from an automated system that is configured to guide the test subject through the test. For example, the subject can be introduced to the ophthalmic testing system by being guided to watch a video and/or by being guided through a simulated or a sample test. In embodiments that utilize an automated system, the subject can be given the option of communicating with the automated system via audio commands. The audio commands can be provided by the subject in natural language. As described with reference to FIG. 4A, during the test subject preparation phase, the clinician can use the interface 460 to setup the test and initialize the test. Once the test is setup, the clinician can pass the interface 460 to the test subject for use in conducting the test.

During the alignment 1630 phase, the ophthalmic testing system can automatically align the subject's pupils to the image plane (e.g., crosshairs included in the image plane). The subject's pupils can be aligned to the image plane manually (e.g., by a technician) and/or using an automated system that automatically detects the subject's pupils and adjusts the image plane accordingly. As shown in FIG. 15, in some embodiments, the ophthalmic testing system 1550 can comprise a provider interface 1511 that has been configured to allow an operator (e.g., technician) to align the subject's pupils to crosshairs or other features included in the image plane. For example, the provider interface can comprise a display 1511d that displays an image of the subject's pupil and also an image of the image plane and allows the clinician to adjust the pupil to the image plane (e.g., cross hairs on the image plane). Adjustments on the screen 1511d of the provider interface 1511 can trigger the processor 1510 to move the platforms carrying the optical elements (e.g., light sources, as described with reference to FIG. 6) of the optical system 1502, thereby bringing the subject's pupils in alignment with the image plane.

During demonstration 1640, the ophthalmic testing system can automatically take the subject through a demonstration test to inform the subject of the testing procedures. During the ophthalmic test 1650, the ophthalmic testing system can automatically take the subject through the actual ophthalmic test to collect data and/or images. The test is completed 1660 by the technician/subject removing the subject from the device and/or collecting the head-mounted device from the subject and logging the results into the subject's record. As described with reference to FIG. 4A, at this point of the testing process, the processor 1510 can bring the interface 460 back into the clinician mode.

Referring back to FIG. 15, the system 1550 can further comprise a provider interface 1511 and/or a command screen 1550 that can allow a provider to select from among multiple head-wearable devices, each offering a different ophthalmic test. Specifically, as noted with reference to FIGS. 4A and 4A-1, the ophthalmic testing system 1550 can be configured to provide the clinician with one or more menus or icons for use in initializing and/or conducting an ophthalmic test. The menus and icons can be presented to the provider and/or the test subject via the provider interface 1511 and/or via a command center 1566 that is configured to control functions of the system 1550. The provider interface 1511 and/or the command center 1566 can be configured to store or access a database 1530 that stores information regarding the devices that offer various tests and the test(s) offered (e.g., cloud-based subject database), electronic health record, or practice management system.

The display 1511d/1566d of the interface 1511/command center 1566 can present to a user a plurality of icons a,b,c/a',b',c', each of which can represent one of the systems 1550, 1550', 1550" (e.g., one of multiple head-wearable devices) that is in communication with the command center 1566/interface 1511. In some embodiments, the user can select an icon, e.g., by clicking on that icon, to initiate communication with the head-wearable device associated with that icon. By way of example, by selecting an icon a,b,c/a',b',c', the user can establish a communication channel with a head-wearable device corresponding to that icon. The selection of an icon a/a' can result in selection of the device 1550 corresponding to that icon. Once the device 1550 is selected, the system can present a menu 1050 to the user, which contains a list of commands from which the user can choose for instructing the head-wearable device 1550 associated with that icon a1a' to perform a desired function. For example, the menu a can include a menu item d that allows the provider to determine whether device is being worn or used by another user. By selecting menu item d, the provider can determine whether a particular head-wearable device 1550 is being worn by a subject.

In response, the command center can receive data from one or more sensors 1571 incorporated on the head-wearable device to determine whether the head-wearable device is being worn by a subject (e.g., for example a pressure sensor included in the strap of a head-wearable implementation, where the pressure sensor is in communication with the processor 1510 and the processor 1510 can determine based on the information received from the sensor if the head-wearable device is being worn).

Subsequently, another menu item e, can be presented on the screen 1566*d*/1511*d*. The selection of this menu item can provide the user with the option of communicating with the subject, thereby allowing the provider to initiate verbal and/or visual communication with a subject wearing the head-wearable device 1550. For example, upon selection of this item, the command center 1566 can allow the user to provide verbal instructions to the subject, e.g., to prepare the subject for the initiation of an ophthalmic test. The user can then select another menu item f to initiate a test using the ophthalmic testing system 1550 on the test subject 1598.

Those having ordinary skill in the art will appreciate that various changes can be made to the above embodiments without departing from the scope of the invention. Although this specification discloses advantages in the context of certain illustrative, non-limiting embodiments, various changes, substitutions, permutations, and alterations may be made without departing from the scope of the specification as defined by the appended claims. Further, any feature described in connection with any one embodiment may also be applicable to any other embodiment.

What is claimed is:

1. A head-wearable ophthalmic testing and measurement system comprising:
   a head-wearable frame;
   at least one test light source mounted in the head-wearable frame in front of at least one eye of a test subject and configured to generate a test light configured to illuminate the at least one eye of a test subject;
   at least one optical system mounted in the head-wearable frame in front of at least one eye of a test subject and configured to direct the test light generated by the at least one test light source onto the at least one the eye of the test subject; and
   a movable platform on which the at least one test light source and the at least one optical system are mounted, the movable platform being mounted within the head-wearable frame and movable along at least two orthogonal directions within the head-wearable frame and configured to move the at least one test light source within the frame and align the at least one test light source relative to a pupil of the at least one eye of the test subject.

2. The head-wearable ophthalmic testing and measurement system of claim 1, further comprising at least one fixation light source configured to generate a fixation light that directs attention of the test subject to the light generated by the at least one test light source.

3. The head-wearable ophthalmic testing and measurement system of claim 2, wherein the at least one fixation light source is movable within the head-wearable frame to bring the fixation light into focus when viewed by the test subject.

4. The head-wearable ophthalmic testing and measurement system of claim 3, further comprising at least one mechanism mounted onto the head-wearable frame and coupled to the at least one fixation light source, wherein the mechanism is configured to move the at least one fixation light source within the head-wearable frame relative to the at least one eye of the test subject to bring the fixation light into focus when viewed by the test subject.

5. The head-wearable ophthalmic testing and measurement system of claim 4, wherein the at least one mechanism comprises a knob, configured to be rotationally moveable to move the at least one fixation light source within the head-wearable frame, and a cam mechanically coupled to the knob and configured to transform rotational movement of the knob to linear translation of the at least one fixation light source.

6. The head-wearable ophthalmic testing and measurement system of claim 5, further comprising an automatic alignment mechanism coupled to the head-wearable frame, wherein the automatic alignment mechanism is configured to automatically move the at least one test light source within the head-wearable frame and align the at least one test light source with the pupil of the at least one eye of the test subject.

7. The head-wearable ophthalmic testing and measurement system of claim 6, wherein the automatic alignment mechanism comprises: an infrared light source mounted in the head-wearable frame and configured to illuminate the at least one eye of the test subject and an infrared detector mounted in the head-wearable frame and configured to detect at least a portion of infrared light returning from the at least one eye of the test subject.

8. The head-wearable ophthalmic testing and measurement system of claim 1, further comprising a light seal configured to isolate the at least one eye of the test subject from ambient light.

9. The head-wearable ophthalmic testing and measurement system of claim 8, further comprising a head-mount coupled to the head-wearable frame and configured to secure the head-wearable frame and the light seal against an area surrounding the at least one eye of the test subject.

10. The head-wearable ophthalmic testing and measurement system of claim 9, further comprising a ratchet coupled to the head-mount and configured to form a tension in the head-mount that presses the light seal against the area surrounding the at least one eye of the test subject.

11. The head-wearable ophthalmic testing and measurement system of claim 10, wherein the light seal is configured to conform to the area surrounding the at least one eye of the test subject in response to the tension.

12. The head-wearable ophthalmic testing and measurement system of claim 11, wherein the light seal is removably coupled to an optical interface of the head-wearable ophthalmic testing and measurement device.

13. The head-wearable ophthalmic testing and measurement system of claim 1, further comprising a sealed package that houses the at least one test light source and the at least one optical system.

14. The head-wearable ophthalmic testing and measurement system of claim 12, wherein the head-mount further comprises an adjustable strap coupled to the ratchet, wherein the ratchet is configured to adjust a length of the strap to form the tension that presses the light seal to the area surrounding the at least one eye of the test subject.

15. The head-wearable ophthalmic testing and measurement system of claim 1, further comprising at least one sensor coupled to the head-wearable frame and configured to detect undesired movements of the test subject.

16. The head-wearable ophthalmic testing and measurement system of claim 1, further comprising a test subject response interface configured to receive feedback provided by the test subject in response to exposure to the test light generated by the at least one test light source.

* * * * *